(12) United States Patent
Devalaraja-Narashimha

(10) Patent No.: US 12,084,516 B2
(45) Date of Patent: Sep. 10, 2024

(54) ANTI-C5 ANTIBODY COMBINATIONS AND USES THEREOF

(71) Applicant: Regeneron Pharmaceuticals, Inc., Tarrytown, NY (US)

(72) Inventor: Kishor Devalaraja-Narashimha, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 73 days.

(21) Appl. No.: 17/663,675

(22) Filed: May 17, 2022

(65) Prior Publication Data

US 2022/0275107 A1 Sep. 1, 2022

Related U.S. Application Data

(62) Division of application No. 16/217,290, filed on Dec. 12, 2018, now Pat. No. 11,365,265.

(60) Provisional application No. 62/598,023, filed on Dec. 13, 2017.

(51) Int. Cl.
| | |
|---|---|
| *A61K 39/395* | (2006.01) |
| *A61P 3/06* | (2006.01) |
| *A61P 7/04* | (2006.01) |
| *A61P 9/10* | (2006.01) |
| *A61P 9/12* | (2006.01) |
| *A61P 43/00* | (2006.01) |
| *C07K 14/47* | (2006.01) |
| *C07K 16/18* | (2006.01) |
| *C07K 16/34* | (2006.01) |
| *C07K 16/40* | (2006.01) |
| *C07K 16/44* | (2006.01) |
| A61K 31/573 | (2006.01) |
| A61K 31/727 | (2006.01) |
| A61K 39/00 | (2006.01) |

(52) U.S. Cl.
CPC .......... *C07K 16/44* (2013.01); *A61K 39/3955* (2013.01); *A61P 3/06* (2018.01); *A61P 7/04* (2018.01); *A61P 9/10* (2018.01); *A61P 9/12* (2018.01); *A61P 43/00* (2018.01); *C07K 14/472* (2013.01); *C07K 16/18* (2013.01); *C07K 16/34* (2013.01); *C07K 16/40* (2013.01); A61K 31/573 (2013.01); A61K 31/727 (2013.01); A61K 2039/505 (2013.01); A61K 2039/507 (2013.01); A61K 2039/545 (2013.01); C07K 2317/31 (2013.01); C07K 2317/33 (2013.01); C07K 2317/51 (2013.01); C07K 2317/515 (2013.01); C07K 2317/76 (2013.01)

(58) Field of Classification Search
None
See application file for complete search history.

(56) References Cited

U.S. PATENT DOCUMENTS

| | | |
|---|---|---|
| 4,686,100 A | 8/1987 | Raffin et al. |
| 4,816,567 A | 3/1989 | Cabilly et al. |
| 5,562,904 A | 10/1996 | Rother et al. |
| 5,853,722 A | 12/1998 | Rollins et al. |
| 6,074,642 A | 6/2000 | Wang et al. |
| 6,331,415 B1 | 12/2001 | Cabilly et al. |
| 6,355,245 B1 | 3/2002 | Evans et al. |
| 6,534,058 B2 | 3/2003 | Fung et al. |
| 6,596,541 B2 | 7/2003 | Murphy et al. |
| 6,866,845 B1 | 3/2005 | Ward et al. |
| 7,279,158 B2 | 10/2007 | Wang et al. |
| 7,361,339 B2 | 4/2008 | Bell |
| 7,432,356 B2 | 10/2008 | Fung et al. |
| 7,582,298 B2 | 9/2009 | Stevens et al. |
| 7,745,608 B2 | 6/2010 | Manoharan et al. |
| 7,763,708 B2 | 7/2010 | Okada et al. |
| 7,923,221 B1 | 4/2011 | Cabilly et al. |
| 7,999,081 B2 | 8/2011 | Tedesco et al. |
| 8,206,716 B2 | 6/2012 | Fung et al. |
| 8,241,628 B2 | 8/2012 | Diefenbach-Streiber et al. |
| 8,246,995 B2 | 8/2012 | Dai et al. |
| 8,257,740 B1 | 9/2012 | Sung et al. |
| 8,282,929 B2 | 10/2012 | Tedesco et al. |
| 8,372,404 B2 | 2/2013 | Fung et al. |

(Continued)

FOREIGN PATENT DOCUMENTS

| | | | |
|---|---|---|---|
| AU | 2013200223 B2 | 8/2015 | |
| AU | 2014201433 B2 | 5/2016 | |

(Continued)

OTHER PUBLICATIONS

Winter et al., "Humanized antibodies", Immunol Today (1993), 14(6):243-246.

(Continued)

*Primary Examiner* — Christine J Saoud
*Assistant Examiner* — Jon M Lockard
(74) *Attorney, Agent, or Firm* — Fox Rothschild, LLP; Thomas Triolo

(57) ABSTRACT

The present invention relates to combinations of anti-C5 antibodies and antigen-binding fragments which have been determined to exhibit superior activity relative to that of a single anti-C5 antibody or fragment. The combinations include anti-C5 antibodies and antigen-binding fragments which do not compete with one another from C5 binding. Bispecific antibodies comprising antigen-binding domains which do not compete and/or bind the same epitope on C5 are also provided. Compositions and therapeutic methods relating to such anti-C5 combinations and bispecific antibodies are provided herein.

15 Claims, 15 Drawing Sheets

Specification includes a Sequence Listing.

(56) References Cited

U.S. PATENT DOCUMENTS

| | | | |
|---|---|---|---|
| 8,445,190 B2 | 5/2013 | Lambris et al. | |
| 8,703,136 B2 | 4/2014 | Baas et al. | |
| 8,802,096 B2 | 8/2014 | Guo et al. | |
| 8,883,158 B2 | 11/2014 | Diefenbach-Streiber et al. | |
| 8,886,162 B2 | 11/2014 | Raleigh | |
| 8,907,072 B2 | 12/2014 | Fung et al. | |
| 8,962,819 B2 | 2/2015 | Tedesco et al. | |
| 8,999,340 B2 | 4/2015 | Magro | |
| 9,011,852 B2 | 4/2015 | Rother et al. | |
| 9,051,365 B2 | 6/2015 | Johnson et al. | |
| 9,073,983 B2 | 7/2015 | Guo et al. | |
| 9,079,949 B1 | 7/2015 | Andrien, Jr. et al. | |
| 9,107,861 B1 | 8/2015 | Andrien, Jr. et al. | |
| 9,133,269 B2 | 9/2015 | McConnell et al. | |
| 9,206,251 B2 | 12/2015 | Andrien, Jr. et al. | |
| 9,221,901 B2 * | 12/2015 | Rother | A61P 37/06 |
| 9,388,235 B2 | 7/2016 | Halstead et al. | |
| 9,415,102 B2 | 8/2016 | Zhou et al. | |
| 9,447,176 B2 | 9/2016 | Rother et al. | |
| 9,458,233 B2 | 10/2016 | Guo et al. | |
| 9,494,601 B2 | 11/2016 | McKnight et al. | |
| 9,663,574 B2 | 5/2017 | Andrien, Jr. et al. | |
| 9,718,880 B2 | 8/2017 | Bell et al. | |
| 9,725,504 B2 | 8/2017 | Bell et al. | |
| 9,732,149 B2 | 8/2017 | Bell et al. | |
| 9,765,135 B2 | 9/2017 | Ruike et al. | |
| 9,890,377 B2 | 2/2018 | Igawa et al. | |
| 9,891,219 B2 | 2/2018 | Lennon et al. | |
| 10,472,623 B2 | 11/2019 | Igawa et al. | |
| 10,633,434 B2 | 4/2020 | Hu et al. | |
| 2004/0101920 A1 | 5/2004 | Radziejewski et al. | |
| 2004/0115194 A1 | 6/2004 | Wang | |
| 2009/0175875 A1 | 7/2009 | Etemad-Gilbertson et al. | |
| 2010/0331527 A1 | 12/2010 | Davis et al. | |
| 2011/0195454 A1 | 8/2011 | McWhirter et al. | |
| 2012/0230982 A1 | 9/2012 | Zhou et al. | |
| 2012/0308559 A1 | 12/2012 | Bell et al. | |
| 2013/0022615 A1 | 1/2013 | Diefenbach-Streiber et al. | |
| 2013/0064836 A1 | 3/2013 | Diefenbach-Streiber et al. | |
| 2014/0056888 A1 | 2/2014 | Zhou et al. | |
| 2014/0170140 A1 | 6/2014 | Bennett et al. | |
| 2014/0243504 A1 | 8/2014 | Davis et al. | |
| 2015/0158936 A1 | 6/2015 | Johnson et al. | |
| 2015/0299305 A1 | 10/2015 | Andrien et al. | |
| 2016/0031975 A1 | 2/2016 | Diefenbach-Streiber et al. | |
| 2016/0051673 A1 | 2/2016 | Hunter et al. | |
| 2016/0068592 A1 | 3/2016 | Chung et al. | |
| 2016/0168237 A1 | 6/2016 | Fontenot et al. | |
| 2016/0200805 A1 | 7/2016 | Fung et al. | |
| 2016/0237146 A1 | 8/2016 | Connor | |
| 2016/0299305 A1 | 10/2016 | Fabian et al. | |
| 2016/0362482 A1 | 12/2016 | Medof | |
| 2016/0369010 A1 | 12/2016 | Celeste et al. | |
| 2017/0065677 A1 | 3/2017 | Weston-Davies | |
| 2017/0355757 A1 | 12/2017 | Hu et al. | |
| 2018/0016327 A1 | 1/2018 | Murata et al. | |
| 2018/0022824 A1 | 1/2018 | Baas et al. | |
| 2018/0333488 A1 | 11/2018 | Francois et al. | |
| 2019/0177436 A1 | 6/2019 | Devalaraja-Narashimha | |
| 2020/0262900 A1 | 8/2020 | Hu et al. | |
| 2020/0262901 A1 | 8/2020 | Hu et al. | |

FOREIGN PATENT DOCUMENTS

| | | |
|---|---|---|
| AU | 2015201676 B2 | 10/2016 |
| CN | 102170906 A | 8/2011 |
| EP | 0219524 B1 | 1/1992 |
| EP | 1425042 B1 | 4/2007 |
| EP | 0758904 B1 | 11/2009 |
| EP | 1325033 B1 | 11/2009 |
| EP | 1529063 B1 | 4/2011 |
| EP | 1720571 B1 | 6/2012 |
| EP | 2113516 B1 | 5/2014 |
| EP | 1755674 B1 | 11/2014 |
| EP | 2061810 B1 | 11/2014 |
| EP | 1988882 B1 | 12/2014 |
| EP | 2328616 B1 | 4/2015 |
| EP | 2894165 A1 | 7/2015 |
| EP | 2563813 B1 | 8/2015 |
| EP | 2698166 B1 | 9/2015 |
| EP | 1545611 B1 | 11/2016 |
| EP | 2359834 B1 | 11/2016 |
| EP | 2380907 B1 | 11/2016 |
| EP | 2504362 B1 | 11/2016 |
| EP | 2542255 B1 | 11/2016 |
| EP | 3124029 A1 | 2/2017 |
| EP | 2552955 B1 | 5/2017 |
| EP | 3167888 A1 | 5/2017 |
| EP | 2815766 B1 | 7/2017 |
| EP | 1878441 B1 | 1/2018 |
| EP | 2978451 B1 | 11/2019 |
| JP | 2012-531418 A | 12/2012 |
| WO | 9302188 A1 | 2/1993 |
| WO | 9400560 A1 | 1/1994 |
| WO | 9529697 A1 | 11/1995 |
| WO | 9609043 A1 | 3/1996 |
| WO | 200230985 A2 | 4/2002 |
| WO | 2004007553 A1 | 1/2004 |
| WO | 200422096 A1 | 3/2004 |
| WO | 2004/106369 A2 | 12/2004 |
| WO | 04106369 A2 | 12/2004 |
| WO | 2005074607 A2 | 8/2005 |
| WO | 20050103081 A2 | 11/2005 |
| WO | 2006122257 A2 | 11/2006 |
| WO | 2007/028968 A1 | 3/2007 |
| WO | 200756227 A2 | 5/2007 |
| WO | 2007106585 A1 | 9/2007 |
| WO | 0829169 A2 | 3/2008 |
| WO | 200829167 A1 | 3/2008 |
| WO | 200830505 A2 | 3/2008 |
| WO | 2008069889 A2 | 6/2008 |
| WO | 2009125825 | 10/2009 |
| WO | 2010/015608 A1 | 2/2010 |
| WO | 2010151526 A1 | 12/2010 |
| WO | 2011137395 A1 | 11/2011 |
| WO | 2013174936 A1 | 11/2013 |
| WO | 2014047500 A1 | 3/2014 |
| WO | 2014119969 A1 | 8/2014 |
| WO | 2014160958 A1 | 10/2014 |
| WO | 201539126 A1 | 3/2015 |
| WO | 2015103438 A2 | 7/2015 |
| WO | 2015/120130 A1 | 8/2015 |
| WO | 2015/127134 A2 | 8/2015 |
| WO | 2015/134894 A1 | 9/2015 |
| WO | 2015140304 A1 | 9/2015 |
| WO | 15171523 A1 | 11/2015 |
| WO | 2015/198243 A2 | 12/2015 |
| WO | 1609956 A1 | 1/2016 |
| WO | 201694834 A2 | 6/2016 |
| WO | 2016098356 A1 | 6/2016 |
| WO | 2016117346 A1 | 7/2016 |
| WO | 2016/160756 A2 | 10/2016 |
| WO | 2016/178980 A1 | 11/2016 |
| WO | 16201301 A1 | 12/2016 |
| WO | 2016200627 A1 | 12/2016 |
| WO | 2016201301 A1 | 12/2016 |
| WO | 201735362 A1 | 3/2017 |
| WO | 201744811 A1 | 3/2017 |
| WO | 2017/062649 A1 | 4/2017 |
| WO | 2017/064615 A1 | 4/2017 |
| WO | 201755908 A1 | 4/2017 |
| WO | 2017/075325 A1 | 5/2017 |
| WO | 2017/104779 A1 | 6/2017 |
| WO | 2017/123636 A1 | 7/2017 |
| WO | 2017/132259 A1 | 8/2017 |
| WO | 2017140903 A1 | 8/2017 |
| WO | 17205101 A1 | 11/2017 |
| WO | 2017/212375 A1 | 12/2017 |
| WO | 17214518 A1 | 12/2017 |
| WO | 2017212391 A1 | 12/2017 |
| WO | 2017217524 A1 | 12/2017 |
| WO | 2017218515 A1 | 12/2017 |
| WO | 1809588 A1 | 1/2018 |
| WO | 2018053039 A1 | 3/2018 |

(56) References Cited

FOREIGN PATENT DOCUMENTS

| WO | 1871624 A1 | 4/2018 |
|---|---|---|
| WO | 18106589 A1 | 6/2018 |
| WO | 2018109588 A2 | 6/2018 |
| WO | 2018143266 A1 | 8/2018 |
| WO | 18165062 A1 | 9/2018 |
| WO | 18175833 A1 | 9/2018 |
| WO | 18195034 A1 | 10/2018 |
| WO | 18234118 A1 | 12/2018 |
| WO | 2021034639 A1 | 2/2021 |

OTHER PUBLICATIONS

Noris et al., "Dynamics of complement activation in aHUS and how to monitor eculizumab therapy", Blood, 124 (11):1715-1726 (2014).
Notice of Allowance dated Dec. 7, 2021, for U.S. Appl. No. 16/819,977.
Notice of Allowance dated Nov. 16, 2021 for U.S. Appl. No. 16/217,290.
Nozaki et al., "Drusen complement components C3a and C5a promote choroidal neovascularization", PNAS, 103(7):2328-2333 (2006).
NPL_Q1 2017 Regeneron Pharmaceuticals Inc Earnings Call Transcript (May 4, 2017).
Pinche-Nicholas, et al: "Changes in Complementarity-Determining Regions Significantly Alter IgG Binding to the Neonatal Fc Receptor (FcRN) and Pharmacokinetics", MABS 2018, vol. 10, No. 1, pp. 81-94, doi. org/10.1080/19420862.2017.1389355. 2018.
Preliminary Amendment filed Mar. 20, 2020, for U.S. Appl. No. 16/819,977.
Rother, R. P. et al., "Discover and Development of the Complement Inhibitor Eculizumab for the Treatment of Paroxysmal Nocturnal Hemoglobinuria", Nature Biotechnology, Gale Group Inc, vol. 25, No. 11, pp. 1256-1264, Nov. 2007.
Rudikoff et al., "Single amino acid substitution altering antigen-binding specificity", Proc. Natl. Acad. Sci. USA, (Mar. 1982) 79:1979-1983.
Rudikoff, et al: "Single Amino Acid Substitution Altering Antigen-Binding Specificity", Proc Natl Acad Sci USA, vol. 79: pp. 1979-1983, Mar. 1982.
Sahelijo et al., "First in Human Single-Ascending Dose Study: Safety, Biomarker, Pharmacokinetics and Exposure-Response Relationships of ALXN1210, a Humanized Monoclonal Antibody to C5, with Marked Half-Life Extension and Potential for Significantly Longer Dosing Intervals", Blood, 126(23):4777 (2015).
Slamon et al. "Use of chemotherapy plus a monoclonal antibody against HER2 for metastatic breast cancer that overexpresses HER2.", New Engl. J. Med. (2001), 344:783-792.
Soliris prescription label, copyright 2018.
States et al., "Improved sensitivity of nucleic acid database searches using application-specific scoring matrices", Methods (1991), 3:66-70.
Tomer, "Characterization of a discontinuous epitope of the human immunodeficiency virus (HIV) core protein p24 by epitope excision and differential chemical modification followed by mass spectrometric peptide mapping analysis.", Prot. Sci. (2000), 9:487-496.
Weiner and Kotkoskie (2000) Excipient Toxicity and Safety, Marcel Dekker, Inc., New York, N.Y.
Wong et al., "Anticomplement C5 therapy with eculizumab for the treatment of paroxysmal noctumal hemoglobinuria and atypical hemolytic uremic syndrome", Translational Research, 165 (2): 306-320 (2015).
Wootton et al., "Statistics of Local Complexity in Amino Acid Sequences and Sequence Databases" Comput. Chem. (1993), 17:149-163.
Wu et al., "Humanization of a Murine Monoclonal Antibody by Simultaneous Optimization of Framework and CDR Residues", J. Mol. Biol., (1999) 294:151-162.
Wyatt "Light scattering and the absolute characterization of macromolecules", Anal. Chim. Acta (1993), 272(1):1-40.

Xu et al., "Complement C5 Gene Confers Risk for Acute Anterior", Genetics, Invest Ophthamol Vis. Sci, 56:4954-4690 (2015).
Xu et al., "Targeting the complement system for the management of relinal inflammatory and degenerative diseases", European Journal of Pharmacology 787:94-104 (2016).
Zhang et al., "PowerBLAST: A New Network BLAST Application for Interactive or Automated Sequence Analysis and Annotation", Genome Res. (1997) 7:649-656.
Zuber et al., "Use of eculizumab for atypical haemolytic uraemic syndrome and C3 glomerulopathies", Nature Reviews, Nephrology, 8:643-657 (2012).
Altschul et al., "A protein alignment scoring system sensitive at all evolutionary distances", J. Mol. Evol. (1993), 36:290-300.
Altschul et al., "Basic local alignment search tool", J. Mol. Biol. (1990), 215:403-410.
Altschul et al., "Gapped BLAST and PSI-BLAST: a new generation of protein database search programs", Nucleic Acids Res. (1997) 25:3389-3402.
Altschul et al., "Protein database searches using compositionally adjusted substitution matrices" FEBS J. (2005), 272(20):5101-5109.
Baert et al. "Influence of immunogenicity on the long-term efficacy of infliximab in Crohn's disease.", (2003) New Engl. J. Med. (2003), 348:601-608.
Beniaminovitz et al. "Prevention of Rejection in Cardiac Transplantation by Blockade of the Interleukin-2 Receptor with a Monoclonal Antibody", New Engl. J. Med. (2000), 342:613-619.
Bennett et al., "Intrathecal Pathogenic Anti-Aquaporin-4 Antibodies in Early Neuromyelitis Optica", NIH Public Access, Author Manuscript, Ann Neurol., 66(5):617-629 (2009).
Brachet et al., "Eculizumab epitope on complement C5: Progress towards a better understanding of the mechanism of action.", Mol Immunol. (2016) 77:126-131.
Casset et al., "A peptide mimetic of an anti-CD4 monoclonal antibody by rational design", Biochemical and Biophysical Research Communications, (2003) 307:198-205.
Chen et al., "Inhibition of the alternative pathway of complement activation reduces inflammation in experimental autoimmune uveoretinitis", Eur. J. Immunol, 40:2870-2881 (2010).
Chen et al., "Selection and Analysis of an Optimized Anti-VEGF Antibody: Crystal Structure of an Affinity-matured Fab in Complex with Antigen", J. Mol. Biol., (1991) 293:865-881.
Chen, et al: "Enhancement and Destruction of Antibody Function by Somatic Mutation: Unequal Occurrence is Controlled by V Gene Combinatorial Associations", The EMBO Journal, vol. 14, No. 12, pp. 2784-2794, 1995.
Chothia et al., "Canonical structures for the hypervariable regions of immunoglobulins", J Mol. Biol. (1987), 196:901-917.
Chothia et al., "Conformations of immunoglobulin hypervariable regions.", Nature (1989), 342:878-883.
Colman, P.M.: "Effects of Amino Acid Sequence Changes on Antibody-Antigen Interactions", Research in Immunology, vol. 145, pp. 33-36, 1994.
Copland et al., "Systemic and local anti-C5 therapy reduces the disease severity in experimental autoimmune uveoretinitis", Clinical &Experimental Immunology, 159:303-314 (2009).
D'Angelo, et al: "Many Routes to an Antibody Heavy-Chain CDR3: Necessary, Yet Insufficient, for Specific Binding", Frontiers in Immunology, vol. 9, Article 395, Mar. 2018; doi: 10.3389/fimmu.2018.00395, Mar. 8, 2018.
Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.
De Pascalis et al., "Grafting of 'Abbreviated' Complementarity-Determing Regions Containing Specificity-Determining Residues Essential for Ligand Contact to Engineer a Less Immunigenic Humanzied Monoclonal Anitbody", J. Immunol, (2002) 169:3076-3084.
De Vries et al., "Inhibition of complement factor C5 protects against renal ischemia-reperfusion injury: inhibition of late apoptosis and inflammation", Transplantation, 75(3):375-382 (2003).
Dembo et al., "Limit Distribution of Maximal Non-Aligned Two-Sequence Segmental Score", Ann. Prob. (1994), 22:2022-2039.

(56) References Cited

OTHER PUBLICATIONS

Engen and Smith, "Peer Reviewed: Investigating Protein Structure and Dynamics by Hydrogen Exchange MS", Anal. Chem. (2001), 73:256A-265A.
Ghosh et al. "Natalizumab for active Crohn's disease.", New Engl. J. Med. (2003), 348:24-32.
Gonnet et al. "Exhaustive matching of the entire protein sequence database.", Science (1992), 256:1443-45.
Henikoff et al., "Amino acid substitution matrices from protein blocks", Proc. Natl. Acad. Sci. USA (1992), 89:10915-10919.
Hillmen P, Hall C, Marsh JC, Elebute M, Bombara MP, Petro BE, et al. Effect of eculizumab on hemolysis and transfusion requirements in patients with paroxysmal nocturnal hemoglobinuria. The New England journal of medicine. Feb. 5, 2004;350(6):552-9. PubMed PMID: 14762182.
Hillmen P, Young NS, Schubert J, Brodsky RA, Socie G, Muus P, et al. The complement inhibitor eculizumab in paroxysmal nocturnal hemoglobinuria. The New England journal of medicine. Sep. 21, 2006;355(12):1233-43. PubMed PMID: 16990386.
International Search Report and Written Opinion for PCT/US2018/065123 issued May 31, 2019.
International Search Report for PCT/US2017/037226 (mailed Aug. 23, 2017).
Kabat et al., "Unusual distributions of amino acids in complementarity determining (hypervariable) segments of heavy and light chains of immunoglobulins and their possible roles in specifity of antibody combining sites.", J. Biol. Chem. (1977), 252:6609-6616.
Kabat, "Sequences of Proteins of Immunological Interest," National Institutes of Health, Bethesda, Md. (1991), pp. 131-286.
Kabat, "Sequences of Proteins of Immunological Interest," National Institutes of Health, Bethesda, Md. (1991), pp. 1341-1476, 1571-1599.
Kabat, "Sequences of Proteins of Immunological Interest," National Institutes of Health, Bethesda, Md. (1991), pp. 1600-1610, 2130-2163.
Kabat, "Sequences of Proteins of Immunological Interest," National Institutes of Health, Bethesda, Md. (1991), pp. 287-431.
Kabat, "Sequences of Proteins of Immunological Interest," National Institutes of Health, Bethesda, Md. (1991), pp. 432-539, 647-698.
Kabat, "Sequences of Proteins of Immunological Interest," National Institutes of Health, Bethesda, Md. (1991), pp. 699-723, 1138-1174, 1229-1341.
Kabat, "Sequences of Proteins of Immunological Interest," National Institutes of Health, Bethesda, Md. (1991), pp. xiii-44, 103-130.
Karlin et al., "Applications and statistics for multiple high-scoring segments in molecular sequences", Proc. Natl. Acad. Sci. USA (1993), 90:5873-5877.
Karlin et al., "Methods for assessing the statistical significance of molecular sequence features by using general scoring schemes", Proc. Natl. Acad. Sci. USA (1990), 87:2264-2268.
Kunik, V. et al., "Structural Consensus Among Antibodies Defines the Antigen Binding Site", PLoS Computational Biology, 8(2): e1002388 (Feb. 23, 2012).
Kurolap A, Eshach-Adiv O, Hershkovitz T, Paperna T, Mory A, Oz-Levi D, et al. Loss of CD55 in Eculizumab-Responsive Protein-Losing Enteropathy. The New England journal of medicine. Jul. 6, 2017;377(1):87-9. PubMed PMID: 28657861.
Kussie, et al: "A Single Engineered Amino Acid Substitution Changes Antibody Fine Specificity", Journal of Immunology. 152:, pp. 146-152; Year 1994.
Lipsky et al. "Infliximab and methotrexate in the treatment of rheumatoid arthritis. Anti-Tumor Necrosis Factor Trial in Rheumatoid Arthritis with Concomitant Therapy Study Group.", New Engl. J. Med. (2000), 343:1594-1602.
MacCallum et al., "Antibody-antigent Interactions: Contact Analysis and Binding Site Topography", J. Mol. Biol. (1996) 262:732-745.
Marzari R, Sblattero D, Macor P, Fischetti F, Gennaro R, Marks JD, et al. The cleavage site of C5 from man and animals as a common target for neutralizing human monoclonal antibodies: in vitro and in vivo studies. Eur J Immunol. Oct. 2002;32(10):2773-82. PubMed PMID: 12355429.
Milgrom et al. "Treatment of allergic asthma with monoclonal anti-IgE antibody. rhuMAb-E25 Study Group.", New Engl. J. Med. (1999), 341:1966-1973.
Monk et al. "Function, structure and therapeutic potential of complement C5a receptors.", Br. J. Pharmacol. (2007), 152:429-448.
Montalvo et al., "Complement Deposits on Ocular Tissues Adjacent to Sites of Inflammation", Current Eye Research, 32:917-922 (2007).
Nishimura et al., "Genetic Variants in C5 and Poor Response to Eculizumab", The New England Journal of Medicine, 370(7):632-639 (2014).
Nishimura J, Yamamoto M, Hayashi S, Ohyashiki K, Ando K, Brodsky AL, et al. Genetic variants in C5 and poor response to eculizumab. The New England journal of medicine. Feb. 13, 2014;370(7):632-9. PubMed PMID: 24521109.

\* cited by examiner ar Ratio

ANTI-C5 ANTIBODY COMBINATIONS AND USES THEREOF

This application is a divisional of U.S. patent application Ser. No. 16/217,290 filed Dec. 12, 2018, which claims the benefit of priority to U.S. Provisional Patent Application No. 62/598,023 filed Dec. 13, 2017, the disclosures of which are hereby incorporated by reference in their entireties.

FIELD

The present invention is related to combinations including antibodies and antigen-binding fragments of antibodies that specifically bind to complement factor C5, and methods of use thereof.

BACKGROUND

The complement system is a group of plasma proteins that when activated lead to target cell lysis and facilitate phagocytosis through opsonization. Complement is activated through a series of proteolytic steps by three major pathways: the classical pathway, which is typically activated by immune-complexes, the alternative pathway that can be induced by unprotected cell surfaces, and the mannose binding lectin pathway. All three pathways of complement cascade converge on proteolytic cleavage of complement component 5 (C5) protein. Cleavage of complement component 5 (C5) results in the production of fragments C5a and C5b, a process that is critical during the activation of the complement cascade. C5a can generate pleiotropic physiological responses through binding to its receptors (Monk et al. 2007, Br. J. Pharmacol. 152: 429-448). C5a is a potent proinflammatory mediator that induces chemotactic migration, enhances cell adhesion, stimulates the oxidative burst, and induces the release of various inflammatory mediators such as histamine or cytokines. C5b mediates the formation of the membrane-attack complex (MAC, or C5b-9) leading to cell lysis in the late phases of the complement dependent cytotoxicity (CDC). Further, in nucleated cells that are resistant to cytolysis by C5b-9, sublytic quantities of C5b-9 can cause cellular activation which results in cell proliferation, generation of proinflammatory mediators and production of extracellular matrix.

Monoclonal antibodies to C5 are known in the art and have been described, for example, in US patent/Publication Nos. 9206251, 9107861, 9079949, 9051365, 8999340, 8883158, 8241628, 7999081, 7432356, 7361339, 7279158, 6534058, 6355245, 6074642, 20150299305, 20160051673, 20160031975, 20150158936, 20140056888, 20130022615, 20120308559, and in WO2017218515, WO2015198243, WO2015134894, WO2015120130, EP2563813B1, EP2328616B1, and EP2061810B1.

Anti-C5 antibodies with high affinity and biological activity are known; however, an improvement in biological activity may lead to more potent therapies for subjects suffering from C5-associated diseases and disorders.

SUMMARY

Particular combinations of anti-C5 antibodies and antigen-binding fragments exhibiting surprising and unexpected levels of biological activity (e.g., reduction of red blood cell (RBC) lysis) have been identified. Combinations of anti-C5 antibodies and fragments which do not compete with one another for C5-binding lead to a reduction in RBC lysis beyond reduction associated with a single anti-C5 antibody or fragment. Compositions and therapeutic methods relating to such anti-C5 combinations are provided herein.

The present invention provides a combination (e.g., a kit) comprising a first antigen-binding protein (e.g., antibody or antigen-binding fragment thereof) that binds specifically to C5 (e.g., human C5); and one or more further antigen-binding proteins (e.g., polypeptides (e.g., coversin) or antibodies (e.g., eculizumab) or antigen-binding fragments thereof) that (i) specifically bind to C5 at an epitope which is different from that of the antigen-binding protein; and/or (ii) do not compete with the first antigen-binding protein for binding to C5. The first antigen-binding protein and the further antigen-binding protein can be co-formulated into a single pharmaceutical formulation (e.g., with a pharmaceutically acceptable carrier) or formulated into separate formulations (e.g., each with a pharmaceutically acceptable carrier). In an embodiment of the invention, the first antigen-binding protein and/or the one or more further antigen-binding protein thereof are in a pre-filled injection device (e.g., pre-filled syringe or pre-filled autoinjector) or vessel. For example, in an embodiment of the invention, the first antigen-binding protein (e.g., antibody) comprises CDR-H1, CDR-H2 and CDR-H3 of a heavy chain variable region that comprise the amino acid sequence set forth in SEQ ID NO: 19, and CDR-L1, CDR-L2 and CDR-L3 of a light chain variable region that comprise the amino acid sequence set forth in SEQ ID NO: 27. In an embodiment of the invention, the further antigen-binding protein (e.g., antibody or antigen-binding fragment) comprises (i) CDR-H1, CDR-H2 and CDR-H3 of a heavy chain variable region that comprise the amino acid sequence set forth in SEQ ID NO: 3, and CDR-L1, CDR-L2 and CDR-L3 of a light chain variable region that comprise the amino acid sequence set forth in SEQ ID NO: 11; (ii) CDR-H1, CDR-H2 and CDR-H3 of a heavy chain variable region that comprise the amino acid sequence set forth in SEQ ID NO: 35, CDR-L1, CDR-L2 and CDR-L3 of a light chain variable region that comprise the amino acid sequence set forth in SEQ ID NO: 43; (iii) CDR-H1, CDR-H2 and CDR-H3 of a heavy chain variable region that comprise the amino acid sequence set forth in SEQ ID NO: 51, CDR-L1, CDR-L2 and CDR-L3 of a light chain variable region that comprise the amino acid sequence set forth in SEQ ID NO: 59; (iv) CDR-H1, CDR-H2 and CDR-H3 of a heavy chain variable region that comprise the amino acid sequence set forth in SEQ ID NO: 67, and CDR-L1, CDR-L2 and CDR-L3 of a light chain variable region that comprise the amino acid sequence set forth in SEQ ID NO: 75; (v) CDR-H1, CDR-H2 and CDR-H3 of a heavy chain variable region that comprise the amino acid sequence set forth in SEQ ID NO: 87, and CDR-L1, CDR-L2 and CDR-L3 of a light chain variable region that comprise the amino acid sequence set forth in SEQ ID NO: 95; and/or (vi) CDR-H1, CDR-H2 and CDR-H3 of a heavy chain variable region that comprise the amino acid sequence set forth in SEQ ID NO: 103, and CDR-L1, CDR-L2 and CDR-L3 of a light chain variable region that comprise the amino acid sequence set forth in SEQ ID NO: 95. In an embodiment of the invention, the first antigen-binding protein (e.g., antibody or fragment) comprises a heavy chain variable region that comprises: a CDR-H1 that comprises the amino acid sequence set forth in SEQ ID NO: 21, a CDR-H2 that comprises the amino acid sequence set forth in SEQ ID NO: 23, and a CDR-H3 that comprises the amino acid sequence set forth in SEQ ID NO: 25, and a light chain variable region that comprises a CDR-L1 that comprises the amino acid sequence set forth in SEQ ID NO: 29), a CDR-L2 that comprises the amino acid sequence set forth in SEQ ID NO: 31, and a CDR-L3 that comprises the amino acid sequence set forth in SEQ ID NO: 33. In an embodiment of the invention, the further antigen-binding protein (e.g., antibody or fragment) comprises a heavy chain variable region that comprises (i) a CDR-H1 that comprises the amino acid sequence set forth in SEQ ID NO: 5, a CDR-H2 that comprises the amino acid sequence set forth in SEQ ID NO: 7; and a CDR-H3 that comprises the amino acid sequence set forth in SEQ ID NO: 9; and a light chain variable region that comprises a CDR-L1 that comprises the amino acid sequence set forth in SEQ ID NO: 13, a CDR-L2 that comprises the amino acid sequence set forth in SEQ ID NO: 15, and a CDR-L3 that comprises the amino acid sequence set forth in SEQ ID NO: 17; (ii) a heavy chain variable region that comprises a CDR-H1 that comprises the amino acid sequence set forth in SEQ ID NO: 37, a CDR-H2 that comprises the amino acid sequence set forth in SEQ ID NO: 39, and a CDR-H3 that comprises the amino acid sequence set forth in SEQ ID NO: 41; and a light chain variable region that comprises a CDR-L1 that comprises the amino acid sequence set forth in SEQ ID NO: 45, a CDR-L2 that comprises the amino acid sequence set forth in SEQ ID NO: 47, and a CDR-L3 that comprises the amino acid sequence set forth in SEQ ID NO: 49; (iii) a heavy chain variable region that comprises a CDR-H1 that comprises the amino acid sequence set forth in SEQ ID NO: 53, a CDR-H2 that comprises the amino acid sequence set forth in SEQ ID NO: 55, a CDR-H3 that comprises the amino acid sequence set forth in SEQ ID NO: 57; and a light chain variable region that comprises a CDR-L1 that comprises the amino acid sequence set forth in SEQ ID NO: 61, a CDR-L2 that comprises the amino acid sequence set forth in SEQ ID NO: 63, and a CDR-L3 that comprises the amino acid sequence set forth in SEQ ID NO: 65; (iv) a heavy chain variable region that comprises a CDR-H1 that comprises the amino acid sequence set forth in SEQ ID NO: 69, a CDR-H2 that comprises the amino acid sequence set forth in SEQ ID NO: 71, and a CDR-H3 that comprises the amino acid sequence set forth in SEQ ID NO: 73; and a light chain variable region that comprises a CDR-L1 that comprises the amino acid sequence set forth in SEQ ID NO: 77, a CDR-L2 that comprises the amino acid sequence set forth in SEQ ID NO: 79, and a CDR-L3 that comprises the amino acid sequence set forth in SEQ ID NO: 81; (v) a CDR-H1 that comprises the amino acid sequence set forth in SEQ ID NO: 89, a CDR-H2 that comprises the amino acid sequence set forth in SEQ ID NO: 91, a CDR-H3 that comprises the amino acid sequence set forth in SEQ ID NO: 93, a CDR-L1 that comprises the amino acid sequence set forth in SEQ ID NO: 97, a CDR-L2 that comprises the amino acid sequence set forth in SEQ ID NO: 99, a CDR-L3 L2 that comprises the amino acid sequence set forth in SEQ ID NO: 101; or (vi) a CDR-H1 that comprises the amino acid sequence set forth in SEQ ID NO: 105, a CDR-H2 that comprises the amino acid sequence set forth in SEQ ID NO: 107, a CDR-H3 that comprises the amino acid sequence set forth in SEQ ID NO: 109; a CDR-L1 that comprises the amino acid sequence set forth in SEQ ID NO: 97, a CDR-L2 that comprises the amino acid sequence set forth in SEQ ID NO: 99, and a CDR-L3 that comprises the amino acid sequence set forth in SEQ ID NO: 101. In an embodiment of the invention, the combination includes an optional further therapeutic agent. For example, the further therapeutic agent is, in an embodiment of the invention, one or more anti-C5 antibodies such as H2M11683N; H2M11686N; H4H12159P; H4H12163P; H4H12164P; H4H12166P2; H4H12166P3; H4H12166P4; H4H12166P5; H4H12166P6; H4H12166P7; H4H12166P8; H4H12166P9; H4H12166P10; H4H12167P; H4H12168P; H4H12169P; H4H12176P2; H4H12177P2; H4H12183P2; H2M11682N; H2M11684N; H2M11694N; or H2M11695N or an antibody or antigen-binding fragment comprising the $V_H$ and/or $V_L$; and/or CDR-Hs and/or CDR-Ls thereof (See International Patent Application No. PCT/US2017/037226, filed Jun. 13, 2017); or an antigen-binding fragment of any of the foregoing (which is not a first or second/further antibody or antigen-binding fragment in the combination). In an embodiment of the invention, the further therapeutic agent is an eculizumab or coversin (if not already a component of the combination), iron, antithymocyte globulin, a growth factor, anti-coagulant, a thrombin inhibitor, an anti-inflammatory drug, an antihypertensive, an immunosuppressive agent, a fibrinolytic agent, a lipid-lowering agent, an inhibitor of hydroxymethylglutaryl CoA reductase, an anti-CD20 agent, an anti-TNFα agent, an anti-seizure agent, a C3 inhibitor, an anti-thrombotic agent, warfarin, aspirin, heparin, phenindione, fondaparinux, idraparinux, argatroban, lepirudin, bivalirudin, or dabigatran, corticosteroids, and non-steroidal anti-inflammatory drugs, vincristine, cyclosporine A, methotrexate, ancrod, ε-aminocaproic acid, antiplasmin-a1, prostacyclin, defibrotide, rituximab and/or magnesium sulfate.

The present invention provides a bispecific or biparatopic antigen-binding protein (e.g., antibody or antigen-binding fragment thereof (e.g., an IgG)) comprising a first antigen-binding domain that binds to C5 (e.g., human C5) at a first epitope (e.g., one antigen-binding domain from the H4H12166P antibody) and a second antigen-binding domain that (i) specifically binds to C5 at a second epitope which is different from that of the first antigen-binding domain and/or (ii) does not compete with the first antigen-binding domain for binding to C5 (e.g., one antigen-binding domain from the eculizumab, H4H12161P, H4H12170P, H4H12171P, H4H12175P, H4H12176P2 or H4H12177P2 antibody, for example, H4H12176P2xH4H12177P2) or a pharmaceutically composition thereof comprising a pharmaceutically acceptable carrier. The present invention also provides a method for treating or preventing a C5-associated disease or disorder in a subject (e.g., a mammal such as a human) in need of such treatment or prevention or for inhibiting both the classical and alternative complement pathway (CP and AP, respectively) in a subject comprising administering (e.g., subcutaneously, intravenously, intradermally, intraperitoneally, orally, intramuscularly or intracranially) an effective amount of a combination of the present invention (and, optionally, one or more further therapeutic agents, e.g., as discussed herein) to the subject. Such a disease or disorder can be, for example, acute respiratory distress syndrome; adult respiratory distress syndrome; age-related macular degeneration; allergy; Alport's syndrome; Alzheimer's disease; asthma; asthma; atherosclerosis; atypical hemolytic uremic syndrome; autoimmune diseases; complement activation caused by balloon angioplasty; bronchoconstriction; bullous pemphigoid; burns; C3 glomerulopathy; capillary leak syndrome; chemical injury; chronic obstructive pulmonary disease; Crohn's disease; diabetes; diabetic macular edema; diabetic nephropathy; diabetic retinopathy; dyspnea; emphysema; epilepsy; fibrogenic dust diseases; frostbite; geographic atrophy; glomerulopathy; Goodpasture's Syndrome; Guillain-Barre Syndrome; complement activation caused by hemodialysis; hemodialysis complications; hemolytic anemia; hemoptysis; hereditary angioedema; hyperacute allograft rejection; hypersensitivity pneumonitis; immune complex disorders; immune complex-associated inflammation; inflammation of autoimmune diseases; inflammatory disorders; inherited CD59 deficiency; injury due to inert dusts and/or minerals; interleukin-2 induced toxicity during IL-2 therapy; lupus nephritis; membranoproliferative glomerulonephritis; membranoproliferative nephritis; mesenteric artery reperfusion after aortic reconstruction; mesenteric artery reperfusion after infectious disease; mesenteric artery reperfusion after sepsis; multiple sclerosis; myasthenia gravis; myocardial infarction; neuromyelitis optica; neuromyelitis optica; obesity; ocular angiogenesis; organic dust diseases; parasitic diseases; Parkinson's disease; paroxysmal nocturnal hemoglobinuria; pneumonia; post-ischemic reperfusion conditions; post-pump syndrome in cardiopulmonary bypass or renal bypass; progressive kidney failure; proteinuric kidney diseases; psoriasis; pulmonary embolisms and infarcts; pulmonary fibrosis; pulmonary vasculitis; renal ischemia; renal ischemia-reperfusion injury; renal transplant; rheumatoid arthritis; schizophrenia; smoke injury; stroke; stroke; systemic lupus erythematosus; systemic lupus erythematosus nephritis; thermal injury; thermal injury; traumatic brain injury; uveitis; vasculitis; and xenograft rejection. For example, in an embodiment of the invention, the method comprises administering to the subject a first antigen-binding protein that specifically binds C5 and a second antigen-binding protein that specifically binds C5; wherein the first and second antigen-binding proteins: (a) bind to distinct, non-overlapping epitopes on C5; and/or (b) do not compete with one another for binding to C5, e.g., under conditions which are discussed herein.

Kits of the present invention can also be produced by a method comprising the steps of co-packaging the first anti-C5 antigen-binding protein (e.g., antibody or fragment); and one or more of said further anti-C5 antigen-binding proteins (e.g., polypeptides, antibodies or fragments); and, optionally, one or more further therapeutic agents. A kit which is the product of such a method is also part of the present invention.

Co-formulations of the present invention can be produced by a method comprising co-formulating (e.g., mixing) said first antigen-binding protein (e.g., antibody or fragment); and one or more of said further antigen-binding proteins (e.g., polypeptides, antibodies or fragments); and, optionally, one or more further therapeutic agents; and a pharmaceutically acceptable carrier into a single pharmaceutical formulation. A co-formulation which is the product of such a method is also part of the present invention.

DETAILED DESCRIPTION

Figure 1A:
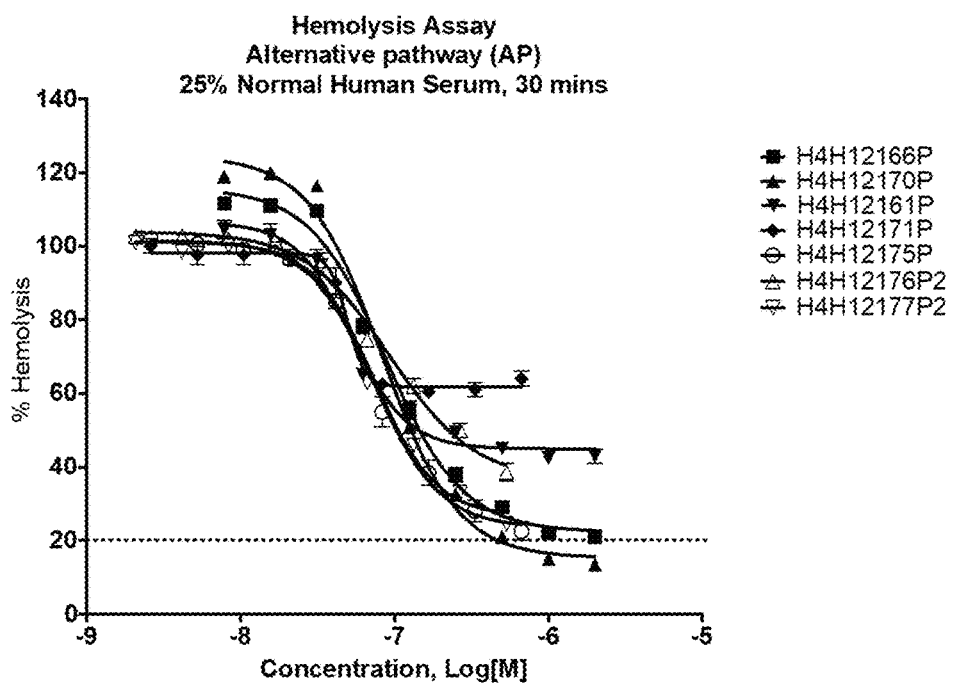
FIG. 1A is a graph showing hemolysis of red blood cells in the presence of serum and an anti-C5 antibody H4H12166P, H4H12170P, H4H12161P, H4H12171P, H4H12175P, H4H12176P2 or H4H12177P2.
Figure 1B:
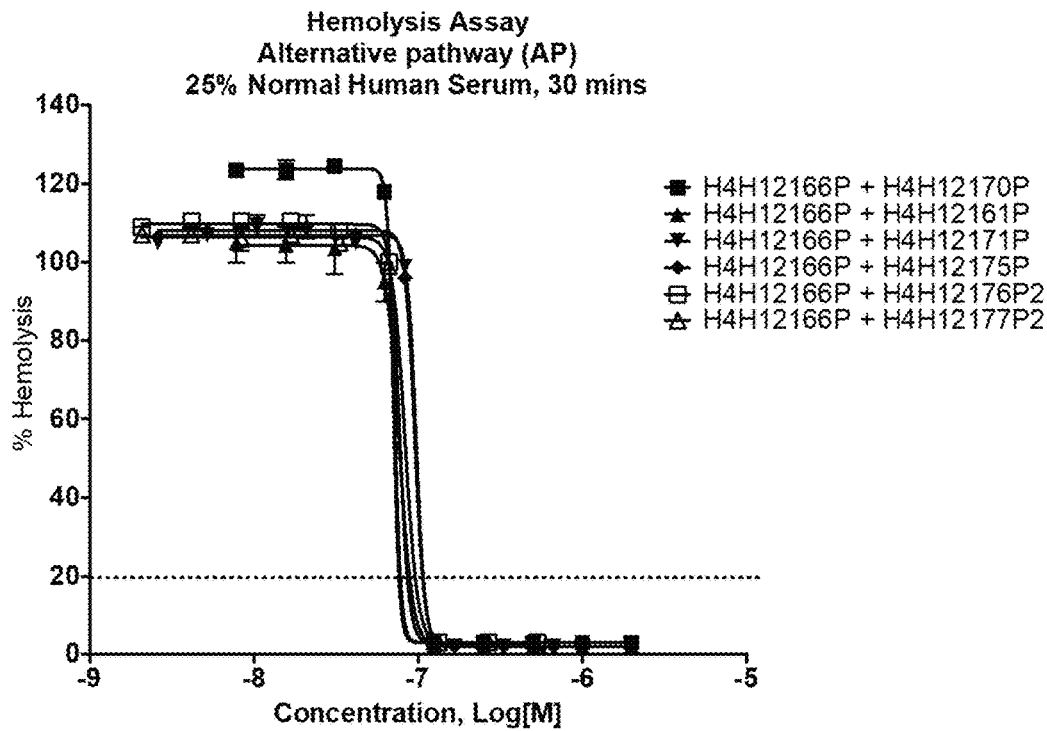
FIG. 1B is a graph showing hemolysis of red blood cells in the presence of serum and a combination of H4H12166P+H4H12170P; H4H12166P+H4H12161P; H4H12166P+H4H12171P; H4H12166P+H4H12175P; H4H12166P+H4H12176P2; or H4H12166P+H4H12177P2.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All patents, applications and publications mentioned herein are incorporated herein by reference in their entirety.

Definitions

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

Sequence identity refers to the degree to which the amino acids of two polypeptides are the same at equivalent positions when the two sequences are optimally aligned.

Sequence similarity includes identical residues and non-identical, biochemically related amino acids. Examples of groups of amino acids that have side chains with similar chemical properties include 1) aliphatic side chains: glycine, alanine, valine, leucine and isoleucine; 2) aliphatichydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

A "variant" of a polypeptide, such as an immunoglobulin chain or CDR, refers to a polypeptide comprising an amino acid sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical or similar to a referenced amino acid sequence that is set forth herein; when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment).

A "variant" of a polynucleotide refers to a polynucleotide comprising a nucleotide sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical to a referenced nucleotide sequence that is set forth herein; when the comparison is performed by a BLAST algorithm wherein the parameters of the algorithm are selected to give the largest match between the respective sequences over the entire length of the respective reference sequences (e.g., expect threshold: 10; word size: 28; max matches in a query range: 0; match/mismatch scores: 1, −2; gap costs: linear).

The following references relate to BLAST algorithms often used for sequence analysis: BLAST ALGORITHMS: Altschul et al. (2005) FEBS J. 272(20): 5101-5109; Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

As used herein, the term "subject" refers to an animal, preferably a mammal, more preferably a human, for example, in need of amelioration, prevention and/or treatment of a C5-associated disease or disorder such as atypical hemolytic uremic syndrome (aHUS) or paroxysmal nocturnal hemoglobinuria (PNH). The term includes human subjects who have or are at risk of having such a disease or disorder.

As used herein a "combination" refers to a collocation of a first component with is an anti-C5 antigen-binding protein (e.g., antibody or antigen-binding fragment) and one or more further components which is an anti-C5 antigen-binding protein (e.g., antibody, antigen-binding fragment or polypeptide) (e.g., H4H12166P and one of H4H12161P, H4H12170P, H4H12171P, H4H12175P, H4H12176P2 or H4H12177P2). Such a collocation may be in a single liquid (e.g., aqueous) or dry (e.g., lyophilized) composition, e.g., a pharmaceutical composition, that includes both components. A collocation may be a kit comprising each component in two or more separate vessels or devices. With regard to combinations used in connection with methods of treatment or prevention that are discussed herein, each component, in the combination, can be administered to a subject at a different time than when the other component is administered; for example, each administration may be given non-simultaneously (e.g., separately or sequentially) at intervals over a given period of time. Moreover, the separate components may be administered to a subject by the same or by a different route, e.g., wherein an anti-C5 antibody is administered subcutaneously and the other anti-C5 antibody is administered intravenously. In an embodiment of the invention, the components of a combination are located in a common molecule, e.g., a multispecific molecule (e.g. bispecific) that binds to C5 at multiple epitopes. For example, a combination of two anti-C5 antibodies or antigen-binding fragments includes a bispecific or biparatopic antibody or fragment having a first antigen-binding domain that binds to a first epitope on C5 and a second antigen-binding domain that binds to a second, different epitope on C5 and/or which does not compete for binding to C5 with the first antigen-binding domain (e.g., as discussed further herein).

C5

The present invention relates to combinations including antigen-binding proteins (e.g., antibodies and antigen-binding fragments) that bind to C5 ("complement component 5" or "complement factor 5"), for example, human C5 (e.g., H4H12166P and one of H4H12161P, H4H12170P, H4H12171P, H4H12175P, H4H12176P2 or H4H12177P2).

The C5 gene encodes a component of the complement system, a part of the innate immune system that plays an important role in inflammation, host homeostasis, and host defense against pathogens. The C5 gene product is proteolytically processed to generate multiple protein products, including the C5 alpha chain, C5 beta chain, C5a anaphylatoxin and C5b. The C5 protein includes the C5 alpha and beta chains which are linked by a disulfide bridge.

The amino acid sequence of full-length C5 protein is exemplified by the amino acid sequence provided in GenBank as accession number NP_001726.2 (SEQ ID NO: 1). The term "C5" includes recombinant C5 protein or a fragment thereof (e.g. a mature fragment lacking the N-terminal signal peptide). The term also encompasses C5 protein or a fragment thereof coupled to, for example, histidine tag, mouse or human Fc, or a signal sequence such as ROR1. The term also includes protein variants that comprise a histidine tag at the C-terminal, coupled to amino acid residues 19-1676 of full-length C5 protein with a R885H change or a R885C change. In an embodiment of the invention, human C5 comprises the amino acid sequence set forth in SEQ ID NO: 1.

Anti-C5 Antibodies, Fragments and Polypeptides

The present invention provides combinations comprising a first antigen-binding protein (e.g., an antibody or antigen-binding fragment thereof) that binds specifically to C5 and one or more further antigen-binding proteins (e.g., polypeptides or antibodies or antigen-binding fragments thereof) that (i) specifically bind to C5 at an epitope which is different from that of the first antigen-binding protein; and/or (ii) do not compete with the first antigen-binding protein for binding to C5 (e.g., H4H12166P and one of H4H12161P, H4H12170P, H4H12171P, H4H12175P, H4H12176P2 or H4H12177P2).

An anti-C5 "antigen-binding protein" is a polypeptide or complex of more than one polypeptide (e.g., a tetrameric IgG antibody) that binds specifically to C5 polypeptide, for example, an anti-C5 antibody or antigen-binding fragment.

For example, the present invention includes combinations comprising antibody H4H12166P (or an antigen-binding fragment thereof) and any one or more antibodies (or antigen-binding fragments thereof)) selected from H4H12161P, H4H12170P, H4H12171P, H4H12171P, H4H12175P, H4H12176P2 and H4H12177P2; or Eculizumab (sold as "Soliris"); or the polypeptide *Ornithodoros moubata* OmCl (or a variant thereof) or EV576 (coversin). See International patent application publication no. WO2004106369 or U.S. patent application publication no. US20170065677 or WO2007028968.

The term "antibody", as used herein, refers to antigen-binding proteins which are immunoglobulin molecules comprising four polypeptide chains, two heavy (H) chains and two light (L) chains inter-connected by disulfide bonds (i.e., "full antibody molecules"), as well as multimers thereof (e.g., IgM) or antigen-binding fragments thereof. Each heavy chain includes a heavy chain variable region ("HCVR" or "$V_H$") and a heavy chain constant region (comprising domains $C_{H1}$, $C_{H2}$ and $C_{H3}$). Each light chain includes a light chain variable region ("LCVR" or "$V_L$") and a light chain constant region ($C_L$). The $V_H$ and $V_L$ regions can be further subdivided into regions of hypervariability, termed "complementarity determining regions" (CDR), interspersed with regions that are more conserved, termed framework regions (FR). Each $V_H$ and $V_L$ is composed of three CDRs and four FRs, arranged, from amino-terminus to carboxy-terminus, in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified.

The present invention includes combinations which are multispecific (e.g., bispecific) antigen-binding proteins (e.g., antibodies and antigen-binding fragments thereof) which comprise a first antigen-binding domain that binds to C5 at a first epitope and a second antigen-binding domain that (i) specifically binds to C5 at a second epitope which is different from that of the first antigen-binding domain; and/or (ii) do not compete with the first antigen-binding domain for binding to C5 (or would not compete if the first antigen-binding domain and second antigen-binding domain were in separate monospecific (e.g., bivalent IgG) proteins (e.g., antibodies) that were tested for competition). A bispecific antigen-binding protein (e.g., antibody) may also be called biparatopic insofar as the molecule binds to two epitopes within the same antigen (C5). For example, in an embodiment of the invention, the first antigen-binding domain comprises the heavy and light chain CDRs (CDR-H1, CDR-H2, CDR-H3, CDR-L1, CDR-L2 and CDR-L3) or the $V_H$ and $V_L$ or heavy and light chain of H4H12166P; and the second antigen-binding domain comprises the heavy and light chain CDRs (CDR-H1, CDR-H2, CDR-H3, CDR-L1, CDR-L2 and CDR-L3) or the $V_H$ and $V_L$ or heavy and light chain of H4H12161P, H4H12170P, H4H12171P, H4H12175P, H4H12176P2 or H4H12177P2. For example, in an embodiment of the invention, the biparatopic antigen-binding protein (e.g., antibody or antigen-binding fragment) is in a bispecific IgG format (e.g., IgG1, IgG2, IgG3 or IgG4 (e.g., having a Ser228Pro mutation)) that it a tetramer comprising two heavy chain/light chain pairs. In an embodiment of the invention, the otherwise biparatopic antigen-binding protein (e.g., antibody or fragment) is appended with one or more additional antigen-binding immunoglobulins (e.g., an additional C5-binding immunoglobulin) or an additional polypeptide (e.g., coversin). The present invention also provides an anti-C5 antigen-binding protein (e.g., antibody or antigen-binding fragment thereof) that is linked with a polypeptide (e.g., coversin) that binds to C5 at a different epitope than that of the antigen-binding protein (e.g., antibody or fragment) and/or which does not compete with the antigen-binding protein (e.g., antibody or fragment) for binding to C5. In an embodiment of the invention, the bispecific antigen-binding protein is a F(ab')$_2$ of a full bispecific antibody (e.g., IgG antibody), e.g., the product of a pepsin cleavage of a bispecific IgG antibody. In an embodiment of the invention, the bispecific antigen-binding protein is a bivalent/bispecific scFv that comprises a $V_L$ and $V_H$ that binds to a first C5 epitope linked, e.g., via linker (e.g., peptide linker), to a second $V_H$ and $V_L$ that binds to a second C5 epitope.

Antibodies and antigen-binding fragments discussed herein may be assigned to different classes depending on the amino acid sequences of the constant domain of their heavy chains. There are at least five major classes of immunoglobulins: IgA, IgD, IgE, IgG and IgM, and several of these may be further divided into subclasses (isotypes), e.g. IgG1, IgG2, IgG3 and IgG4; IgA1 and IgA2. A human heavy chain constant region can be gamma-4 (IgG4) with a Ser228Pro mutation (Schuurman, J et al., Mol. Immunol. 38: 1-8, 2001). An antibody or antigen-binding fragment can comprise a light chain constant region such as a human light chain constant region (e.g., lambda or kappa human light chain region). The anti-C5 antibody and antigen-binding fragment $V_H$ chains discussed herein may be linked to any of the heavy constant chains discussed herein. The anti-C5 antibody and antigen-binding fragment $V_L$ chains discussed herein may be linked to any of the light constant chains discussed herein.

Antibodies and antigen-binding fragments discussed herein may comprise a $V_H$ and/or $V_L$ set forth herein and a modified Fc. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification. In an embodiment of the invention, a combination comprises one or more anti-C5 antibodies or antigen-binding fragments comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations and other mutations within the antibody variable domains disclosed herein, are contemplated within the scope of the present invention.

The identification of CDRs within an immunoglobulin chain is well known in the art. The assignment of amino acids to each domain is, in an embodiment of the invention, in accordance with the definitions of Sequences of Proteins of Immunological Interest, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342:878-883. Thus, when referring to CDRs in a given immunoglobulin chain, said CDRs may, in an embodiment of the invention, be identified using any of the conventions and methods cited above.

The present invention relates to anti-C5 antibodies and antigen-binding fragments and polypeptides comprising sequences that are specifically set forth herein as well as variants thereof. A variant of an anti-C5 antibody or fragment disclosed herein may comprise one or more (e.g., 1, 2, 3, 4, 5, 6, 7, 8, 9 or 10) amino acid substitutions, insertions and/or deletions in the framework and/or CDR regions of the heavy and/or light chain variable domains (e.g., in any one or more of CDR-H1, CDR-H2, CDR-H3, CDR-L1, CDR-L2 and/or CDR-L3) as compared to the corresponding specific sequences set forth herein. In an embodiment of the invention, a variant of an anti-C5 antibody or fragment has one or more conservative substitutions; for example, having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences specifically disclosed herein. In an embodiment of the invention, an anti-C5 antibody, fragment or polypeptide is a variant comprising a polypeptide (e.g., an immunoglobulin heavy and/or light chain variable region) amino acid sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical or similar to a referenced amino acid sequence that is set forth herein; when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment). In an embodiment of the invention, such a variant retains the ability to bind to C5.

In an embodiment of the invention, the anti-C5 antibody or antigen-binding fragment comprises a heavy chain comprising an amino acid that is at least 70% identical to the amino acid sequence set forth in SEQ ID NO: 3, 19, 35, 51, 67, 82, 84, 87 or 103 and/or a light chain comprising an amino acid that is at least 70% identical to the amino acid sequence set forth in SEQ ID NO: 11, 27, 43, 59, 75, 83, 85 or 95. For example, in an embodiment of the invention, while the overall sequence identity of an immunoglobulin chain is less than 100% relative to that of a reference immunoglobulin chain amino acid sequence, the immunoglobulin chain comprises CDR1, CDR2 and CDR3 which are 100% identical to that of the CDRs in the reference immunoglobulin chain.

The present invention also relates to combinations including human anti-C5 antigen-binding proteins (e.g., antibodies and antigen-binding fragments thereof). The term "human antibody", as used herein, includes antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a nonhuman mammal, or in cells of a non-human mammal. The term is not intended to include antibodies isolated from or generated in a human subject. Methods for generating human antibodies in transgenic mice are known in the art. Any such known methods can be used in the context of the present invention to make human antibodies that specifically bind to C5 protein. Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to C5 can be initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody can be isolated and operably linked to DNA encoding the human heavy and light chain constant regions. The DNA can then be expressed in a cell capable of expressing the fully human antibody. Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

The present invention also relates to combinations including recombinant anti-C5 antigen-binding proteins (e.g., antibodies and antigen-binding fragments thereof). The term "recombinant", as used herein, refers to antibodies or antigen-binding fragments thereof of the invention created, expressed, isolated or obtained by technologies or methods known in the art as recombinant DNA technology which include, e.g., DNA splicing and transgenic expression. The term refers to antigen-binding proteins, such as antibodies, expressed in a non-human mammal (including transgenic non-human mammals, e.g., transgenic mice), or a cell (e.g., CHO cells) expression system or isolated from a recombinant combinatorial human antibody library. See e.g., U.S. Pat. Nos. 4,816,567; 6,331,415 and 7,923,221.

The present invention also relates to combinations including blocking or neutralizing anti-C5 antigen-binding proteins (e.g., antibodies and antigen-binding fragments thereof and polypeptides). A "blocking" or "neutralizing" antigen-binding protein, e.g., antibody, fragment or polypeptide, as used herein (or an antibody, fragment or polypeptide that "neutralizes C5 activity" or an "antagonist" antibody, fragment or polypeptide), is intended to refer to a protein whose binding to C5 results in inhibition of at least one biological activity of C5. For example, an antibody of the invention may prevent or block complement-mediated hemolysis (e.g., of a red blood cell), e.g., by the classical pathway or the alternative pathway.

The present invention also relates to combinations including anti-C5 antigen-binding proteins which are antigen-binding fragments of an antibody. The terms "antigen-binding portion" of an antibody, "antigen-binding fragment" of an antibody, and the like, as used herein, include a naturally occurring, enzymatically obtainable, synthetic, or genetically engineered polypeptide or glycoprotein, other than a full antibody, that specifically binds an antigen to form a complex. The terms "antigen-binding fragment" of an antibody, or "antibody fragment", as used herein, refers to one or more fragments of an antibody that retain the ability to bind to C5 protein. Antigen-binding fragments include (i) Fab fragments; (ii) F(ab')$_2$ fragments; (iii) Fd fragments; (iv) Fv fragments; (v) single chain Fv (scFv) molecules; (vi) dAb fragments; and (vii) minimal recognition units including the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein. In certain embodiments, the term "antigen-binding fragment" refers to a polypeptide fragment of a multi-specific antigen-binding molecule. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

In an embodiment of the invention, an antigen-binding fragment of an antibody comprises at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody includes at least one variable domain covalently linked to at least one constant domain. Non-limiting, exemplary configurations of variable and constant domains that may be found within an antigen-binding fragment of an antibody of the present invention include:
(i) $V_H$-$C_{H1}$;
(ii) $V_H$-$C_{H2}$;
(iii) $V_H$-$C_{H3}$;
(iv) $V_H$-$C_{H1}$-$C_{H2}$;
(v) $V_H$-$C_{H1}$-$C_{H2}$-$C_{H3}$;
(vi) $V_H$-$C_{H2}$-$C_{H3}$;
(vii) $V_H$-$C_L$;
(viii) $V_L$-$C_{H1}$;
(ix) $V_L$-$C_{H2}$;
(x) $V_L$-$C_{H3}$;
(xi) $V_L$-$C_{H1}$-$C_{H2}$;
(xii) $V_L$-$C_{H1}$-$C_{H2}$-$C_{H3}$;
(xiii) $V_L$-$C_{H2}$-$C_{H3}$; and
(xiv) $V_L$-$C_L$.

In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The present invention also relates to combinations including multispecific (e.g., bispecific) antigen-binding proteins (e.g., antibodies, antigen-binding fragments or polypeptides). The term multispecific includes the term multiparatopic (and biparatopic). Multiparatopic molecules bind to multiple epitopes within the same antigen. A multispecific antigen-binding fragment of an antibody will typically comprise at least two different variable domains, wherein each variable domain is capable of specifically binding to a different antigen or to a different epitope on the same antigen (e.g., biparatopic). A biparatopic IgG antibody comprises two different heavy/light chain pairs that bind to two different epitopes within C5.

"Isolated" antigen-binding proteins, e.g., antibodies or antigen-binding fragments thereof, polypeptides, polynucleotides and vectors, are at least partially free of other biological molecules from the cells or cell culture from which they are produced. Such biological molecules include nucleic acids, proteins, other antibodies or antigen-binding fragments, lipids, carbohydrates, or other material such as cellular debris and growth medium. Isolated antibodies or antigen-binding fragments thereof, polypeptides, polynucleotides and vectors may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or antigen-binding fragments thereof, polypeptides, polynucleotides and/or vectors.

The term "specifically binds," or "binds specifically to", or the like, means that an antigen-binding protein, e.g., antibody or antigen-binding fragment thereof, forms a complex with an antigen that is relatively stable under physiologic conditions. Specific binding can be characterized by an equilibrium dissociation constant of at least about $1\times10^{-8}$ M or a lower number (e.g., a smaller $K_D$ denotes a tighter binding), for example, at least $10^{-9}$ M or $10^{-10}$ M, or at least $1.29\times10^{-10}$ M for binding to C5 at 25° C. as measured by SPR or at least $2.62\times10^{-10}$ M for binding to C5 at 37° C. as measured by SPR.

The term "anti-C5" refers to an antigen-binding protein, e.g., an antibody, antigen-binding fragment, polypeptide or other molecule, that specifically binds to C5 polypeptide or an immunogenic fragment thereof.

Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to C5.

In an embodiment of the invention, antigen-binding proteins, e.g., an antibody or antibody fragment of the invention, may be conjugated to a moiety such a ligand or a therapeutic moiety ("immunoconjugate"), a second anti-C5 antibody, or any other therapeutic moiety useful for treating a C5-associated disease or disorder. In an embodiment of the invention, an anti-C5 antigen-binding protein, e.g., antibody or antigen-binding fragment thereof as set forth herein, is conjugated to coversin polypeptide.

A selection of anti-C5 antibodies and antigen-binding fragments, wherein each of which do not compete with H4H12166P for C5 binding, includes H4H12161P, H4H12170P, H4H12171P, H4H12175P, H4H12176P2 and H4H12177P2. The present invention includes combinations including any two or more of these antibodies or antigen-binding fragments thereof. As discussed above, a combination may be a multispecific (e.g., bispecific) antibody comprising a heavy and light chain of one such antibody and the heavy and light chain of another such antibody. For example, the scope of the present invention includes a bispecific antibody or antigen-binding fragment thereof comprising a combination of heavy chain immunoglobulin and light chain immunoglobulin taken from any of H4H12161P, H4H12166P, H4H12170P, H4H12171P, H4H12175P, H4H12176P2 and H4H12177P2 to form an antigen-binding domain and a combination of a different heavy chain immunoglobulin and a different light chain immunoglobulin taken from any of H4H12161P, H4H12166P, H4H12170P, H4H12171P, H4H12175P, H4H12176P2 and H4H12177P2 to form a different antigen-binding domain. A summary of light and heavy chain combinations making up some bispecific antibodies and antigen-binding fragments of the present invention is set forth below in Table A. An "X" indicates a bispecific antibody including an antigen-binding domain from the antibody on the horizontal axis and an antigen-binding domain from an antibody on the vertical axis (e.g., a H4H12176P2×H4H12177P2 bispecific antibody). As used herein bispecific antibodies may be referred to as "A×B" wherein A is the antigen-binding domain of a first antibody and B is the antigen-binding domain from a second, different antibody.

TABLE A

Exemplary bispecific antibody chain combinations*

|  | H4H12161P | H4H12166P | H4H12170P | H4H12171P | H4H12175P | H4H12176P2 | H4H12177P2 |
|---|---|---|---|---|---|---|---|
| H4H12161P |  |  |  |  |  |  |  |
| H4H12166P | x |  |  |  |  |  |  |
| H4H12170P | x | x |  |  |  |  |  |
| H4H12171P | x | x | x |  |  |  |  |
| H4H12175P | x | x | x | x |  |  |  |
| H4H12176P2 | x | x | x | x | x |  |  |
| H4H12177P2 | x | x | x | x |  | x |  |

*Combinations comprising the two individual antigen-binding proteins indicated in Table A with an "x" are also part of the present invention.

"H4H12161P", "H4H12166P", "H4H12170P", "H4H12171P", "H4H12175P", "H4H12176P2" and "H4H12177P2", for example, refer to antibodies and antigen-binding fragments thereof (or, in the context of a bispecific antibody or antigen-binding fragment, to an antigen-binding domain thereof) that comprise the heavy chain or $V_H$ (or a variant thereof) and light chain or $V_L$ (or a variant thereof) as set forth below, or that comprise a $V_H$ that comprises the CDRs thereof (CDR-H1 (or a variant thereof), CDR-H2 (or a variant thereof) and CDR-H3 (or a variant thereof)) and a $V_L$ that comprises the CDRs thereof (CDR-L1 (or a variant thereof), CDR-L2 (or a variant thereof) and CDR-L3 (or a variant thereof)), e.g., wherein the immunoglobulin chains, variable regions and/or CDRs comprise the specific amino acid sequences described below. Such nomenclature may be used herein to refer to other antibodies and antigen binding fragments and antigen-binding domains thereof disclosed in WO2017/218515.

The present invention, thus, includes, but is not limited to, multispecific (e.g., bispecific or biparatopic) antibodies and antigen-binding fragments thereof including "H4H12161PxH4H12177P2"; "H4H12166PxH4H12177P2"; "H4H12170PxH4H12177P2"; "H4H12171PxH4H12177P2"; "H4H12176P2xH4H12177P2"; "H4H12176P2xH4H12161P"; "H4H12176P2xH4H12166P"; "H4H12176P2xH4H12170P"; "H4H12176P2xH4H12171P"; "H4H12176P2xH4H12175P"; "H4H12175PxH4H12161P"; "H4H12175PxH4H12166P"; "H4H12175PxH4H12170P"; "H4H12175PxH4H12171P"; "H4H12171PxH4H12161P"; "H4H12171PxH4H12166P"; "H4H12171PxH4H12170P"; "H4H12170PxH4H12161P"; "H4H12170PxH4H12166P"; and "H4H12166PxH4H12161P".

For example, the multispecific (e.g., bispecific or biparatopic) antibody or antigen-binding fragment, H4H12176P2xH4H12177P2, comprises:
a first antigen binding domain comprising:
(1)
a heavy chain immunoglobulin or variable region thereof that comprises CDR-H1, CDR-H2 and CDR-H3 of a heavy chain immunoglobulin or variable region thereof that comprises the amino acid sequence set forth in SEQ ID NO: 87; or a variant thereof; and
a light chain immunoglobulin or variable region thereof that comprises CDR-L1, CDR-L2 and CDR-L3 of a light chain immunoglobulin or variable region thereof that comprises the amino acid sequence set forth in SEQ ID NO: 95 or a variant thereof; and
a second antigen binding domain comprising
a heavy chain immunoglobulin or variable region thereof that comprises CDR-H1, CDR-H2 and CDR-H3 of a heavy chain immunoglobulin or variable region thereof that comprises the amino acid sequence set forth in SEQ ID NO: 103; or a variant thereof; and
a light chain immunoglobulin or variable region thereof that comprises CDR-L1, CDR-L2 and CDR-L3 of a light chain immunoglobulin or variable region thereof that comprises the amino acid sequence set forth in SEQ ID NO: 95 or a variant thereof;
or
(2)
a first antigen binding domain comprising:
a heavy chain variable region comprising a CDR-H1 comprising the amino acid sequence set forth in SEQ ID NO: 89;
a CDR-H2 comprising the amino acid sequence set forth in SEQ ID NO: 91; and
a CDR-H3 comprising the amino acid sequence set forth in SEQ ID NO: 93;
and a light chain variable region comprising
a CDR-L1 comprising the amino acid sequence set forth in SEQ ID NO: 97;
a CDR-L2 comprising the amino acid sequence set forth in SEQ ID NO: 99; and
a CDR-L3 comprising the amino acid sequence set forth in SEQ ID NO: 101;
and a second antigen binding domain comprising:
a heavy chain variable region comprising
a CDR-H1 comprising the amino acid sequence set forth in SEQ ID NO: 105;
a CDR-H2 comprising the amino acid sequence set forth in SEQ ID NO: 107; and
a CDR-H3 comprising the amino acid sequence set forth in SEQ ID NO: 109;
and a light chain variable region comprising
a CDR-L1 comprising the amino acid sequence set forth in SEQ ID NO: 97;
a CDR-L2 comprising the amino acid sequence set forth in SEQ ID NO: 99; and
a CDR-L3 comprising the amino acid sequence set forth in SEQ ID NO: 101;
or
(3)
a first antigen binding domain comprising:
(a) a heavy chain immunoglobulin or variable region thereof comprising the CDR-H1, CDR-H2 and CDR-H3 of a heavy chain immunoglobulin or variable region thereof comprising an amino acid sequence set forth in SEQ ID NO: 87 and at least 90% amino acid sequence identity to the amino acid sequence set forth in SEQ ID NO: 87; and/or
(b) an light chain immunoglobulin or variable region thereof comprising the CDR-L1, CDR-L2 and CDR-L3 of a light chain immunoglobulin or variable region thereof comprising an amino acid sequence set forth in SEQ ID NO: 95 and at least 90% amino acid sequence identity to the amino acid sequence set forth in SEQ ID NO: 95.
a second antigen binding domain comprising:
(a) a heavy chain immunoglobulin or variable region thereof comprising the CDR-H1, CDR-H2 and CDR-H3 of a heavy chain immunoglobulin or variable region thereof comprising an amino acid sequence set forth in SEQ ID NO: 103 and at least 90% amino acid sequence identity to the amino acid sequence set forth in SEQ ID NO: 103; and/or
(b) an light chain immunoglobulin or variable region thereof comprising the CDR-L1, CDR-L2 and CDR-L3 of a light chain immunoglobulin or variable region thereof comprising an amino acid sequence set forth in SEQ ID NO: 95 and at least 90% amino acid sequence identity to the amino acid sequence set forth in SEQ ID NO: 95;
or
(4)
a first antigen binding domain comprising:
a heavy chain immunoglobulin or variable region thereof comprising an amino acid sequence having at least 90% (e.g., 100%) amino acid sequence identity to the amino acid sequence set forth in SEQ ID NO: 87; and/or
a light chain immunoglobulin or variable region thereof comprising an amino acid sequence having at least 90% (e.g., 100%)amino acid sequence identity to the amino acid sequence set forth in SEQ ID NO: 95; and
a second antigen binding domain comprising:
a heavy chain immunoglobulin or variable region thereof comprising an amino acid sequence having at least 90%

(e.g., 100%)amino acid sequence identity to the amino acid sequence set forth in SEQ ID NO: 103; and/or
a light chain immunoglobulin or variable region thereof comprising an amino acid sequence having at least 90% (e.g., 100%)amino acid sequence identity to the amino acid sequence set forth in SEQ ID NO: 95.

*Analogous multispecific antigen-binding protein embodiments comprising other combinations of immunoglobulin chains which are set forth herein are also part of the present invention.

Multispecific (e.g., bispecific) antigen-binding proteins of the present invention include two or more different antigen-binding domain which are selected from any of the anti-C5 antibodies set forth in WO2017/218515, e.g., H2M11683N; H2M11686N; H4H12159P; H4H12161P; H4H12163P; H4H12164P; H4H12166P; H4H12166P2; H4H12166P3; H4H12166P4; H4H12166P5; H4H12166P6; H4H12166P7; H4H12166P8; H4H12166P9; H4H12166P10; H4H12167P; H4H12168P; H4H12169P; H4H12170P; H4H12171P; H4H12175P; H4H12176P2; H4H12177P2; H4H12183P2; H2M11682N; H2M11684N; H2M11694N or H2M11695N—in an embodiment of the invention, the antigen binding domains are taken from non-competing antibodies in this list; in an embodiment of the invention, the antigen binding domains are taken from competing antibodies in this list. See Table 1 herein. WO2017/218515 is herein incorporated by reference in its entirety. In an embodiment of the invention, an antigen-binding domain is taken from eculizumab or ALXN1210 (Ravulizumab).

```
H4H12161P
V_H domain (DNA):
GAGGTGCAGCTGGTGGAGTCTGGGGGAGACTTGGTCCAGC

CTGGAGGGTCCCTGAGACTCTCCTGTGCAGCCTCTGGATT

CACCTTCAGTGACCACTATATGGACTGGGTCCGCCAGGCT

CCAGGGAAGGGGCTGGACTGGATTGGCCGTATTAGAAACA

AAGCTAACGCTTATAACACAGAATACGCCGCGTCTGTGAG

AGGCAGATTCACCATCTCAAGAGATGATTCACAGAATTTA

CTGTATCTGCAAATGAACAGCCTGAAAACCGATGACACGG

CCGTATATTATTGTGTTAGAGTCTGGAACTACGCCTACTT

CGCTATGGACGTCTGGGGCCAAGGGACCACGGTCACCGTC

TCCTCA
(SEQ ID NO: 2)

V_H domain (Polypeptide):
EVQLVESGGDLVQPGGSLRLSCAASGFTFSDHYMDWVRQA

PGKGLDWIGRIRNKANAYNTEYAASVRGRFTISRDDSQNL

LYLQMNSLKTDDTAVYYCVRVWNYAYFAMDVWGQGTTVTV

SS
(SEQ ID NO: 3)

CDR-H1 (DNA):
GGA TTC ACC TTC AGT GAC CAC TAT
(SEQ ID NO: 4)

CDR-H1 (Polypeptide):
G  F  T  F  S  D  H  Y
(SEQ ID NO: 5 (or a variant thereof having
1, 2, 3 or 4 point mutations and/or point
deletions))

CDR-H2 (DNA):
ATT AGA AAC AAA GCT AAC GCT TAT AAC ACA
(SEQ ID NO: 6)

CDR-H2 (Polypeptide):
I  R  N  K  A  N  A  Y  N  T
(SEQ ID NO: 7 (or a variant thereof having
1, 2, 3 or 4 point mutations and/or point
deletions))

CDR-H3 (DNA):
GTT AGA GTC TGG AAC TAC GCC TAC TTC GCT ATG
GAC GTC
(SEQ ID NO: 8)

CDR-H3 (Polypeptide):
V  R  V  W  N  Y  A  Y  F  A
M  D  V
(SEQ ID NO: 9 (or a variant thereof having
1, 2, 3 or 4 point mutations and/or point
deletions))

V_L domain (DNA):
GACATCCAGATGACCCAGTCTCCATCCTCCCTATCTGCAT

CTGTGGGAGACAGAGTCACCATCACTTGCCGGTCAAGTCA

GAACATTGGAATCTTTTTAAACTGGTATCAACAAAACCA

GGGGAAGCCCCTAACCTCCTGATCTCCGCTGCATCCAGTT

TACACAGTGGGGTCCCTTCAAGGTTCAGTGGCAGTGGGTC

TGGGACAGATTTCACTCTCACCATCGGCAGTCTGCAGCCT

GAAGATTTTGCGACTTACTACTGTCAACAGACGTACAATA

CCATATTCACTTTCGGCCCTGGGACCAAAGTGGATATCAA

A
(SEQ ID NO: 10)

V_L domain (Polypeptide):
DIQMTQSPSSLSASVGDRVTITCRSSQNIGIFLNWYQQKP

GEAPNLLISAASSLHSGVPSRFSGSGSGTDFTLTIGSLQP

EDFATYYCQQTYNTIFTFGPGTKVDIK
(SEQ ID NO: 11)

CDR-L1 (DNA):
CAG AAC ATT GGA ATC TTT
(SEQ ID NO: 12)

CDR-L1 (Polypeptide):
Q  N  I  G  I  F
(SEQ ID NO: 13 (or a variant thereof having
1, 2, 3 or 4 point mutations and/or point
deletions))

CDR-L2 (DNA):
GCT GCA TCC
(SEQ ID NO: 14)

CDR-L2 (Polypeptide):
A  A  S
(SEQ ID NO: 15 (or a variant thereof having
a point mutation or point deletion))

CDR-L3 (DNA):
CAA CAG ACG TAC AAT ACC ATA TTC ACT
(SEQ ID NO: 16)

CDR-L3 (Polypeptide):
Q  Q  T  Y  N  T  I  F  T
(SEQ ID NO: 17 (or a variant thereof having
1, 2, 3 or 4 point mutations and/or point
deletions))
```

H4H12166P
V_H domain (DNA):
CAGGTGCAGCTGCAGGAGTCGGGCCCAGGACTGGTGAAGC

CTTCGGAGACCCTGTCCCTCACCTGCACTGTCTCTGGTGA

CTCCGTCAGTAGTTCCTACTGGACCTGGATCCGGCAGCCC

CCAGGGAAGGGACTGGAGTGGATTGGCTATATCTATTACA

GTGGGAGTTCCAACTACAACCCCTCCCTCAAGAGTCGAGC

CACCATTTCAGTAGACACGTCCAAGAACCAGTTCTCCCTG

AAGCTGAGTTCTGTGACCGCTGCGGACACGGCCGTATATT

ACTGTGCGAGAGAAGGGAACGTGGATACAACTATGATATT

TGACTACTGGGGCCAGGGAACCCTGGTCACCGTCTCCTCA
(SEQ ID NO: 18)

V_H domain (Polypeptide):
QVQLQESGPGLVKPSETLSLTCTVSGDSVSSSYWTWIRQP

PGKGLEWIGYIYYSGSSNYNPSLKSRATISVDTSKNQFSL

KLSSVTAADTAVYYCAREGNVDTTMIFDYWGQGTLVTVSS
(SEQ ID NO: 19)

Heavy immunoglobulin chain hIgG4
(M428L N4345)
QVQLQESGPGLVKPSETLSLTCTVSGDSVSSSYWTWIRQP

PGKGLEWIGYIYYSGSSNYNPSLKSRATISVDTSKNQFSL

KLSSVTAADTAVYYCAREGNVDTTMIFDYWGQGTLVTVSS

ASTKGPSVFPLAPCSRSTSESTAALGCLVKDYFPEPVTVS

WNSGALTSGVHTFPAVLQSSGLYSLSSVVTVPSSSLGTKT

YTCNVDHKPSNTKVDKRVESKYGPPCPPCPAPEFLGGPSV

FLFPPKPKDTLMISRTPEVTCVVVDVSQEDPEVQFNWYVD

GVEVHNAKTKPREEQFNSTYRVVSVLTVLHQDWLNGKEYK

CKVSNKGLPSSIEKTISKAKGQPREPQVYTLPPSQEEMTK

NQVSLTCLVKGFYPSDIAVEWESNGQPENNYKTTPPVLDS

DGSFFLYSRLTVDKSRWQEGNVFSCSVLHEALHSHYTQKS

LSLSLGK
(SEQ ID NO: 82)

CDR-H1 (DNA):
GGT GAC TCC GTC AGT AGT TCC TAC
(SEQ ID NO: 20)

CDR-H1 (Polypeptide):
G D S V S S S Y
(SEQ ID NO: 21 (or a variant thereof having
1, 2, 3 or 4 point mutations and/or point
deletions))

CDR-H2 (DNA):
ATC TAT TAC AGT GGG AGT TCC
(SEQ ID NO: 22)

CDR-H2 (Polypeptide):
I Y Y S G S S
(SEQ ID NO: 23 (or a variant thereof having
1, 2, 3 or 4 point mutations and/or point
deletions))

CDR-H3 (DNA):
GCG AGA GAA GGG AAC GTG GAT ACA ACT ATG
ATA TTT GAC TAC
(SEQ ID NO: 24)

CDR-H3 (Polypeptide):
A R E G N V D T T
M I F D Y
(SEQ ID NO: 25 (or a variant thereof having
1, 2, 3 or 4 point mutations and/or point
deletions))

V_L domain (DNA):
GCCATCCAGATGACCCAGTCTCCATCCTCCCTGTCTGCAT

CTGTAGGAGACAGAGTCACCATCACTTGCCGGGCAAGTCA

GGGCATTAGAAATGATTTAGGCTGGTATCAACAGAAACCA

GGGAAAGCCCCTAAACTCCTGATCTATGCTGCATCCAGTT

TACAAAGTGGGGTCCCATCGAGGTTCGCCGCCGTGGATC

TGGCACAGATTTCACTCTCACCATCAGCAGCCTGCAGCCT

GAAGATTTTGCAACTTATTACTGTCTACAAGATTTCAATT

ACCCGTGGACGTTCGGCCAAGGGACCAA
GGTGGAAATCAAA
(SEQ ID NO: 26)

V_L domain (Polypeptide):
AIQMTQSPSSLSASVGDRVTITCRASQGIRNDLGWYQQKP

GKAPKLLIYAASSLQSGVPSRFAGRGSGTDFTLTISSLQP

EDFATYYCLQDFNYPWTFGQGTKVEIK
(SEQ ID NO: 27)

Light immunoglobulin chain (kappa)
AIQMTQSPSSLSASVGDRVTITCRASQGIRNDLGWYQQKP

GKAPKLLIYAASSLQSGVPSRFAGRGSGTDFTLTISSLQP

EDFATYYCLQDFNYPWTFGQGTKVEIKRTVAAPSVFIFPP

SDEQLKSGTASVVCLLNNFYPREAKVQWKVDNALQSGNSQ

ESVTEQDSKDSTYSLSSTLTLSKADYEKHKVYACEVTHQG

LSSPVTKSFNRGEC
(SEQ ID NO: 83)

CDR-L1 (DNA):
CAG GGC ATT AGA AAT GAT
(SEQ ID NO: 28)

CDR-L1 (Polypeptide):
Q G I R N D
(SEQ ID NO: 29 (or a variant thereof having
1, 2, 3 or 4 point mutations and/or point
deletions))

CDR-L2 (DNA):
GCT GCA TCC
(SEQ ID NO: 30)

CDR-L2 (Polypeptide):
A A S
(SEQ ID NO: 31 (or a variant thereof having
a point mutation or point deletion))

CDR-L3 (DNA):
CTA CAA GAT TT C AAT TAC CCG TGG ACG
(SEQ ID NO: 32)

CDR-L3 (Polypeptide):
L Q D F N Y P W T
(SEQ ID NO: 33 (or a variant thereof having
1, 2, 3 or 4 point mutations and/or point
deletions))

H4H12170P
V_H domain (DNA):
CAGGTGCAGCTGGTGGAGTCTGGGGGAGGCGTGGTCCAGC

CTGGGAGGTCCCTGAGACTCTCCTGTGCAGCGTCTGGATT

CACCTTCAGTGGTTATGGCATGCACTGGGTCCGCCAGGCT

CCAGGCAAGGGGCTGGAGTGGGTGGCACTTATATGGCTTG

ATGGAAGTAATGACTACTATGCAGACTCCGTGAAGGGCCG

ATTCACCATCTCCAGAGACAATTCCAAGAACACGTTATAT

CTGCAAATGAACAGACTGAGAGCCGAGGACACGGCTGTGT

ATTACTGTGCGAGAGATGGCCCGGTTGCTGCTATACCCGA

CTACTGGGGCCAGGGAACCCTGGTCACCGTCTCCTCA
(SEQ ID NO: 34)

V_H domain (Polypeptide):
QVQLVESGGGVVQPGRSLRLSCAASGFTFSGYGMHWVRQA

PGKGLEWVALIWLDGSNDYYADSVKGRFTISRDNSKNTLY

LQMNRLRAEDTAVYYCARDGPVAAIPDYWGQGTLVTVSS
(SEQ ID NO: 35)

Heavy immunoglobulin chain (IgG4):
QVQLVESGGGVVQPGRSLRLSCAASGETFSGYGMHWVRQA

PGKGLEWVALIWLDGSNDYYADSVKGRFTISRDNSKNTLY

LQMNRLRAEDTAVYYCARDGPVAAIPDYWGQGTLVTVSSA

STKGPSVFPLAPCSRSTSESTAALGCLVKDYFPEPVTVSW

NSGALTSGVHTFPAVLQSSGLYSLSSVVTVPSSSLGTKTY

TCNVDHKPSNTKVDKRVESKYGPP
(SEQ ID NO: 84)

CDR-H1 (DNA):
GGA TTC ACC TT C AGT GGT TAT GGC
(SEQ ID NO: 36)

CDR-H1 (Polypeptide):
G F T F S G Y G
(SEQ ID NO: 37 (or a variant thereof having
1, 2, 3 or 4 point mutations and/or point
deletions))

CDR-H2 (DNA):
ATA TGG CTT GAT GGA AGT AAT GAC
(SEQ ID NO: 38)

CDR-H2 (Polypeptide):
I W L D G S N D
(SEQ ID NO: 39 (or a variant thereof having
1, 2, 3 or 4 point mutations and/or point
deletions))

CDR-H3 (DNA):
GCG AGA GAT GGC CCG GTT GCT GCT ATA CCC
GAC TAC
(SEQ ID NO: 40)

CDR-H3 (Polypeptide):
A R D G P V A A I P D Y
(SEQ ID NO: 41 (or a variant thereof having
1, 2, 3 or 4 point mutations and/or point
deletions))

V_L domain (DNA):
GACATCCAGATGACCCAGTCTCCTTCCACCCTGTCTGCAT

CTGTAGGAGACAGAGTCACCATCACTTGCCGGGCCAGTCA

GAGTATTAGTAGGTGGTTGGCCTGGTATCAGCTGAAACCA

GGGAAAGCCCCTAAGCTCCTGATCTATAAGGCGTCTAGTT

TAGAAAGTGGGGTCCCATCAAGGTTCAGCGGCAGTGGATC

TGGGACAGACTTCACTCTCACCATCAGCAGCCTGCAACCT

GATGATTTTGCAACTTATTACTGCCAACAGTATAATACTT

ATTCGTACACTTTTGGCCAGGGGACCAAGCTGGAGATCAA

A
(SEQ ID NO: 42)

V_L domain (Polypeptide):
DIQMTQSPSTLSASVGDRVTITCRASQSISRWLAWYQLKP

GKAPKLLIYKASSLESGVPSRFSGSGSGTDFTLTISSLQP

DDFATYYCQQYNTYSYTFGQGTKLEIK
(SEQ ID NO: 43)

Light immunoglobulin chain (kappa)
DIQMTQSPSTLSASVGDRVTITCRASQSISRWLAWYQLKP

GKAPKLLIYKASSLESGVPSRFSGSGSGTDFTLTISSLQP

DDFATYYCQQYNTYSYTEGQGTKLEIKRTVAAPSVFIFPP

SDEQLKSGTASVVCLLNNEYPREAKVQWKVDNALQSGNSQ

ESVTEQDSKDSTYSLSSTLTLSKADYEKHKVYACEVTHQG

LSSPVTKSFNRGEC
(SEQ ID NO: 85)

CDR-L1 (DNA):
CAG AGT ATT AGT AGG TGG
(SEQ ID NO: 44)

CDR-L1 (Polypeptide):
Q S I S R W
(SEQ ID NO: 45 (or a variant thereof having
1, 2, 3 or 4 point mutations and/or point
deletions))

CDR-L2 (DNA):
AAG GCG TCT
(SEQ ID NO: 46)

CDR-L2 (Polypeptide):
K A S
(SEQ ID NO: 47 (or a variant thereof having
a point mutation or point deletion))

CDR-L3 (DNA):
CAA CAG TAT AAT ACT TAT TCG TAC ACT
(SEQ ID NO: 48)

CDR-L3 (Polypeptide):
Q Q Y N T Y S Y T
(SEQ ID NO: 49 (or a variant thereof having
1, 2, 3 or 4 point mutations and/or point
deletions))
H4H12171P V_H domain (DNA):
GAGGTGCAGCTGGTGGAGTCTGGGGGAGGTGTGGTACGGC

CTGGGGGGTCCCTGAGACTCTCCTGTGCAGCCTCTGGATT

CACCTTTGATGAATATGGCATGACTTGGGTCCGCCAAGTT

CCAGGGAAGGGGCTGGAGTGGGTCTCTGGTATTACTTGGA

ATGGTGGTTTCACAGATTATACAGACTCTGTGAAGGGCCG

ATTCACCAGCTCCAGAGACAACGCCAAGAACTCCCTGTAT

CTGCAAATGAACAGTCTGAGAGCCGAGGACACGGCCTTGT

ATTACTGTGCGAGAGATGGATATAGCAGCTCGTGGGGGC

TTATGATATATGGGGCCAAGGGACAATGGTCACCGTCTCT

TCA
(SEQ ID NO: 50)

V_H domain (Polypeptide):
EVQLVESGGGVVRPGGSLRLSCAASGFTFDEYGMTWVRQV

PGKGLEWVSGITWNGGFTDYTDSVKGRFTSSRDNAKNSLY

LQMNSLRAEDTALYYCARDGYSSSWGAYDIWGQGTMVTVS

S
(SEQ ID NO: 51)

CDR-H1 (DNA):
GGA TTC ACC TTT GAT GAA TAT GGC
(SEQ ID NO: 52)

CDR-H1 (Polypeptide):
G  F  T  F  D  E  Y  G
(SEQ ID NO: 53 (or a variant thereof having
1, 2, 3 or 4 point mutations and/or point
deletions))

CDR-H2 (DNA):
ATT ACT TGG AAT GGT GGT TTC ACA
(SEQ ID NO: 54)

CDR-H2 (Polypeptide):
I  T  W  N  G  G  F  T
(SEQ ID NO: 55 (or a variant thereof having
1, 2, 3 or 4 point mutations and/or point
deletions))

CDR-H3 (DNA):
GCG AGA GAT GGA TAT AGC AGC TCG TGG GGG GCT
TAT GAT ATA
(SEQ ID NO: 56)

CDR-H3 (Polypeptide):
A  R  D  G  Y  S  S  S  W
G  A  Y  D  I
(SEQ ID NO: 57 (or a variant thereof having
1, 2, 3 or 4 point mutations and/or point
deletions))

V_L domain (DNA):
GACATCCAGATGACCCAGTCTCCATCATCCCTGTCTGCAT

CTGTGGGAGACAGAGTCACCATCACTTGCCGGGCAAGTCA

GAGCATTAGCACCTATTTAAATTGGTATCAGCAGAAACCA

GGGAAAGCCCCTAAGCTCCTGATCTATGCTGCATCCAGTT

TGCAAAGTGGGGTCCCATTAAGGTTCAGTGGCAGTGGATC

TGGGACTGATTTCACTCTCACCATCAGCAGTCTGCAACCT

GAAGATTTTGCAAGTTATTTCTGTCAACAGAGTTACAGTA

CCCCGTACACTTTTGGCCAGGGGACCAAGCTGGAGATCAA

A
(SEQ ID NO: 58)

V_L domain (Polypeptide):
DIQMTQSPSSLSASVGDRVTITCRASQSISTYLNWYQQKP

GKAPKLLIYAASSLQSGVPLRFSGSGSGTDFTLTISSLQP

EDFASYFCQQSYSTPYTFGQGTKLEIK
(SEQ ID NO: 59)

CDR-L1 (DNA):
CAG AGC ATT AGC ACC TAT
(SEQ ID NO: 60)

CDR-L1 (Polypeptide):
Q  S  I  S  T  Y
(SEQ ID NO: 61 (or a variant thereof having
1, 2, 3 or 4 point mutations and/or point
deletions))

CDR-L2 (DNA):
GCT GCA TCC
(SEQ ID NO: 62)

CDR-L2 (Polypeptide):
A  A  S
(SEQ ID NO: 63 (or a variant thereof having
a point mutation or point deletion))

CDR-L3 (DNA):
CAA CAG AGT TAC AGT ACC CCG TAC ACT
(SEQ ID NO: 64)

CDR-L3 (Polypeptide):
Q  Q  S  Y  S  T  P  Y  T
(SEQ ID NO: 65 (or a variant thereof having
1, 2, 3 or 4 point mutations and/or point
deletions))

H4H12175P
V_H domain (DNA):
GAAGTGCAGCTGGTGGAGTCTGGGGGAGGCGTGGTACAGC

CTGGGGGGTCCCTGAGACTCTCCTGTGCAGCCTCTGGATT

CACCTTTAATGATTATGCCATGCACTGGGTCCGTCAAGCT

CCAGGGAAGGGTCTGGAGTGGGTCTCTCTTATTAGTGGAG

ATGGTGGTAACACATACTATGCAGACTCTGTGAAGGGCCG

ACTCACCATCTCCAGAGACAACAGCAAAAACTCCCTGTAT

CTGCAAATGAACAGTCTGAGAACAGAGGACACCGCCTTAT

ATTACTGTGCAAAAGATAAGGGCTGGAACTTCGGTTACTT

CGATCTCTGGGGCCGTGGCACCCTGGTCACTGTCTCCTCA
(SEQ ID NO: 66)

V_H domain (Polypeptide):
EVQLVESGGGVVQPGGSLRLSCAASGFTFNDYAMHWVRQA

PGKGLEWVSLISGDGGNTYYADSVKGRLTISRDNSKNSLY

LQMNSLRTEDTALYYCAKDKGWNFGYFDLWGRGTLVTVSS
(SEQ ID NO: 67)

CDR-H1 (DNA):
GGA TTC ACC TTT AAT GAT TAT GCC
(SEQ ID NO: 68)

CDR-H1 (Polypeptide):
G  F  T  F  N  D  Y  A
(SEQ ID NO: 69 (or a variant thereof having
1, 2, 3 or 4 point mutations and/or point
deletions))

CDR-H2 (DNA):
ATT AGT GGA GAT GGT GGT AAC ACA
(SEQ ID NO: 70)

-continued

CDR-H2 (Polypeptide):
I S G D G G N T
(SEQ ID NO: 71 (or a variant thereof having 1, 2, 3 or 4 point mutations and/or point deletions))

CDR-H3 (DNA):
GCA AAA GAT AAG GGC TGG AAC TTC GGT TAC TTC GAT CTC
(SEQ ID NO: 72)

CDR-H3 (Polypeptide):
A K D K G W N F G Y F D L
(SEQ ID NO: 73 (or a variant thereof having 1, 2, 3 or 4 point mutations and/or point deletions))

V$_L$ domain (DNA):
GACATCCAGATGACCCAGTCTCCATCCTCCCTGTCTACAT
CTGTGGGAGACAGAGTCACCATCACTTGCCGGGCAAGTCA
GAACATTGACACCTATTTAAATTGGTATCAGCAGAAACCA
GGGAAAGCCCCTAAACTCCTGATCTATGATGCATCCAGTT
TACAAAGTGGGGTCCCATCACGGTTCAGTGGCAGCGGATC
TGGGACAGATTTCACTCTCACCATCACCAGTCTGCAACCT
GAAGATTTTGCCACTTACTACTGTCAACAGAATGACAATA
TTCTTCACCCTCTCACTTTCGGCGGAGGGACCAAGGTGGA
GATCAAA
(SEQ ID NO: 74)

V$_L$ domain (Polypeptide):
DIQMTQSPSSLSTSVGDRVTITCRAS<u>QNIDTYL</u>NWYQQKP
GKAPKLLIY<u>DAS</u>SLQSGVPSRFSGSGSGTDFTLTITSLQP
EDFATYYC<u>QQNDNILHPLT</u>FGGGTKVEIK
(SEQ ID NO: 75)

CDR-L1 (DNA):
CAG AAC ATT GAC ACC TAT
(SEQ ID NO: 76)

CDR-L1 (Polypeptide):
Q N I D T Y
(SEQ ID NO: 77 (or a variant thereof having 1, 2, 3 or 4 point mutations and/or point deletions))

CDR-L2 (DNA):
GAT GCA TCC
(SEQ ID NO: 78)

CDR-L2 (Polypeptide):
D A S
(SEQ ID NO: 79 (or a variant thereof having a point mutation or point deletion))

CDR-L3 (DNA):
CAA CAG AAT GAC AAT ATT CTT CAC CCT CTC ACT
(SEQ ID NO: 80)

CDR-L3 (Polypeptide):
Q Q N D N I L H P L T
(SEQ ID NO: 81 (or a variant thereof having 1, 2, 3 or 4 point mutations and/or point deletions))

H4H12176P2
V$_H$ domain (DNA):
GAGGTGCAGCTGGTGGAGTCTGGGGGAGGCTTGGTCCAAC
CGGGGGGGTCCCTGAGACTCTCCTGTGCAGCCTCTGGATT
CCACTCTAATAGATATTGGATGGACTGGGTCCGCCAGGCT
CCAGGGAAGGGGCTGGAGTGGGTGGCCAACATAAAGCAAG
ATGGAAGTGAGGAAAACTATGTGGACTCTGTGAAGGGCCG
ATTCACCATCTCCAGAGACAACGCCAAGAACTCACTTTAT
CTGCAAATGAACAGCCTGAGAGCCGAGGACACGGCTGTGT
ATTACTGTGCGAGAGATCGAAGCACCTCGTGGGTCCCTTA
CTGGTTCTTCGATCTCTGGGGCCGTGGCACCCTGGTCACT
GTCTCCTCA
(SEQ ID NO: 86)

V$_H$ domain (Polypeptide):
EVQLVESGGGLVQPGGSLRLSCAASG<u>FHSNRYWMD</u>WVRQA
PGKGLEWVAN<u>IKQDGSEE</u>NYVDSVKGRFTISRDNAKNSLY
LQMNSLRAEDTAVYYCA<u>RDRSTSWVPYWFFDL</u>WGRGTLVT
VSS
(SEQ ID NO: 87)

CDR-H1 (DNA):
GGA TTC CAC TCT AAT AGA TAT TGG
(SEQ ID NO: 88)

CDR-H1 (Polypeptide):
G F H S N R Y W
(SEQ ID NO: 89)

CDR-H2 (DNA):
ATA AAG CAA GAT GGA AGT GAG GAA
(SEQ ID NO: 90)

CDR-H2 (Polypeptide):
I K Q D G S E E
(SEQ ID NO: 91)

CDR-H3 (DNA):
GCG AGA GAT CGA AGC ACC TCG TGG GTC CCT TAC TGG TTC TTC GAT CTC
(SEQ ID NO: 92)

CDR-H3 (Polypeptide):
A R D R S T S W V P Y W F F D L
(SEQ ID NO: 93)

V$_L$ domain (DNA):
GACATCCAGATGACCCAGTCTCCATCCTCCCTGTCTGCAT
CTGTAGGAGACAGAGTCACCATCACTTGCCGGGCAAGTCA
GAGCATTAGCAGCTATTTAAATTGGTATCAGCAGAAACCA
GGGAAAGCCCCTAAGCTCCTGATCTATGCTGCATCCAGTT
TGCAAAGTGGGGTCCCGTCAAGGTTCAGTGGCAGTGGATC
TGGGACAGATTTCACTCTCACCATCAGCAGTCTGCAACCT
GAAGATTTTGCAACTTACTACTGTCAACAGAGTTACAGTA
CCCCTCCGATCACCTTCGGCCAAGGGACACGACTGGAGAT
TAAA
(SEQ ID NO: 94)

V$_L$ domain (Polypeptide):
DIQMTQSPSSLSASVGDRVTITCRAS<u>QSISSY</u>LNWYQQKP

GKAPKLLIY<u>AAS</u>SLQSGVPSRFSGSGSGTDFTLTISSLQP

EDFATYYC<u>QQSYSTPPIT</u>FGQGTRLEIK
(SEQ ID NO: 95)

CDR-L1 (DNA):
CAG AGC ATT AGC AGC TAT
(SEQ ID NO: 96)

CDR-L1 (Polypeptide):
Q    S    I    S    S    Y
(SEQ ID NO: 97)

CDR-L2 (DNA):
GCT GCA TCC
(SEQ ID NO: 98)

CDR-L2 (Polypeptide):
A    A    S
(SEQ ID NO: 99)

CDR-L3 (DNA):
CAA CAG AGT TAC AGT ACC CCT CCG ATC ACC
(SEQ ID NO: 100)

CDR-L3 (Polypeptide):
Q    Q    S    Y    S    T    P    P    I    T
(SEQ ID NO: 101)

H4H12177P2
V$_H$ domain (DNA):
GAAGTGCAGCTGGTGGAGTCTGGGGGAGGCGTGGTACAGC

GGGGGGAGTCCCTGAGACTCTCCTGTTCAGCCTCTGACTT

CATCTTTAAAGATTATGCCATGTACTGGGTCCGTCAAATT

CCAGGGAAGGGTCTAGAGTGGATCTCTCTTATTAGTGGTG

ATGGTGACACTACATGGTATGGAGACTCTGTGAAGGGCCG

ATTCACCATCTCCAGAGACAACAACGAAAACTCCCTCTTT

CTGCAAATGAACGATCTGAGAACTGAGGACACCGCCATGT

ACTACTGTGCAAGAGATATGGGGTGGAACTTCTTTCAGTT

GCAATACTGGGGCCAGGGAACCCTGGTCACCGTCTCCTCA
(SEQ ID NO: 102)

V$_H$ domain (Polypeptide):
EVQLVESGGGVVQRGESLRLSCSAS<u>DFIFKDYA</u>MYWVRQI

PGKGLEWIS<u>LISGDGDTT</u>WYGDSVKGRFTISRDNNENSLF

LQMNDLRTEDTAMYYCAR<u>DMGWNFFQLQY</u>WGQGTLVTVSS
(SEQ ID NO: 103)

CDR-H1 (DNA):
GAC TTC ATC TTT AAA GAT TAT GCC
(SEQ ID NO: 104)

CDR-H1 (Polypeptide):
D    F    I    F    K    D    Y    A
(SEQ ID NO: 105)

CDR-H2 (DNA):
ATT AGT GGT GAT GGT GAC ACT ACA
(SEQ ID NO: 106)

CDR-H2 (Polypeptide):
I    S    G    D    G    D    T    T
(SEQ ID NO: 107)

CDR-H3 (DNA):
GCA AGA GAT ATG GGG TGG AAC TTC TTT CAG

TTG CAA TAC
(SEQ ID NO: 108)

CDR-H3 (Polypeptide):
A    R    D    M    G    W    N    F

F    Q    L    Q    Y
(SEQ ID NO: 109)

V$_L$ domain (DNA):
GACATCCAGATGACCCAGTCTCCATCCTCCCTGTCTGCAT

CTGTAGGAGACAGAGTCACCATCACTTGCCGGGCAAGTCA

GAGCATTAGCAGCTATTTAAATTGGTATCAGCAGAAACCA

GGGAAAGCCCCTAAGCTCCTGATCTATGCTGCATCCAGTT

TGCAAAGTGGGGTCCCGTCAAGGTTCAGTGGCAGTGGATC

TGGGACAGATTTCACTCTCACCATCAGCAGTCTGCAACCT

GAAGATTTTGCAACTTACTACTGTCAACAGAGTTACAGTA

CCCCTCCGATCACCTTCGGCCAAGGGACACGACTGGAGAT

TAAA
(SEQ ID NO: 94)

V$_L$ domain (Polypeptide):
DIQMTQSPSSLSASVGDRVTITCRAS<u>QSISSY</u>LNWYQQKP

GKAPKLLIY<u>AAS</u>SLQSGVPSRFSGSGSGTDFTLTISSLQP

EDFATYYC<u>QQSYSTPPIT</u>FGQGTRLEIK
(SEQ ID NO: 95)

CDR-L1 (DNA):
CAG AGC ATT AGC AGC TAT
(SEQ ID NO: 96)

CDR-L1 (Polypeptide):
Q    S    I    S    S    Y
(SEQ ID NO: 97)

CDR-L2 (DNA):
GCT GCA TCC
(SEQ ID NO: 98)

CDR-L2 (Polypeptide):
A    A    S
(SEQ ID NO: 99)

CDR-L3 (DNA):
CAA CAG AGT TAC AGT ACC CCT CCG ATC ACC
(SEQ ID NO: 100)

CDR-L3 (Polypeptide):
Q    Q    S    Y    S    T    P    P    I    T
(SEQ ID NO: 101)

See WO2017/218515.

The present invention further includes a complex comprising a C5 polypeptide or an antigenic fragment thereof bound to one or more anti-C5 antigen-binding proteins. For example, in an embodiment of the invention, the complex comprises one or more C5 polypeptides or antigenic fragments thereof bound to one or more first anti-C5 antigen-binding proteins and one or more further anti-C5 antigen-binding proteins that do not compete for binding to the C5. Complexes can form with various ratios of first antigen-binding protein to second antigen-binding protein to C5. For example, the scope of the present invention includes a complex comprising:

(i) a 1:1:2, 2:2:4 or 3:3:6 ratio of first monospecific anti-C5 antigen-binding protein (e.g., H4H12166P)-to-second monospecific anti-C5 antigen-binding protein-to-C5 polypeptide or fragment
(ii) a 1:1, 1:2, 2:1 or 2:2 ratio of bispecific anti-C5 antigen-binding protein-to-C5 polypeptide or fragment;
(iii) a 1:1:1; 1:1:2 or 1:2:2 ratio of monospecific anti-C5 antigen-binding protein-to-bispecific anti-C5 antigen-binding protein-to-C5 polypeptide or fragment; or
(iv) a 1:2 ratio or monospecific anti-C5 antigen-binding protein-to-C5 polypeptide or fragment.

In an embodiment of the invention, the monospecific anti-C5 antigen-binding protein is eculizumab, H4H12166P, H4H12177P2 or H4H12176P2. In an embodiment of the invention, the bispecific anti-C5 antigen-binding protein is H4H12176P2xH4H12177P2.

Some complexes were surmised based upon the calculated molar mass of material eluting after asymmetric flow field-flow fractionation (A4F-MALLS) and the average calculated masses of the individual antibodies and C5 polypeptide in the mixtures analyzed. These data are set forth in FIGS. 11-16 herein.

Epitope Mapping and Competition

As discussed herein, the present invention provides combinations including a first antigen-binding protein (e.g., antibody or antigen-binding fragment thereof) that binds specifically to C5 and one or more further antigen-binding proteins (e.g., antibodies or antigen-binding fragments thereof or polypeptides) (e.g., coversin) that (i) specifically bind to C5 at an epitope which is different from that of the first antigen-binding protein and/or (ii) do not compete with the first antigen-binding protein for binding to C5.

Bispecific antigen-binding proteins (e.g., antibodies and antigen-binding fragments thereof) having two antigen-binding domains (a first and a second) wherein the first specifically binds to an epitope of C5 and the second (i) specifically bind to C5 at an epitope which is different from that of the first antigen-binding domain and/or (ii) do not compete with the first antigen-binding domain for binding to C5. Such antigen-binding domains, in an embodiment of the invention, are taken from the antibodies or antigen-binding fragments which are set forth in WO2017/218515.

Two antigen-binding proteins, e.g., antibodies, have a common epitope if there are common amino acids in the C5 antigen to which the antigen-binding proteins exhibit significant binding.

Methods for determining the epitope of an antigen-binding protein, e.g., antibody or fragment or polypeptide, include alanine scanning mutational analysis, peptide blot analysis (Reineke (2004) Methods Mol. Biol. 248: 443-63), peptide cleavage analysis, crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antigen-binding protein (e.g., antibody or fragment or polypeptide) (e.g., coversin) interacts is hydrogen/deuterium exchange detected by mass spectrometry. In general terms, the hydrogen/deuterium exchange method involves deuterium-labeling the protein of interest, followed by binding the antigen-binding protein, e.g., antibody or fragment or polypeptide, to the deuterium-labeled protein. Next, the C5 protein/antigen-binding protein complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antigen-binding protein interface may retain deuterium and therefore exhibit relatively higher mass compared to amino acids not included in the interface. After dissociation of the antigen-binding protein (e.g., antibody or fragment or polypeptide), the target protein is subjected to protease cleavage and mass spectrometry analysis, thereby revealing the deuterium-labeled residues which correspond to the specific amino acids with which the antigen-binding protein interacts. See, e.g., Ehring (1999) Analytical Biochemistry 267: 252-259; Engen and Smith (2001) Anal. Chem. 73: 256A-265A.

The term "epitope" refers to an antigenic determinant (e.g., on C5) that interacts with a specific antigen-binding site in an antigen-binding protein, e.g., variable region of an antibody molecule, known as a paratope. A single antigen may have more than one epitope. Thus, different antigen-binding proteins, e.g., antibodies, may bind to different areas on an antigen and may have different biological effects. Epitopes, composed of non-contiguous amino acids, may be referred to as "conformational". A linear epitope contains only contiguous amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

For example, the epitope to which antibody H4H12166P bins is defined by: (i) the amino acid sequence NMATGMDSW which corresponds to amino acids 591 to 599 in the beta chain included in SEQ ID NO: 1; and (ii) the amino acid sequence WEVHLVPRRKQLQFALPDSL, which corresponds to amino acids 775 to 794 comprised in the alpha chain included in SEQ ID NO: 1. See for example, PCT International Application No. PCT/US2017/037226. The C5 epitope of Eculizumab is disclosed in Brachet et al., Eculizumab epitope on complement C5: Progress towards a better understanding of the mechanism of action. Mol Immunol. 2016 September; 77: 126-131.

The term "competes" as used herein, refers to an antigen-binding protein (e.g., antibody or antigen-binding fragment thereof) that binds to an antigen and inhibits or blocks the binding of another antigen-binding protein (e.g., antibody or antigen-binding fragment thereof) to the antigen. The term also includes competition between two antigen-binding protein e.g., antibodies, in both orientations, i.e., a first antibody that binds and blocks binding of second antibody and vice versa. In certain embodiments, the first antigen-binding protein (e.g., antibody) and second antigen-binding protein (e.g., antibody) may bind to the same epitope. Alternatively, the first and second antigen-binding proteins (e.g., antibodies) may bind to different, but, for example, overlapping epitopes, wherein binding of one inhibits or blocks the binding of the second antibody, e.g., via steric hindrance. Cross-competition between antigen-binding proteins (e.g., antibodies) may be measured by methods known in the art, for example, by a real-time, label-free bio-layer interferometry assay. In an embodiment of the invention, competition between a first and second anti-C5 antigen-binding protein (e.g., antibody) is determined by measuring the ability of an immobilized first anti-C5 antigen-binding protein (e.g., antibody) (not initially complexed with C5 protein) to bind to soluble C5 protein complexed with a second anti-C5 antigen-binding protein (e.g., antibody). A reduction in the ability of the first anti-C5 antigen-binding protein (e.g., antibody) to bind to the complexed C5 protein, relative to uncomplexed C5 protein, indicates that the first and second anti-C5 antigen-binding proteins (e.g., antibodies) compete. The degree of competition can be expressed as a percentage of the reduction in binding. Such competition can be measured using a real time, label-free bio-layer interferometry assay, e.g., on an Octet RED384 biosensor (Pall ForteBio Corp.), ELISA (enzyme-linked immunosorbent assays) or SPR (surface plasmon resonance).

Binding competition between anti-C5 antigen-binding proteins (e.g., monoclonal antibodies (mAbs)) can be determined using a real time, label-free bio-layer interferometry assay on an Octet RED384 biosensor (Pall ForteBio Corp.). For example, to determine competition between two anti-human C5 monoclonal antibodies, the anti-C5 mAb can be first captured onto anti-hFc antibody coated Octet biosensor tips (Pall ForteBio Corp., #18-5060) by submerging the tips into a solution of anti-human C5 mAb (subsequently referred to as "mAb1"). As a positive-control for blocking, the antibody captured biosensor tips can then be saturated with a known blocking isotype control mAb (subsequently referred to as "blocking mAb") by dipping into a solution of blocking mAb. To determine if mAb2 competes with mAb1, the biosensor tips can then be subsequently dipped into a co-complexed solution of human C5 polypeptide and a second anti-human C5 mAb (subsequently referred to as "mAb2"), that had been pre-incubated for a period of time and binding of mAb1 to the C5 polypeptide can be determined. The biosensor tips can be washed in buffer in between every step of the experiment. The real-time binding response can be monitored during the course of the experiment and the binding response at the end of every step can be recorded. mAb2-dependent inhibition of mAb1/C5 binding indicates competition between mAb1 and mAb2 for C5 binding. See e.g., International Patent Application No. PCT/US2017/037226, filed Jun. 13, 2017, e.g., Example 5 therein.

In an embodiment of the invention, competition between antigen-binding proteins, such as antibodies, is determined under the conditions set forth in Example 5. For example, in an embodiment of the invention, the assay is conducted at 25° C. and pH about 7.4, e.g., in the presence of buffer (e.g., HEPES), salt (e.g., NaCl), surfactant (e.g., Tween-20) and a protein (e.g., bovine serum albumin), e.g., 0.01 M HEPES pH7.4, 0.15M NaCl, 0.05% v/v Surfactant Tween-20, 0.1 mg/mL BSA (Octet HBS-P buffer) with the plate shaking at the speed of 1000 rpm.

Competition between anti-C5 antibodies set forth in International Patent Application No. PCT/US2017/037226 (WO2017/218515), filed Jun. 13, 2017 is summarized below in Table 1. Accordingly, the present invention includes combinations comprising two anti-C5 antibodies or antigen-binding fragments thereof selected from Table 1 wherein the antibodies or fragments do not compete for 5 binding (e.g., H4H12166P and H4H12168P or H4H12166P and H4H12161P; or H4H12166P and H4H1686N).

TABLE 1

Competition between pairs of selected anti-C5 antibodies.

| First mAb (mAb1) Captured using AHC Octet | mAb2 Antibodies Shown to Compete with mAb1 |
|---|---|
| H4H12183P2 | H4H12167P; H4H12166P; H4H12163P |
| H4H12167P | H4H12183P2; H4H12166P; H4H12163P |
| H4H12166P | H4H12183P2; H4H12167P; H4H12163P |
| H4H12163P | H4H12183P2; H4H12167P; H4H12166P |

TABLE 1-continued

Competition between pairs of selected anti-C5 antibodies.

| First mAb (mAb1) Captured using AHC Octet | mAb2 Antibodies Shown to Compete with mAb1 |
|---|---|
| H4H12159P | H4H12169P; H4H11683N; H4H12170P |
| H4H12169P | H4H12159P; H4H11683N; H4H12170P |
| H4H11683N | H4H12159P; H4H12169P; H4H12170P |
| H4H12170P | H4H12159P; H4H12169P; H4H11683N |
| H4H12175P | H4H12177P2 |
| H4H12177P2 | H4H12175P |
| H4H12176P2 | H4H12164P |
| H4H12164P | H4H12176P2 |
| H4H12168P | none |
| H4H12161P | none |
| H4H11686N | none |
| H4H12171P | none |

See WO2017/218515, Table 15.

Pharmaceutical Compositions and Administration

Combinations of the present invention (e.g., H4H12166P and one of H4H12161P, H4H12170P, H4H12171P, H4H12175P, H4H12176P2 or H4H12177P2) include components that may be formulated into a single, common composition or into multiple/separate compositions. Moreover, separate compositions may be formulated with different varieties of carriers. For example, a first antigen-binding protein (e.g., antibody or antigen-binding fragment thereof) that binds specifically to C5, which is part of a combination of the present invention, can be co-formulated into a single composition (e.g., with a pharmaceutically acceptable carrier) with one or more further antigen-binding proteins (e.g., antibodies or antigen-binding fragments thereof or polypeptides)(e.g., coversin) that (i) specifically bind to C5 at an epitope which is different from that of the first antigen-binding protein (e.g., antibody or fragment) and/or (ii) do not compete with the first antigen-binding protein (e.g., antibody or fragment) for binding to C5. In embodiment of the invention, the first antigen-binding protein (e.g., antibody or fragment) and the second antigen-binding protein (e.g., antibody or fragment or polypeptide) are formulated into separate compositions (e.g., with pharmaceutically acceptable carriers). A further therapeutic agent, in a combination of the present invention, may be formulated into yet another composition. A further therapeutic agent may be included in a combination of the present invention separately from the first antibody or fragment and the second antibody or fragment or polypeptide. In another embodiment of the invention, the further therapeutic agent is formulated into either the first antibody or fragment or the second antibody or fragment or polypeptide (or both).

To prepare pharmaceutical or sterile compositions comprising the components of the combinations of the present invention, the component(s) may be is admixed with a pharmaceutically acceptable carrier or excipient. See, e.g., Remington's Pharmaceutical Sciences and U.S. Pharmacopeia: National Formulary, Mack Publishing Company, Easton, Pa. (1984). Combinations including such compositions are part of the present invention.

The scope of the present invention includes combinations including one or more components in desiccated form, e.g., freeze-dried, substantially lacking water.

Formulations may be prepared by mixing with acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

If a combination of the present invention includes a further therapeutic agent that is administered to a subject, the further therapeutic agent may be is administered to the subject in accordance with the Physicians' Desk Reference (PDR), e.g., Physicians' Desk Reference 2003 (Thomson Healthcare; 57th edition (Nov. 1, 2002)) and/or may formulated as described in the PDR.

The mode of administration of a combination or any of the components of a combination can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

The present invention provides methods for administering a combination or component thereof comprising introducing the substance into the body of a subject. For example, the method comprises piercing the body of the subject with a needle of a syringe and injecting the combination or a component thereof into the body of the subject, e.g., into the vein, artery, tumor, muscular tissue or subcutis of the subject.

The present invention provides a vessel (e.g., a plastic or glass vial, e.g., with a cap or a chromatography column, hollow bore needle or a syringe cylinder) comprising a combination of the present invention or one or more components thereof.

The present invention also provides an injection device comprising a one or more antigen-binding proteins (e.g., antibody, antigen-binding fragment or polypeptide) from a combination of the present invention or a pharmaceutical composition thereof. For example, one antigen-binding protein (from a combination) may be in a first injection device and another antigen-binding protein (from the combination) may be in a second injection device; or both antigen-binding proteins (from the combination) may be in a common injection device. The injection device(s) may be (co-)packaged into a kit. An injection device is a device that introduces a substance into the body of a subject via a parenteral route, e.g., intramuscular, subcutaneous or intravenous. For example, an injection device may be a syringe (e.g., pre-filled with the pharmaceutical composition, such as an autoinjector) which, for example, includes a cylinder or barrel for holding fluid to be injected (e.g., comprising the antibody or fragment or a pharmaceutical composition thereof), a needle for piecing skin and/or blood vessels for injection of the fluid; and a plunger for pushing the fluid out of the cylinder and through the needle bore. In an embodiment of the invention, an injection device that comprises an antigen-binding protein, e.g., an antibody or antigen-binding fragment thereof, from a combination of the present invention, or a pharmaceutical composition thereof is an intravenous (IV) injection device. Such a device can include the antigen-binding protein or a pharmaceutical composition thereof in a cannula or trocar/needle which may be attached to a tube which may be attached to a bag or reservoir for holding fluid (e.g., saline) introduced into the body of the subject through the cannula or trocar/needle. The antibody or fragment or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the antibody or fragment or a pharmaceutical composition thereof to a subject's body. External infusion pumps are medical devices that deliver the antibody or fragment or a pharmaceutical composition thereof into a subject's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

The present invention includes methods for treating a C5-associated disease or disorder (e.g., PNH or aHUS) in a subject (e.g., a human) in need thereof by administering (e.g., parenterally), to the subject, a therapeutically effective amount of a combination comprising:

(1) a first antigen-binding protein (e.g., antibody or antigen-binding fragment thereof) that binds specifically to C5 and one or more further antigen-binding proteins (e.g., polypeptides (e.g., coversin) or antibodies or antigen-binding fragments thereof) that (i) specifically bind to C5 at an epitope which is different from that of the first antigen-binding protein (e.g., antibody or fragment) and/or (ii) does not compete with the first antigen-binding protein (e.g., antibody or fragment) for binding to C5; or (2) a multispecific antigen-binding protein (e.g., antibody or antigen-binding fragment thereof) (e.g., biparatopic anti-C5 IgG antibody) comprising two or more binding domains (e.g., first and second binding domain) that bind to different epitopes of C5 wherein the first binding domain (i) specifically binds to C5 at an epitope which is different from that of the second binding domain and/or (ii) does not compete with the second binding domain for binding to C5;

optionally in association with a further therapeutic agent (e.g., a corticosteroid) and/or procedure (e.g., blood transfusion, e.g., in a human subject suffering from PNH).

"Treat" or "treating" means to administer a combination of the present invention, to a subject having one or more symptoms of a C5-associated disease or disorder for which the combination is effective, e.g., in the treatment of a subject having paroxysmal nocturnal hemoglobinuria (PNH) or atypical hemolytic uremic syndrome (aHUS), or being suspected of having PNH or aHUS. Typically, the combination is administered in an effective or therapeutically amount or dose (as discussed herein).

Guidance in selecting appropriate doses of combination of the present or a component thereof is available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert et al. (2003) New Engl. J. Med. 348:601-608; Milgrom et al. (1999) New Engl. J. Med. 341:1966-1973; Slamon et al. (2001) New Engl. J. Med. 344:783-792; Beniaminovitz et al. (2000) New Engl. J. Med. 342:613-619; Ghosh et al. (2003) New Engl. J. Med. 348: 24-32; Lipsky et al. (2000) New Engl. J. Med. 343:1594-1602).

An effective or therapeutically effective dose of anti-C5 antigen-binding protein (e.g., antibody or antigen-binding fragment or polypeptide) in a combination of the invention for treating a C5-associated disease or disorder refers to the amount of the combination sufficient to alleviate one or more signs and/or symptoms of the disease or disorder (e.g., an underlying cause such as complement activation) in the treated subject or population, whether by inducing the regression or elimination of such signs and/or symptoms or by inhibiting the progression of such signs and/or symptoms. The dose amount may vary depending upon the age and the size of a subject to be administered, target disease, conditions, route of administration, and the like. In an embodiment of the invention, an effective or therapeutically effective dose of antigen-binding protein (e.g., antibody or antigen-binding fragment thereof) of a combination of the present invention, for treating or preventing a C5-associated disease or disorder, e.g., in an adult human subject, is a single dose of about 0.1 to about 100 mg/kg body weight, e.g., about 5 to about 80, e.g., about 10 to about 70, or about 20 to about 50 mg/kg body weight. Depending on the severity of the condition, the frequency and the duration of the treatment can be adjusted. In certain embodiments, the antigen-binding protein (e.g., antibody or antigen-binding fragment thereof) in a combination of the present invention can be administered as an initial dose of at least about 0.1 mg to about 800 mg, about 1 to about 600 mg, about 5 to about 500 mg, or about 10 to about 400 mg. In certain embodiments, the initial dose may be followed by administration of a second or a plurality of subsequent doses of the antigen-binding protein (e.g., antibody or antigen-binding fragment thereof) in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

In an embodiment of the invention, coversin, in a combination of the present invention, is administered, for a first dose, at 0.57 mg/kg, followed by daily repeat maintenance doses wherein initial repeat dose is 25% of the ablating dose.

A "C5-associated" disease or disorder refers to a disease or disorder which is caused (directly or indirectly) by inflammation, cell injury and/or cell killing that is mediated by C5a and/or C5b.

A C5-associated disease or disorder includes atypical hemolytic uremic syndrome (aHUS). The present invention provides a method for treating or preventing aHUS or for inducing the regression or elimination or inhibiting the progression of at least one sign or symptom of aHUS such as:
  platelet activation;
  hemolysis;
  systemic thrombotic microangiopathy (formation of blood clots in small blood vessels throughout the body), e.g., leading to stroke;
  heart attack;
  kidney failure (e.g., leading to death);
  end-stage renal disease;
  permanent renal damage;
  abdominal pain;
  confusion;
  edema;
  fatigue;
  nausea/vomiting;
  diarrhea; and/or
  microangiopathic anemia,
in a subject in need thereof (e.g., in a subject suffering from aHUS and suffering from one or more of such signs or symptoms) by administering a therapeutically effective amount of the combination to the subject.

A C5-associated disease or disorder includes paroxysmal nocturnal hemoglobinuria (PNH). The present invention provides a method for treating or preventing PNH or for inducing the regression or elimination or inhibiting the progression of at least one sign or symptom of PNH such as:
  destruction of red blood cells;
  thrombosis (e.g., deep vein thrombosis and/or pulmonary embolism);
  intravascular hemolytic anemia;
  red discoloration of urine;
  anemia;
  tiredness;
  shortness of breath;
  heart palpitations;
  abdominal pain; and/or
  difficulty swallowing,
in a subject in need thereof (e.g., in a subject suffering from aHUS and suffering from one or more of such signs or symptoms) by administering a therapeutically effective amount of the combination to the subject.

A C5-associated disease or disorder includes neurological disorders, renal disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, post-ischemic reperfusion conditions, myocardial infarction, capillary leak syndrome, obesity, diabetes, Alzheimer's disease, schizophrenia, stroke, epilepsy, atherosclerosis, vasculitis, bullous pemphigoid, C3 glomerulopathy, membraneproliferative glomerulonephritis, complement activation caused by balloon angioplasty, post-pump syndrome in cardiopulmonary bypass or renal bypass, complement activation caused by hemodialysis, renal ischemia, mesenteric artery reperfusion after aortic reconstruction, infectious disease or sepsis, immune complex disorders and autoimmune diseases, diabetic nephropathy, Alport's syndrome, progressive kidney failure, proteinuric kidney diseases, renal ischemia-reperfusion injury, lupus nephritis, glomerulopathy, rheumatoid arthritis, systemic lupus erythematosus (SLE), SLE nephritis, membranoproliferative nephritis, hemolytic anemia, neuromyelitis optica, renal transplant, inherited CD59 deficiency, psoriasis, and myasthenia gravis. The present invention includes methods for treating or preventing any of the foregoing C5-related diseases or disorders, in a subject, by administering a therapeutically effective amount of a combination of the present invention to the subject in need thereof.

In certain other embodiments, the combinations of the present invention are useful for treating or preventing at least one symptom or indication of a C5-associated disease or disorder selected from the group consisting of lung disease and disorders such as dyspnea, hemoptysis, ARDS, asthma, chronic obstructive pulmonary disease (COPD), emphysema, pulmonary embolisms and infarcts, pneumonia, fibrogenic dust diseases, injury due to inert dusts and minerals (e.g., silicon, coal dust, beryllium, and asbestos), pulmonary fibrosis, organic dust diseases, chemical injury (due to irritant gasses and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, hereditary angioedema, and immune complex-associated inflammation. The present invention includes methods for treating or preventing any of the foregoing C5-related diseases or disorders, in a subject, by administering a therapeutically effective amount of a combination of the present invention to the subject in need thereof.

An ocular disease which is a C5-related disease or disorder includes, for example, age-related macular degeneration (AMD), diabetic macular edema (DME), diabetic retinopathy, ocular angiogenesis (ocular neovascularization affecting choroidal, corneal or retinal tissue), geographic atrophy (GA), uveitis and neuromyelitis optica. The present invention provides a method for treating or preventing an ocular disease or for inducing the regression or elimination or inhibiting the progression of at least one sign or symptom of an ocular disease such as:

increased rate of loss of vision;
drusen in the eye (e.g., of a subject with dry AMD);
loss of vision;
gradual loss of central vision (e.g., in subjects with non-exudative macular degeneration);
visual distortion;
difficulty adapting to low light levels;
crooked central vision;
haziness of central and/or overall vision;
eye pigmentary changes;
distorted vision (e.g., metamorphopsia in which a grid of straight lines appears wavy and parts of the grid may appear blank);
exudative changes (e.g., hemorrhages in the eye, hard exudates, subretinal/sub-RPE/intraretinal fluid);
slow recovery of visual function after exposure to bright light (e.g., as determined in a photostress test);
incipient and/or geographic atrophy;
drastically decreasing visual acuity (e.g., two levels or more, e.g., 20/20 to 20/80);
preferential hyperacuity perimetry changes (e.g., in a subject with wet AMD);
blurred vision;
rapid onset of vision loss (e.g., caused by leakage and bleeding of abnormal blood vessels in subjects with exudative macular degeneration);
central scotomas (shadows or missing areas of vision);
trouble discerning colors (e.g., specifically dark colors from other dark colors and/or light colors from other light colors);
loss in contrast sensitivity; and/or
straight lines appear curved in an Amsler grid, in a subject in need thereof (e.g., in a subject suffering from an ocular disease and suffering from one or more of such signs or symptoms) by administering a therapeutically effective amount of the combination to the subject.

It is also contemplated herein to administer a therapeutically effective amount of a combination of the present invention prophylactically to subjects at risk for developing a C5-associated disease or disorder, e.g., aHUS, PNH or macular degeneration, such as subjects over the age of 50, subjects with a family history of macular degeneration, smokers, and subjects with obesity, high cholesterol, cardiovascular disease, and/or unhealthy diet.

Combination Therapies

The present invention provides combinations comprising a first antigen-binding protein (e.g., antibody or antigen-binding fragment thereof) that binds specifically to C5 and one or more further antigen-binding proteins (e.g., polypeptides or antibodies or antigen-binding fragments thereof) that (i) specifically bind to C5 at an epitope which is different from that of the first antigen-binding protein (e.g., antibody or fragment) and/or (ii) does not compete with the first antigen-binding protein (e.g., antibody or fragment) for binding to C5 (e.g., H4H12166P and one of H4H12161P, H4H12170P, H4H12171P, H4H12175P, H4H12176P2 or H4H12177P2). Such combinations may further include one or more further therapeutic agents and/or one or more therapeutic methods. For example, the further therapeutic agent may be formulated into a single composition with one or more components of a combination of the present invention or formulated separately from one or both of the components. The present invention provides a method for treating or preventing a C5-associated disease or disorder or for treating or ameliorating at least one symptom or indication of such a disease or disorder in a subject in need thereof by administering a therapeutically effective amount of the combination to the subject, optionally in association with one or more further therapeutic agents.

In an embodiment of the invention, the further therapeutic agent is another anti-C5 antibody or antigen-binding fragment thereof which is not, itself a first or second/further antibody or fragment in the combination, such as for example, one or more antibodies or antigen-binding fragments thereof selected from H2M11683N; H2M11686N; H4H12159P; H4H12163P; H4H12164P; H4H12166P2; H4H12166P3; H4H12166P4; H4H12166P5; H4H12166P6; H4H12166P7; H4H12166P8; H4H12166P9; H4H12166P10; H4H12167P; H4H12168P; H4H12169P; H4H12176P2; H4H12177P2; H4H12183P2; H2M11682N; H2M11684N; H2M11694N; and H2M11695N—as set forth in International PCT patent application no. PCT/US2017/037226 (or a variant thereof; or an antigen-binding protein such as an antibody or antigen-binding fragment that comprises a heavy chain immunoglobulin including CDR-H1, CDR-H2 and CDR-H3; and a light chain immunoglobulin including CDR-L1, CDR-L2 and CDR-L3 of any of the foregoing antibodies) (which is not a first or second/further antibody or antigen-binding fragment in the combination).

Such a further therapeutic agent includes, for example, iron, antithymocyte globulin, a growth factor, an anti-coagulant (e.g., warfarin, aspirin, heparin, phenindione, fondaparinux, idraparinux, and thrombin inhibitors such as argatroban, lepirudin, bivalirudin, or dabigatran) an anti-inflammatory drug (e.g., corticosteroids, and non-steroidal anti-inflammatory drugs), an antihypertensive (e.g., an angiotensin converting enzyme inhibitor), an immunosuppressive agent (e.g., vincristine, cyclosporine A, or methotrexate), a fibrinolytic agent (e.g., ancrod, ε-aminocaproic acid, antiplasmin-a1, prostacyclin, and defibrotide), a lipid-lowering agent such as an inhibitor of hydroxymethylglutaryl CoA reductase (e.g., atorvastatin), an anti-CD20 agent such as rituximab, an anti-TNFα agent such as infliximab, an anti-seizure agent (e.g., magnesium sulfate), a C3 inhibitor, an anti-thrombotic agent, avacopan (CCX168; CAS #: 1346623-17-3), ravulizumab or zimura (avacincaptad pegol; CAS #1491144-00-3).

In an embodiment of the invention, the further therapeutic agent is an agent that inhibits an activity of C5; or C5 cleavage into C5a and C5b; or C5 expression. In an embodiment of the invention, the further therapeutic agent is C5 RNAi molecule or a polypeptide that binds to C5, e.g., a monoclonal antibody or peptide (e.g., cyclic peptide).

A further therapeutic agent that is administered to a subject in association with anti-C5 antibodies or antigen-binding fragments or polypeptides are, in an embodiment of the invention, administered to the subject in accordance with the Physicians' Desk Reference, e.g., Physicians' Desk Reference 2003 (Thomson Healthcare; 57$^{th}$ edition (Nov. 1, 2002)).

The further therapeutic agent may be administered to a subject sequentially or simultaneously with administration of the components of the combinations of the invention. "Simultaneous" administration refers to the administration (e.g., injection) of two or more substances in a single, common formulation or in separate formulations which are administered during the same treatment session. "Sequential" administration refers to administration of two or more substances during separate treatment sessions (substantially separated by time). For example, a first component may be deemed to be administered, in an sequential administration regimen, "prior to" a second component e.g., wherein the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, or 30 minutes before administration of the second component. In other embodiments, the additional therapeutically active component(s) may be administered to a subject after administration of an anti-C5 antibody of the present invention.

In an embodiment of the invention, the subject is further administered a therapeutic procedure, e.g., directed to the treatment of a C5-associated disease or disorder such as PNS or aHUS, e.g., dialysis, a blood or plasma transfusion or exchange and/or a bone marrow/stem cell transplant (BMT/SCT).

The present invention includes multispecific or multiparatopic antigen-binding proteins, as discussed herein, in association with a further therapeutic agent, e.g., as discussed herein (e.g., pharmaceutical compositions or kits thereof) as well as methods of using such proteins to treat or prevent a C5-associated disease or disorder, e.g., as discussed herein.

Kits

The present invention provides kits comprising one or more components of a combination of the present invention, optionally, in association with one or more further therapeutic agents, e.g., as discussed herein (e.g., H4H12166P and one of H4H12161P, H4H12170P, H4H12171P, H4H12175P, H4H12176P2 or H4H12177P2). In one embodiment of the invention, the kit includes an anti-C5 antigen-binding protein (e.g., antibody or antigen-binding fragment thereof) of the invention or a pharmaceutical composition thereof in one device (e.g., pre-filled syringe) or container (e.g., in a sterile glass or plastic vial) and another anti-C5 antigen-binding protein (e.g., antibody or antigen-binding fragment) of the invention or a pharmaceutical composition thereof in another device (e.g., pre-filled syringe) or container (e.g., in a sterile glass or plastic vial).

In another embodiment, the kit comprises a combination of the invention, including two or more anti-C5 antigen-binding proteins (e.g., antibodies or antigen-binding fragments) or a pharmaceutical composition thereof in a single, common container or device.

If the kit includes a pharmaceutical composition for parenteral administration to a subject, the kit can include a device for performing such administration. For example, the kit can include one or more hypodermic needles or other injection devices as discussed above. Thus, the present invention includes a kit comprising an injection device and one or more anti-C5 antigen-binding protein (e.g., antibodies or antigen-binding fragments thereof) of the present invention, e.g., wherein the injection device includes the antibody or fragment or wherein the antibody or fragment is in a separate vessel.

The kit can include a package insert including information concerning the pharmaceutical compositions and dosage forms in the kit. Generally, such information aids patients/subjects and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

The present invention includes methods for making a kit comprising a combination of the present invention. Such a method includes the steps of co-packaging the first anti-C5 antigen-binding protein (e.g., antibody or antigen-binding fragment); with the one or more of said further antigen-binding proteins (e.g., polypeptides, antibodies or antigen-binding fragments) into a kit. The method optionally includes the step of including one or more further therapeutic agents and/or other materials (e.g., as discussed herein) in the kit.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric. Any antibody combination or multispecific antibody set forth herein forms part of the present invention.

Example 1: Dual, but not Single, Anti C5 mAb Treatment Achieves Complete Inhibition of Alternative Complement Pathway Activation The ability of various anti-C5 antibodies, individually or in combination with other agents and under various conditions, to inhibit hemolysis was investigated.

Materials and Methods

Alternative pathway hemolysis assay. Alternative pathway hemolysis assay was used as the measure of complement activation to evaluate the ability of anti-C5 mAbs to block the lysis of rabbit red blood cells (RbRBCs). Lysis of rabbit red blood cells by membrane attack complex is the basis of the assay by which complement activation is experimentally measured.

A desired number of RbRBCs are washed in GVB-$Mg^{2+}$/EGTA buffer and resuspended at 2×10^8 cells/ml. To test the efficacy of either single anti-C5 mAb or a combination of anti-C5 mAbs, normal human serum was diluted to 50-96% in GVB-$Mg^{2+}$/EGTA buffer to achieve a final concentration of 25-48% when added to RBC. Round bottom 96 well plates were used to measure hemolysis activity. A total of 100 ul RbRBCs (2×10^8 cells/ml) were plated into 96-well plate at 37° C. followed by addition of 100 ul of diluted serum. Cells were gently mixed and incubated at 37° C. for 30-120 minutes. After incubation time, the cells were spun down by centrifugation at 1250×g at 4° C. A total of 100 uL of the supernatant was transferred to a fresh 96 flat bottom plate and read at 412 nm on a Spectramax microplate reader. The calculation of percent of hemolysis was done as described below.

The percentage of hemolysis was calculated with the absorbance values by using the following equation:

$$\% \text{ Hemolysis} = 100 \times \frac{(\text{Experimental Cell Lysis} - \text{Background Cell Lysis})}{(\text{Maximum Cell Lysis} - \text{Background Cell Lysis})}$$

In this equation "background cell lysis" was the OD at A412 nm from the cells incubated in GVB-$Mg^{2+}$/EGTA buffer only containing no serum. The "maximum cell lysis" was the OD at A412 nm from the cells treated with water. Maximum inhibition of lysis was calculated as a difference between bottom and top values in the curve expressed as a percentage of top value. Data was represented as mean±Standard error of mean.

Anti-C5 monoclonal antibodies tested. A panel of 12 anti-C5 mAbs were tested, which included H4H12166P, H4H12170P, H4H12171P, H4H12175P, H4H12177P2, H4H12176P2, H4H12161P, H4H12183P2, H4H12159P, H4H12164P, H4H12167P, and H4H12163P. A Fab version of H4H12170P was also evaluated in the assay.

Results

Figure 2A:
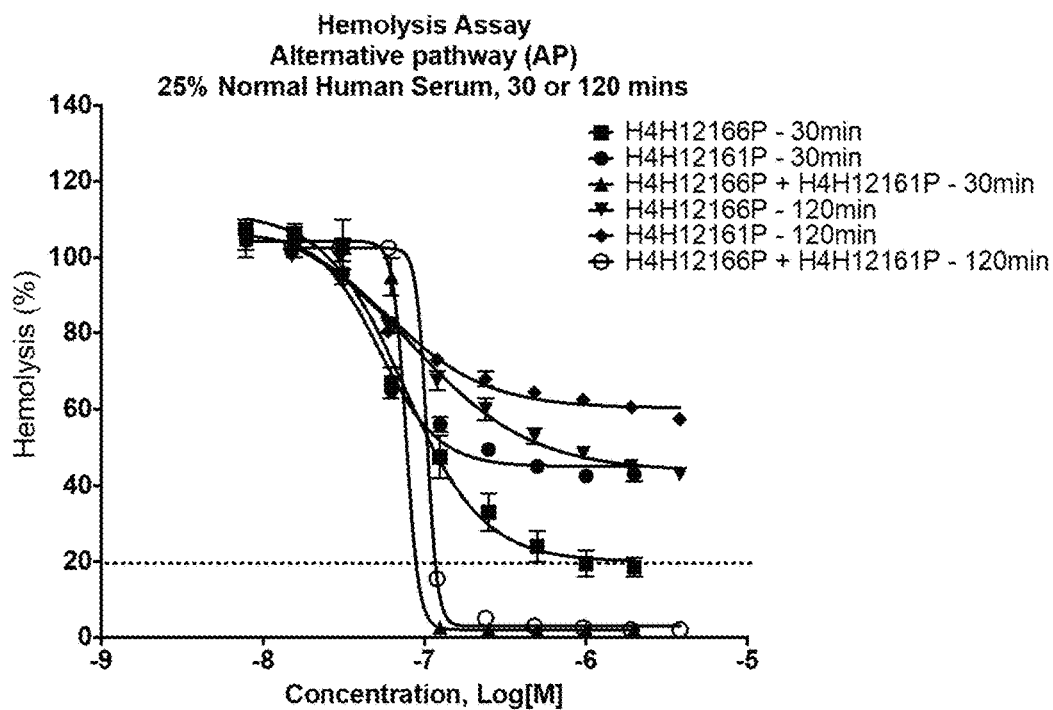
FIG. 2A is a graph showing hemolysis of red blood cells in the presence of 25% serum and H4H12166P, H4H12161P or H4H12166P+H4H12161P incubated for 30 or 120 minutes.
Figure 2B:
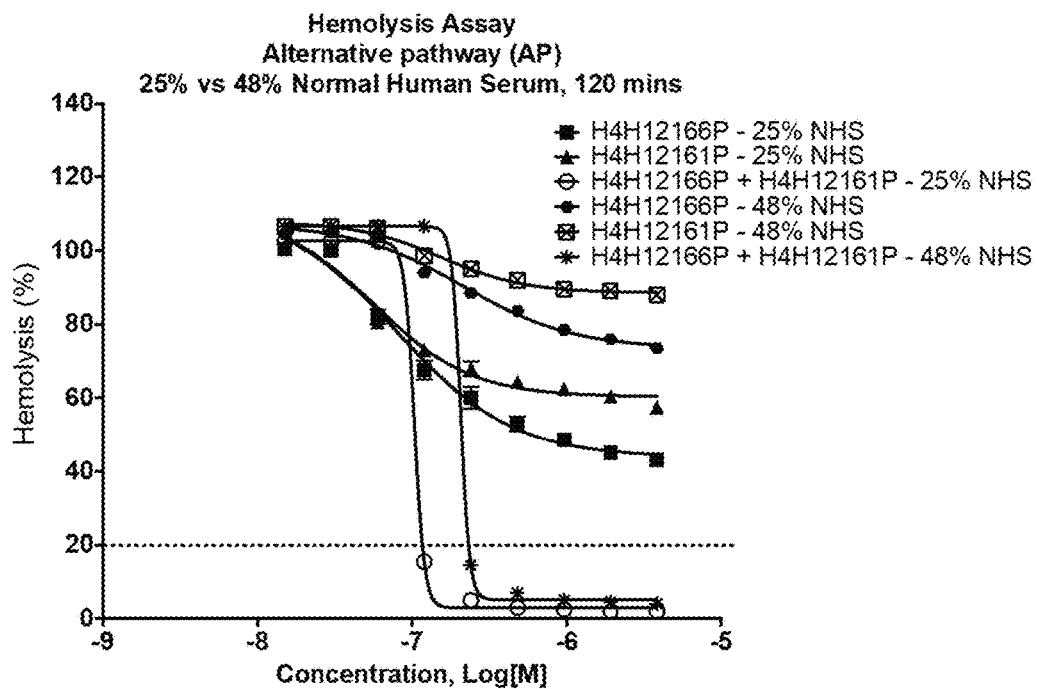
FIG. 2B is a graph showing hemolysis of red blood cells and H4H12166P, H4H12161P or H4H12166P+H4H12161P incubated for 120 minutes in the presence of 25% or 48% serum.

H4H12166P in combination with other anti-C5 mAbs completely block hemolysis of RbRBCs via alternative pathway activation. As shown in FIG. 1A and Table 2A, under standard assay conditions of 25% NHS (normal human serum) and 30 min incubation time, all single mAb treatments plateaued at around 80% inhibition (or less) of AP hemolysis. When used in a 1:1 molar ratio with H4H12166P, however, all combos blocked AP hemolysis down to essentially zero (FIG. 2B and Table 2B).

TABLE 2A

Red blood cell lysis in the presence of single antibodies.

| Antibody | % Max Inh. of Lysis |
| --- | --- |
| H4H12166P | 81.25 |
| H4H12170P | 88.66 |
| H4H12161P | 59.24 |
| H4H12171P | 36.63 |
| H4H12175P | 77.83 |
| H4H12176P2 | 62.80 |
| H4H12177P2 | 76.21 |

TABLE 2B

Red blood cell lysis in the presence of antibody combinations.

| Antibody Combinations | % Max Inh. of Lysis |
| --- | --- |
| H4H12166P + H4H12170P | 97.59 |
| H4H12166P + H4H12161P | 98.11 |
| H4H12166P + H4H12171P | 98.16 |
| H4H12166P + H4H12175P | 98.10 |
| H4H12166P + H4H12176P2 | 97.29 |
| H4H12166P + H4H12177P2 | 98.14 |

Inhibition with combination anti-C5 mAbs persists at high serum concentrations or longer incubation times. Increasing incubation time from 30 min to 120 min (FIG. 2A and Table 3A) or serum concentration from 25% to 48% (120 minute incubation) (FIG. 2B and Table 3B) both significantly decreased the efficacy of inhibition by single mAbs. However, H4H12166P, in combination with H4H12161P, was still able to fully block AP hemolysis despite higher serum concentrations or longer incubation times, demonstrating that blockade was robust and complete.

TABLE 3A

Red blood cell lysis in the presence of antibodies incubated for 30 or 120 minutes.

| | % Max Inh. of Lysis | |
| --- | --- | --- |
| Antibodies | 30 min | 120 min |
| H4H12166P | 82.79 | 57.21 |
| H4H12161P | 59.24 | 43.55 |
| H4H12166P + H4H12161P | 98.11 | 98.05 |

TABLE 3B

Red blood cell lysis in the presence of antibodies and 25 or 48% serum.

| | % Max Inh. of Lysis | |
| --- | --- | --- |
| Antibodies | 25% NHS 120 min | 48% NHS 120 min |
| H4H12166P | 57.21 | 30.00 |
| H4H12161P | 43.55 | 17.37 |
| H4H12166P + H4H12161P | 98.05 | 96.26 |

Figure 3:
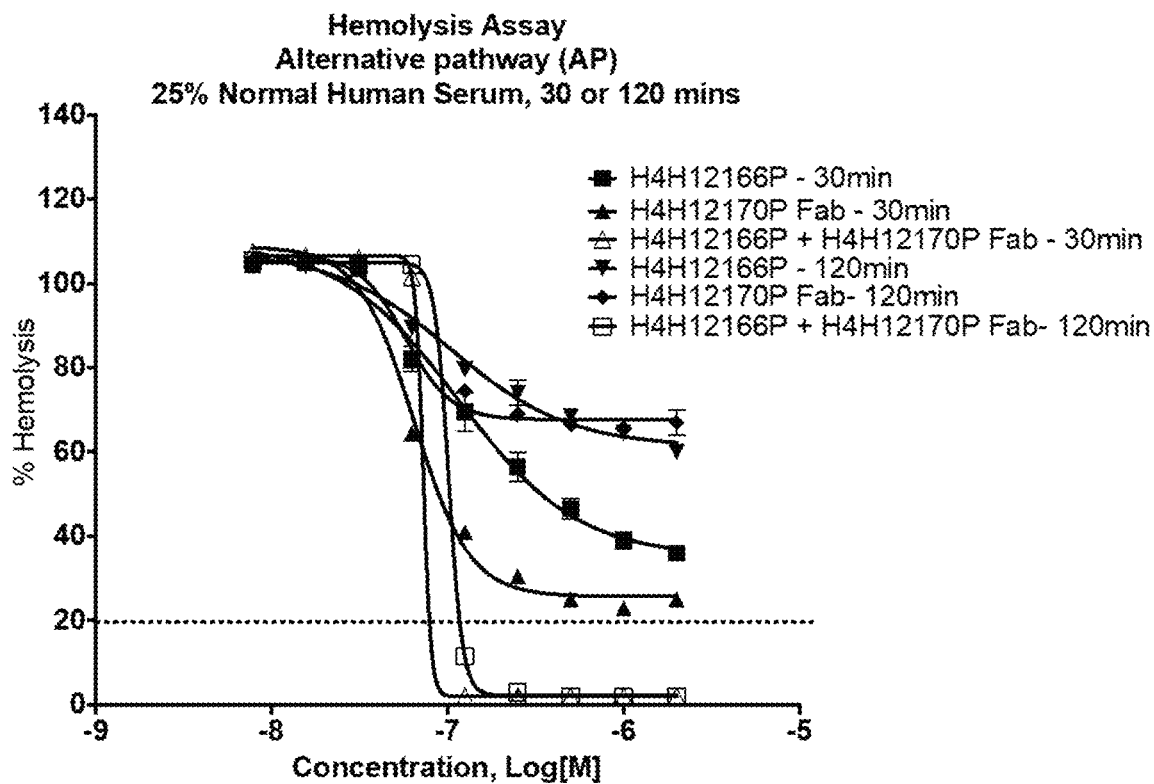
FIG. 3. Hemolysis of red blood cells in the presence of serum and H4H12166P; H4H12170P Fab or H4H12166P+H4H12170P Fab incubated for 30 or 120 minutes.
Figure 4:
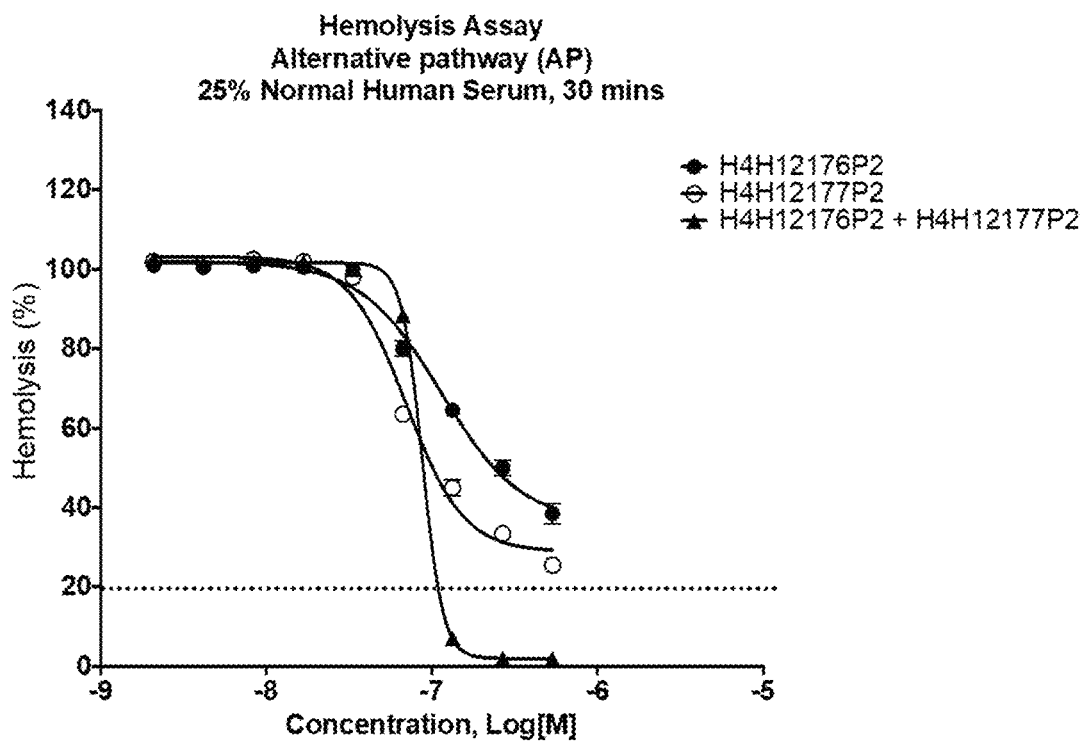
FIG. 4. Hemolysis of red blood cells in the presence of serum and H4H12176P2; H4H12177P2; or H4H12176P2+H4H12177P2 incubated for 30 minutes.
Figure 5A:
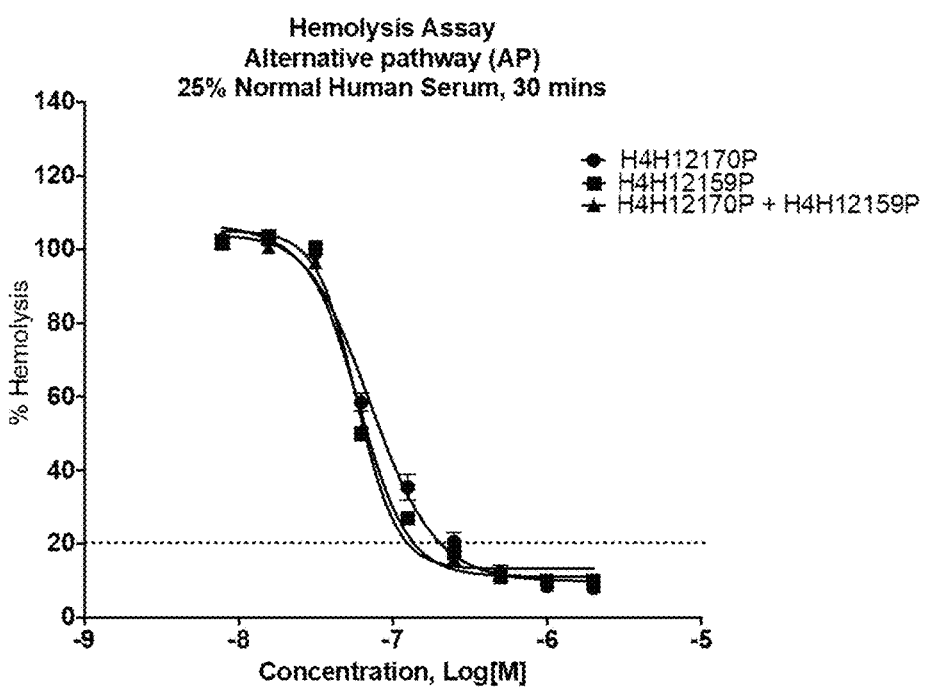
FIG. 5A is a graph showing hemolysis of red blood cells in the presence of serum and H4H12170P, H4H12159P; or H4H12170P+H4H12159P, incubated for 30 minutes.
Figure 5B:
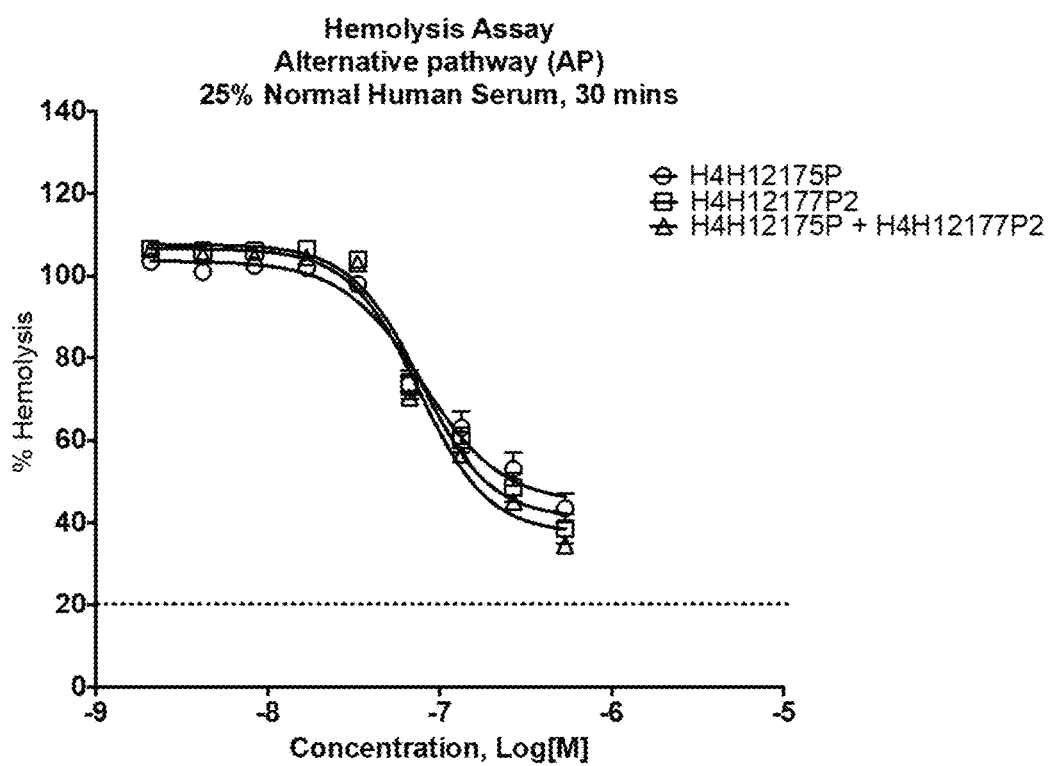
FIG. 5B is a graph showing hemolysis of red blood cells in the presence of serum and H4H12175P, H4H12177P2; or H4H12175P+H4H12177P2, incubated for 30 minutes.
Figure 5C:
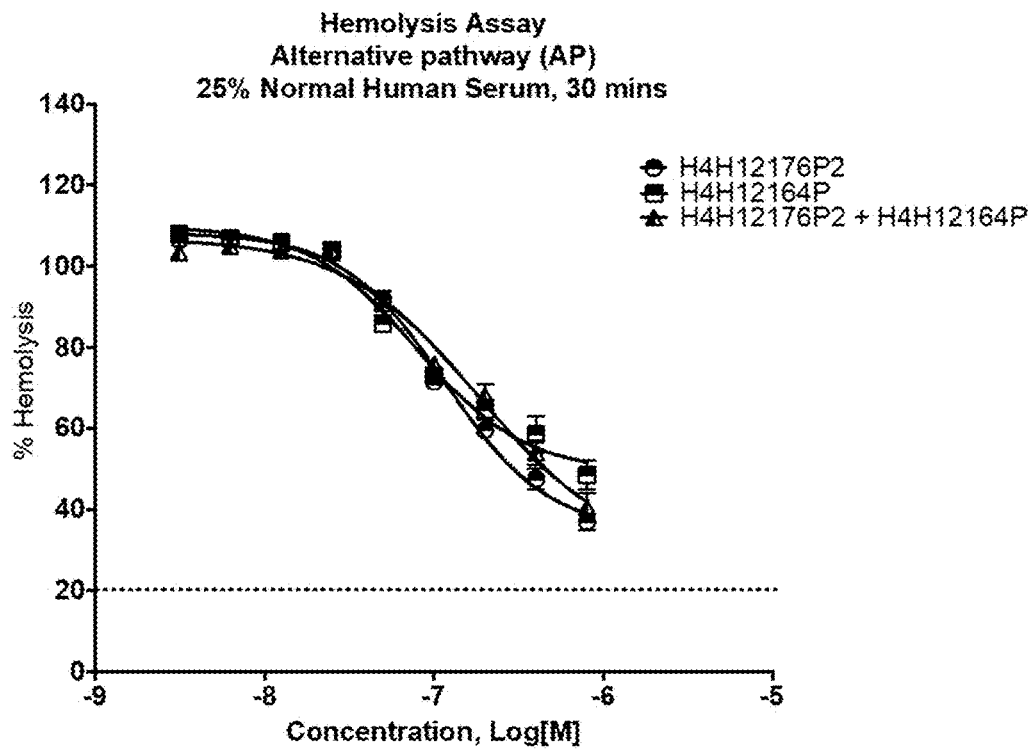
FIG. 5C is a graph showing hemolysis of red blood cells in the presence of serum and H4H12176P2, H4H12164P2; or H4H12176P2+H4H12164P2, incubated for 30 minutes.
Figure 5D:
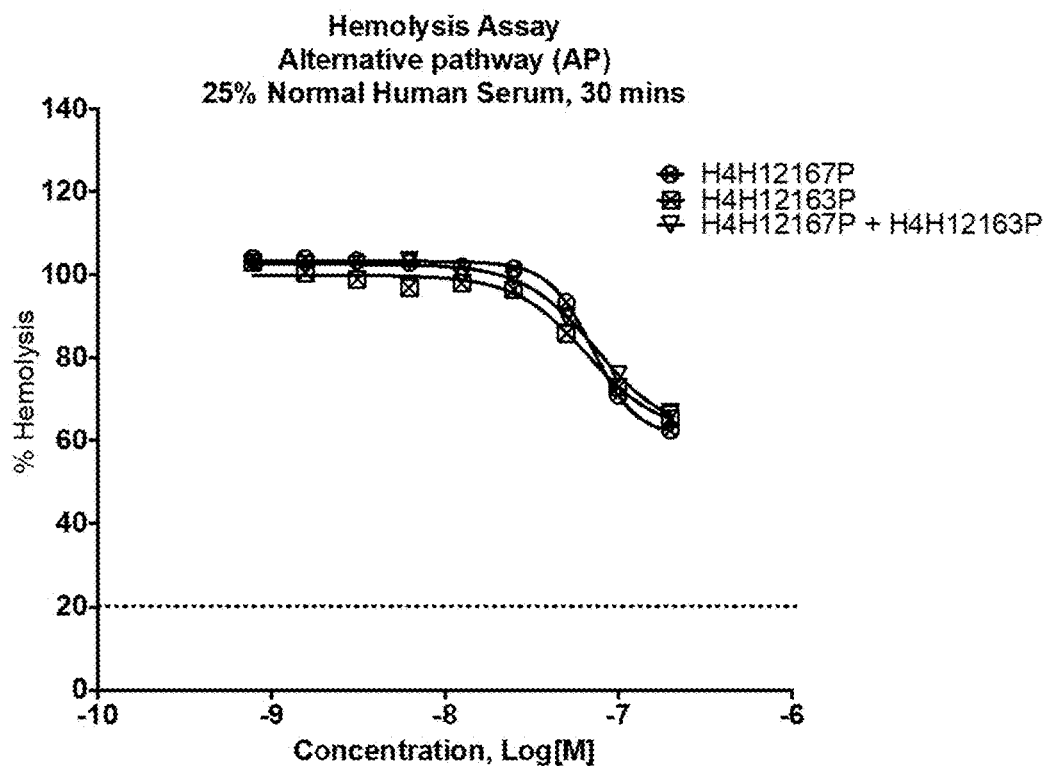
FIG. 5D is a graph showing hemolysis of red blood cells in the presence of serum and H4H12167P, H4H12163P; or H4H12167P+H4H12163P, incubated for 30 minutes.

Combo effect is also observed with a Fab not just mAbs, also is not dependent on H4H12166P, but requires the combination mAbs from different epitope bins. A Fab version of H4H12170P when used in a 2:1 molar ratio with H4H12166P, also achieved complete blockade at both 30 min and 120 min incubation times (FIG. 3 and Table 4). Next, whether H4H12166P was required for the observed combination effect was tested. As shown in FIG. 4 and Table 5, a different combination of antibodies, H4H12176P2 and H4H12177P2, also offered complete blockade of RbRBC hemolysis via alternative pathway showing the combination effect was independent of H4H12166P. However, as shown in FIG. 5, the maximal inhibition of hemolysis was not observed when testing combination mAbs from the same epitope bins (H4H12170P+H4H12159P, H4H12175P+H4H12177P2, H4H12176P2+H4H12164P, H4H12167P+H4H12163P) demonstrating that different binding sites were required for this observed effect.

TABLE 4

Red blood cell lysis in the presence of a Fab version of H4H12170P when used in a 2:1 molar ratio with H4H12166P.

| Antibodies | % Max Inh. of Lysis | |
|---|---|---|
| | 30 min | 120 min |
| H4H12166P | 65.88 | 42.31 |
| H4H12170P | 76.42 | 36.19 |
| H4H12166P 8 + H4H12170P | 98.14 | 98.10 |

TABLE 5

Red blood cell lysis in the presence of H4H12176P2 and/or H4H12177P2

| Antibodies | % Max Inh. of Lysis |
|---|---|
| H4H12176P2 | 61.88 |
| H4H12177P2 | 75.12 |
| H4H12176P2 + H4H12177P2 | 98.05 |

Figure 6:
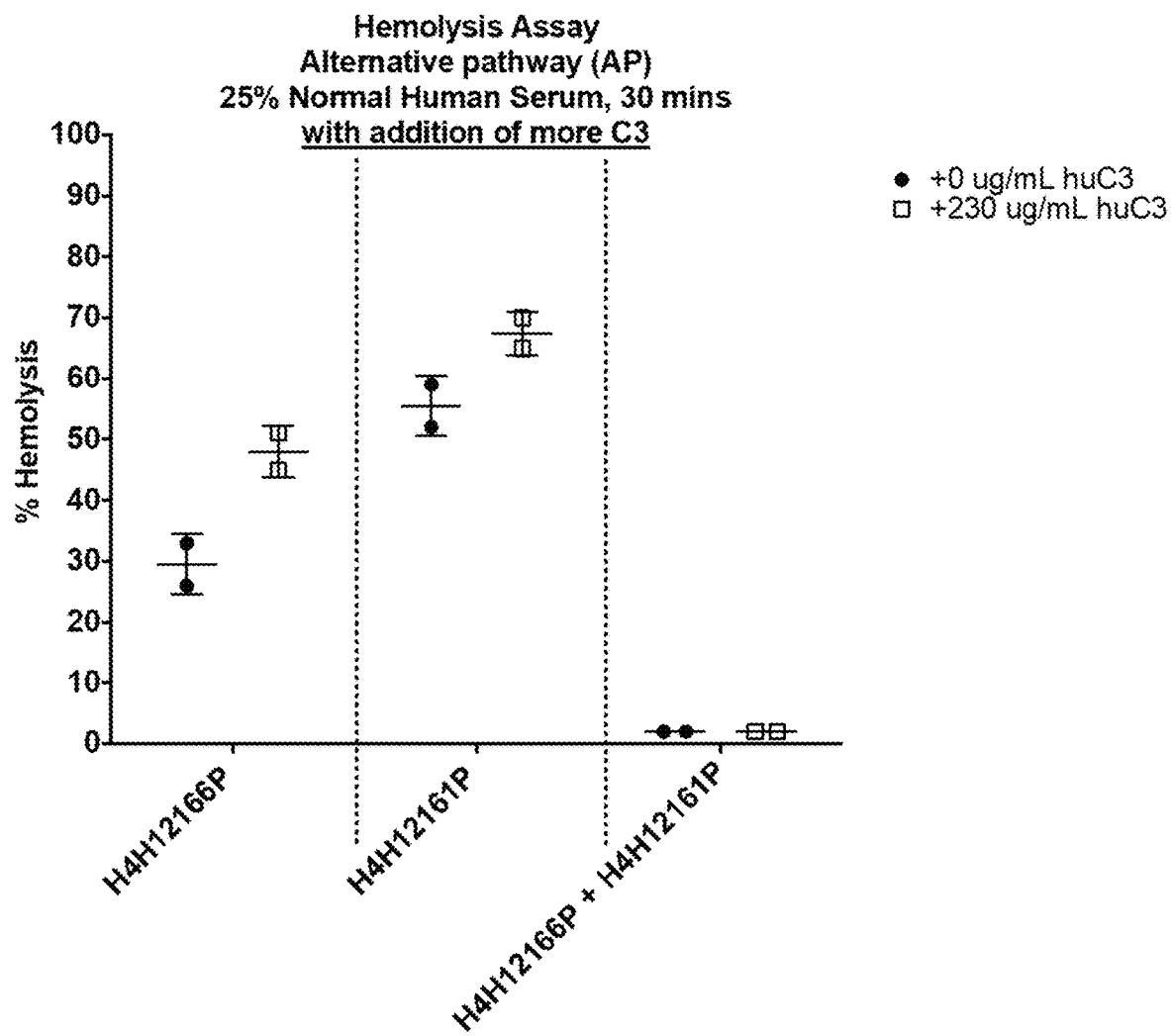
FIG. 6. Hemolysis of red blood cells in the presence of H4H12166P, H4H12161P alone or in combination with C3 protein.

Addition of C3 led to decreased blockade effect of single anti-C5, but not, combination mAbs. At 1 µM concentration with H4H12166P or H4H12161P mAbs, the addition of surplus human C3 protein resulted in partial recovery of AP activity in the single but not combination mAb condition, suggesting that addition of C3 overcame the effect of single, but not, combination of anti-C5 mAbs (FIG. 6).

Figure 7:
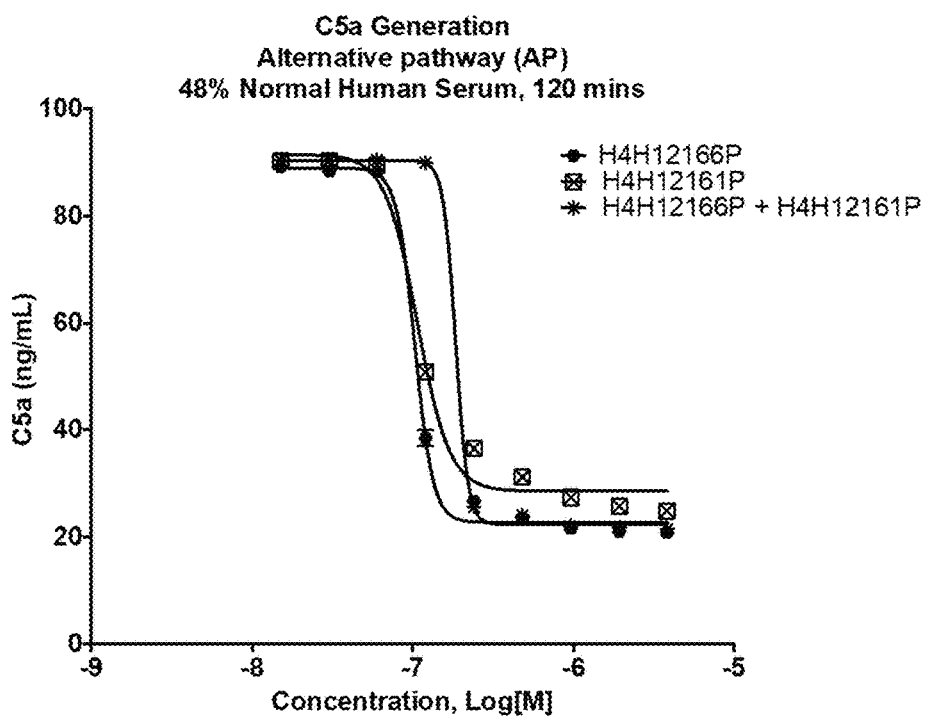
FIG. 7. Generation of C5a in the presence of H4H12166P; H4H12161P or H4H12166P+H4H12161P.

Inhibition with combination anti-C5 mAbs does not cause more suppression of C5a generation compared to single anti-C5 mAb. As shown in FIG. 7, the blockade effects on C5a generation does not appear to be different between single (H4H12166P or H4H12161P) and combination anti-C5 mAbs (H4H12166P+H4H12161P).

Example 2: A C5 Bispecific Antibody Achieves Complete Inhibition of Alternative Complement Pathway Activation Similar to Combination of Anti-C5 mAbs Alternative pathway hemolysis assay was used as the measure of complement activation to evaluate the ability of anti-C5 mAbs to block the lysis of rabbit red blood cells (RbRBCs). Lysis of rabbit red blood cells by membrane attack complex is the basis of the assay by which complement activation is experimentally measured.

A desired number of RbRBCs were washed in GVB-$Mg^{2+}$/EGTA buffer and resuspended at $2 \times 10^8$ cells/ml. To test the efficacy of either single anti-C5 mAb or a combination of anti-C5 mAbs, normal human serum was diluted to 50-96% in GVB-$Mg^{2+}$/EGTA buffer to achieve a final concentration of 25-48% when added to RBC. Round bottom 96 well plates were used to measure hemolysis activity. A total of 100 ul RbRBCs ($2 \times 10^8$ cells/ml) were plated into 96-well plate at 37° C. followed by addition of 100 ul of diluted serum. Cells were gently mixed and incubated at 37° C. for 30-120 minutes. After incubation time, the cells were spun down by centrifugation at 1250×g at 4° C. A total of 100 uL of the supernatant was transferred to a fresh 96 flat bottom plate and read at 412 nm on a Spectramax microplate reader. The calculation of percent of hemolysis was done as described below.

The percentage of hemolysis was calculated with the absorbance values by using the following equation:

$$\% \text{ Hemolysis} = 100 \times \frac{(\text{Experimental Cell Lysis} - \text{Background Cell Lysis})}{(\text{Maximum Cell Lysis} - \text{Background Cell Lysis})}$$

In this equation, "background cell lysis" was the OD at $A_{412nm}$ from the cells incubated in GVB-$Mg^{2+}$/EGTA buffer only containing no serum. The "maximum cell lysis" was the OD at $A_{412nm}$ from the cells treated with water. Maximum inhibition of lysis was calculated as a difference between bottom and top values in the curve expressed as a percentage of top value. Data are represented as mean±Standard error of mean.

For the experiments to examine the molar ratio of mAb/C5, a fixed concentration of 125 or 145 nM of C5 (purchased from CompTech Inc.) was added to the C5-deficient normal human serum (purchased from CompTech Inc.) and titrated against various concentration of antibodies before testing in alternative pathway hemolysis assay.

Anti-C5 monoclonal antibodies tested:
H412176P2
H412177P2
A bispecific antibody made from H412176P2 and H412177P2 ("H412176P2xH412177P2")

Figure 8:
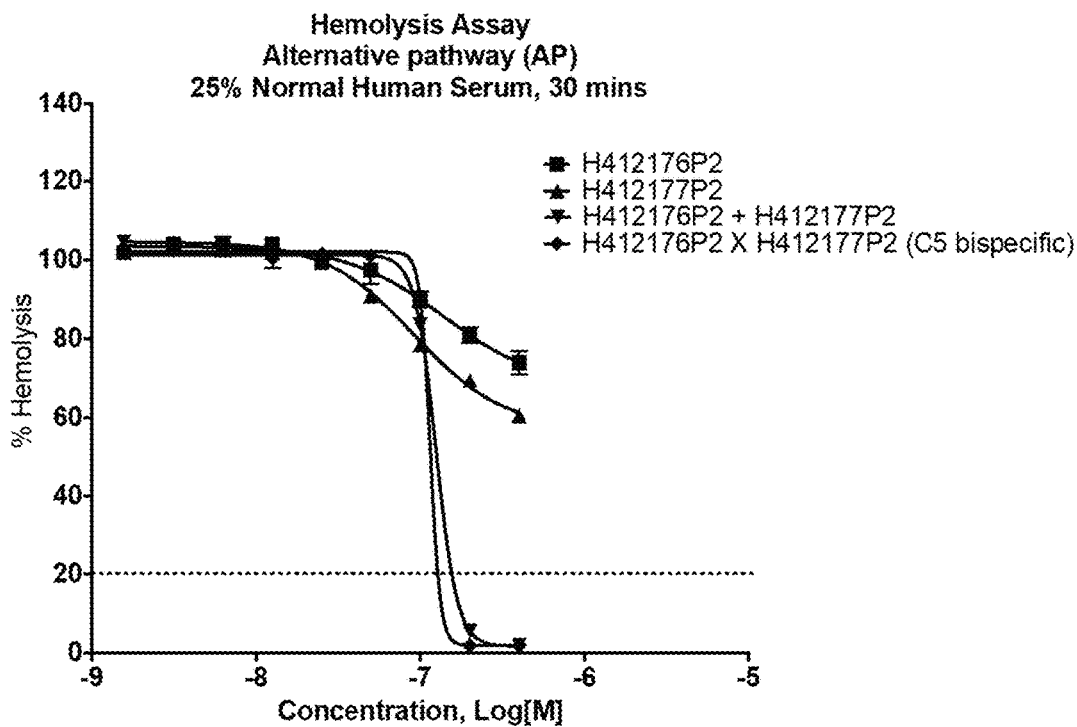
FIG. 8. Hemolysis assay; alternative complement pathway with 25% normal human serum incubated for 30 minutes.

H412176P2xH412177P2, a C5 bispecific antibody, completely blocked hemolysis of RbRBCs via alternative pathway activation. As shown in FIG. 8 and Table 6, under standard assay conditions of 25% NHS and 30 min incubation times, a single mAb treatment of H412176P2 or H412177P2 led to partial inhibition of AP hemolysis. When used in a 1:1 molar ratio, a combination of H412176P2+H412177P2, however, blocked AP hemolysis down to essentially zero. H412176P2xH412177P2, a bispecific antibody made from the heavy and light Ig chains of H412176P2 and H412177P2, also showed complete suppression of AP hemolysis similar to the combination of mAbs.

TABLE 6

Percentage of lysis inhibition

| ABPID | % Max Inh. of Lysis |
|---|---|
| H4H12176P2 | 27.45 |
| H4H12177P2 | 42.65 |
| H4H12176P2 + H4H12177P2 | 98.10 |
| H412176P2 × H412177P2 | 98.06 |

Figure 9:
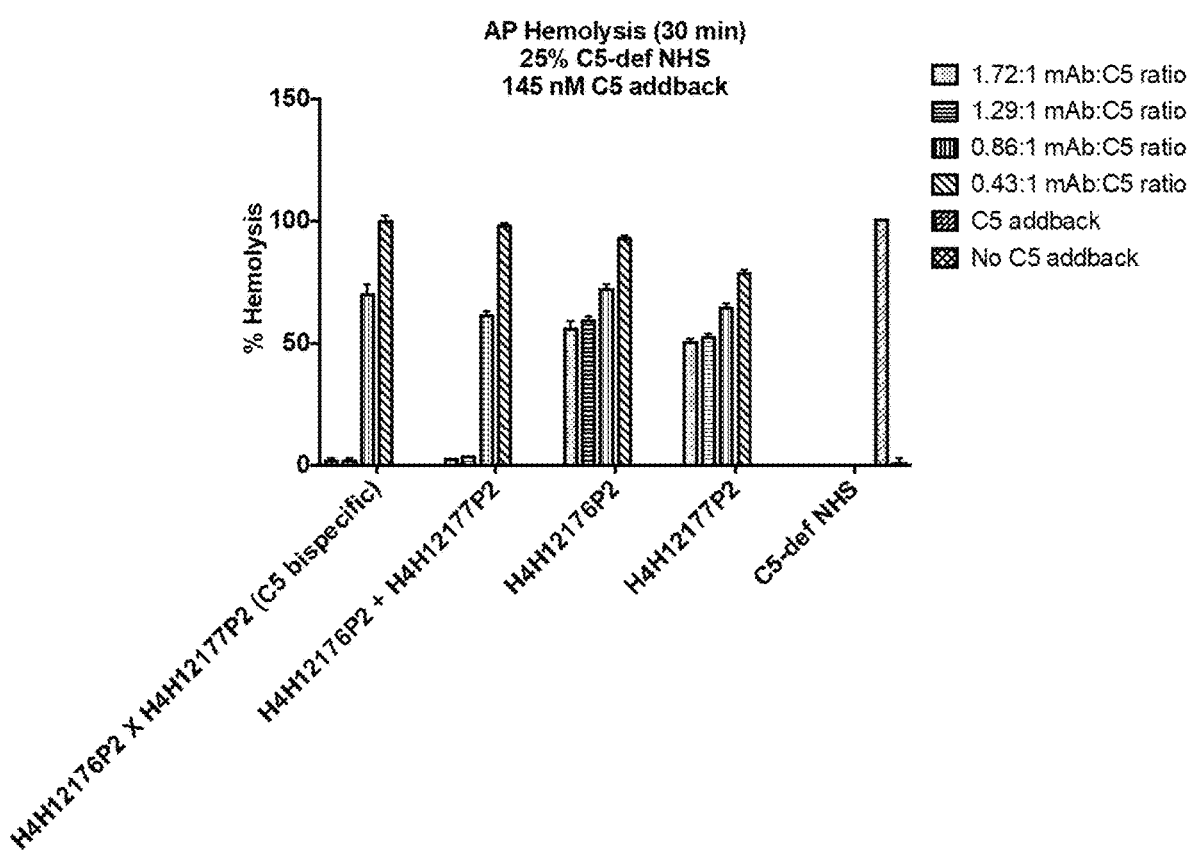
FIG. 9. Hemolysis assay; alternative complement pathway with 25% C5-deficient normal human serum; 145 nM C5 add-back and various ratios of antibody to C5.
Figure 10A:
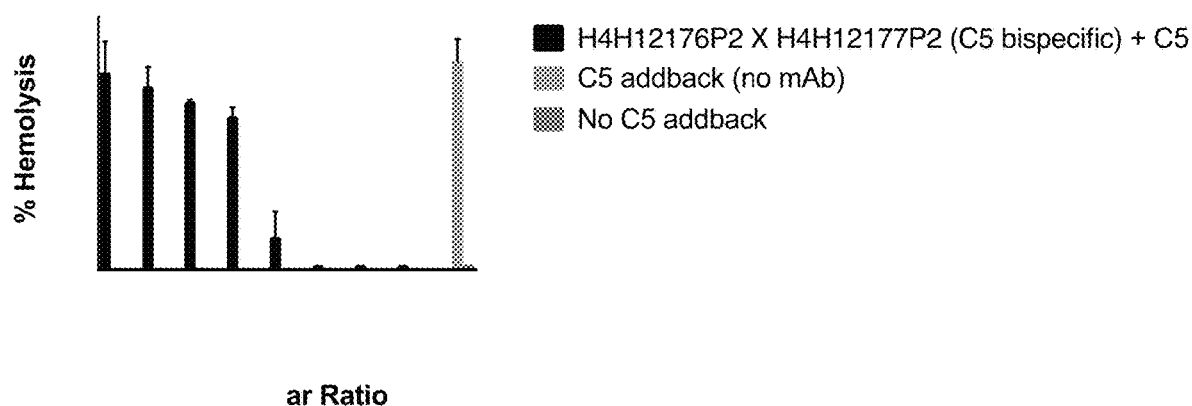
FIG. 10A and FIG. 10B are graphs showing hemolysis assay; alternative complement pathway with 25% C5-deficient normal human serum; 125 nM C5 add-back and various ratios of bispecific anti-C5 antibody to C5.
Figure 10B:
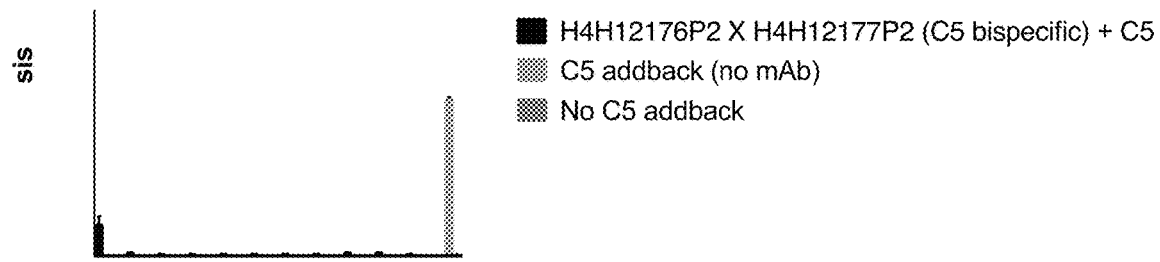

Near molar equivalent of combination of antibodies or C5-bispecific is enough to completely block hemolysis of RbRBCs via alternative pathway activation. As shown in FIG. 9, a mAb/C5 ratio of about 1.29 of either combination mAbs (H412176P2+H412177P2) or C5 bispecific (H412176P2xH412177P2) blocked hemolysis to close to zero. Individual mAbs at this ratio, or even above, offered only partial inhibition. Further experiments with H412176P2xH412177P2 showed a mAb/C5 ratio between 1.0-1.5 completely blocked alternative pathway hemolysis assay (FIGS. 10A and 10B).

Example 3: Size Analysis of In Vitro Complexes Formed Between hC5 and Anti-hC5 Monoclonal Antibodies (mAbs) by Asymmetrical Flow Field-Flow Fractionation Coupled to Multi-Angle Laser Light Scattering (A4F-MALLS)

The A4F-MALLS system is composed of an Eclipse™ 3+A4F Separation System coupled to an Agilent 1200 Series HPLC system equipped with a ultraviolet (UV) diode array detector, Wyatt Technology Dawn HELEOS® II laser light scattering instrument (LS), and an Optilab® T-rEX differential refractometer (RI) detector. The detectors were connected in series in the following order: UV-LS-RI. LS and RI detectors were calibrated according to instructions provided by Wyatt Technology.

Defined amounts of anti-hC5 mAbs were each combined with human complement C5 (hC5; EMD Millipore) and diluted in 1×DPBS, pH 7.4 to yield the final molar ratios listed in Table 7. All samples were incubated at ambient temperature for 2 hours and maintained unfiltered at 4° C. prior to injection into an Eclipse™ short channel fitted with a W350 spacer foil (350 µm spacer thickness, 2.2 cm spacer width) and using a 10 kDa MWCO Nadir regenerated cellulose membrane. The channel was pre-equilibrated with the mobile phase buffer (10 mM sodium phosphate, 500 mM sodium chloride, pH 7.0±0.1), prior to the injection of each sample. Bovine serum albumin (BSA; 2 mg/mL; 10 µg sample load) was injected separately and included as a system suitability control.

The fractionation method consisted of four steps: injection, focusing, elution, and a channel "wash-out" step. The A4F-MALLS mobile phase buffer (10 mM sodium phosphate, 500 mM sodium chloride, pH 7.0±0.1) was used throughout the fractionation method. Each sample (7 µg total protein load) was injected at a flow rate of 0.2 mL/min for 1 min and subsequently focused for 2 min with a focus flow rate of 1.5 mL/min. The sample was eluted with a channel flow rate of 1.0 mL/min and a linear gradient cross flow from 3.0 mL/min to 0 mL/min over 45 min. Finally, the cross flow was held at 0 mL/min for an additional 5 min to wash out the channel. BSA was fractionated using the same parameter settings.

TABLE 7

Concentrations of Each Component for Sample Preparation

| Sample | mAb1:mAb2:hC5 Molar Ratio (µM:µM:µM) | Figure | Table |
|---|---|---|---|
| H4H12166P:hC5 | 1:1 | 11 | 9 |
| H4H12166P:H4H12175P:hC5 | 0.5:0.5:1 | 12 | 10 |
| H4H12166P:H4H12177P2:hC5 | 0.5:0.5:1 | 12 | 10 |
| H4H12166P:H4H12161P:hC5 | 0.5:0.5:1 | 13 | 10 |
| H4H12166P:H4H12176P2:hC5 | 0.5:0.5:1 | 13 | 10 |
| H4H12176P2:H4H12177P2:hC5 | 0.5:0.5:1 | 13 | 10 |
| H4H12166P:H4H12170P:hC5 | 0.5:0.5:1 | 14 | 10 |
| H4H12166P:H4H12171P:hC5 | 0.5:0.5:1 | 15 | 10 |
| H4H12176P2 × H4H12177P2 bispecific Ab:hC5 | 3:1 | 16 | 11 |
| H4H12176P2 × H4H12177P2 bispecific Ab:hC5 | 1:1 | 16 | 11 |
| H4H12176P2 × H4H12177P2 bispecific Ab:hC5 | 1:3 | 16 | 11 |

A4F-MALLS Data Analysis. Data were analyzed using ASTRA V software (version 5.3.4.14, Wyatt Technology). The data were fit to the equation that relates the excess scattered light to the solute concentration and weight-average molar mass, Mw, (Kendrick E S, Kerwin B A, Chang E S, Philo J S. (2001). Anal Biochem. 299(2), 136-46, "Online Size-Exclusion High-Performance Liquid Chromatography Light Scattering and Differential Refractometry Methods to Determine Degree of Polymer Conjugation to Proteins and Protein-Protein or Protein-Ligand Association States"; Wyatt, P J. (1993) Anal. Chim. Acta 272(1), 1-40, "Light Scattering and the Absolute Characterization of Macromolecules"):

$$\frac{K*c}{R(\theta,c)} = \frac{1}{MwP(\theta)} + 2A_2c \qquad \text{Equation 1}$$

where c is the solute concentration, R(θ,c) is the excess Raleigh ratio from the solute as a function of scattering angle and concentration, Mw is the molar mass, P(θ) describes the angular dependence of scattered light (~1 for particles with radius of gyration <50 nm), $A_2$ is the second virial coefficient in the expansion of osmotic pressure (which can be neglected since measurements are performed on dilute solutions) and K* is defined by Equation 2:

$$K* = \frac{4\pi^2 n_0^2}{N_A \lambda_0^4}\left(\frac{dn}{dc}\right)^2 \qquad \text{Equation 2}$$

where $n_o$ represents the solvent refractive index, $N_A$ is Avogadro's number, Xo is the wavelength of the incident light in a vacuum, and dn/dc represents the specific refractive index increment for the solute.

The normalization coefficients for the light scattering detectors, inter-detector delay volume and band broadening terms were calculated from the BSA chromatograms collected for the A4F-MALLS condition employed. These values were applied to the data files collected for all other samples to correct for these terms.

The dn/dc value and the extinction coefficient at 215 nm (corrected for glycosylation) were experimentally determined using the protein conjugate analysis provided in the Astra software. The corrected extinction coefficient and dn/dc value was used to analyze all protein-protein complex samples. The molar mass of BSA monomer served to evaluate the calibration constants of the light scattering and differential refractive index detectors during data collection (system suitability check). The relative standard deviation of the average molar mass of BSA determined from the UV and RI detectors was ≤5.0%.

A4F-MALLS was used to assess the relative size distribution of complexes formed between anti-hC5 antibodies and hC5. The theoretical molar mass of potential mAb:hC5 complexes along with their predicted stoichiometry is provided in Table 8.

Figure 11:
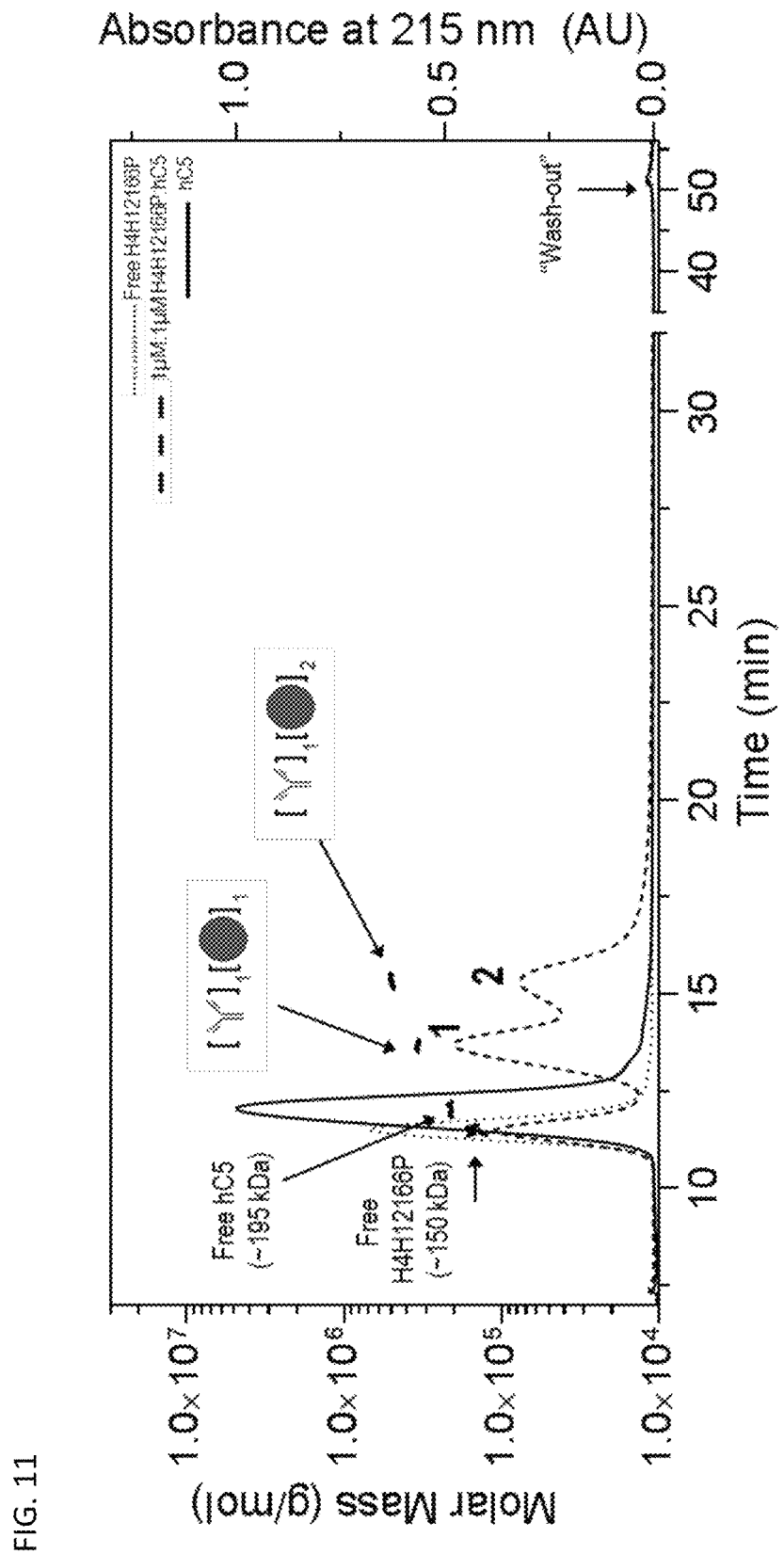
FIG. 11. A4F-MALLS analysis of H4H12166P:C5 complexes (mAb:C5::1 µm: 1 µm ratio) in the absence of a secondary antibody.
Figure 12:
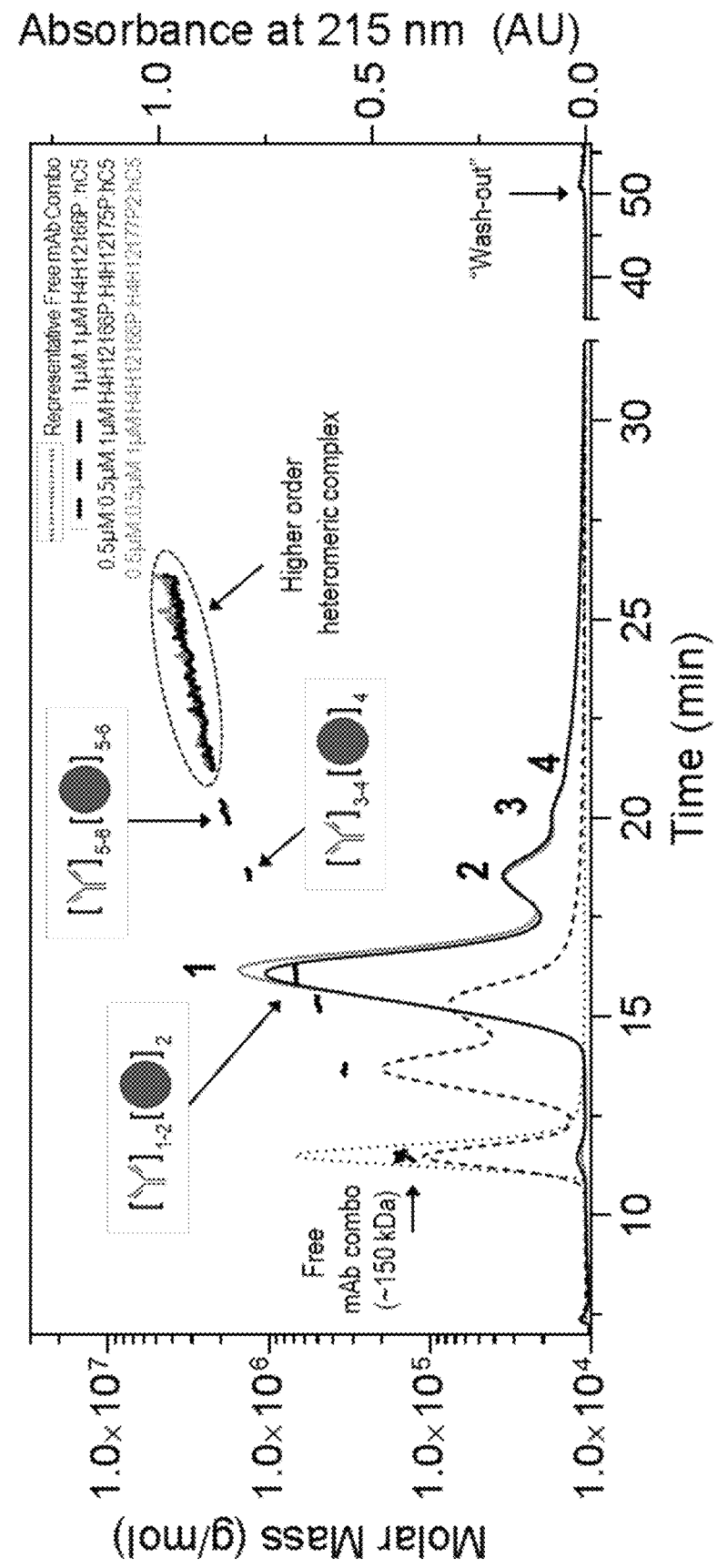
FIG. 12. A4F-MALLS analysis of H4H12166P:C5 complexes with secondary antibodies (mAb2), H4H12175P or H4H12177P2 (mAb1:mAb2:C5::0.5 µm:0.5 µm:1 µm ratio).
Figure 13:
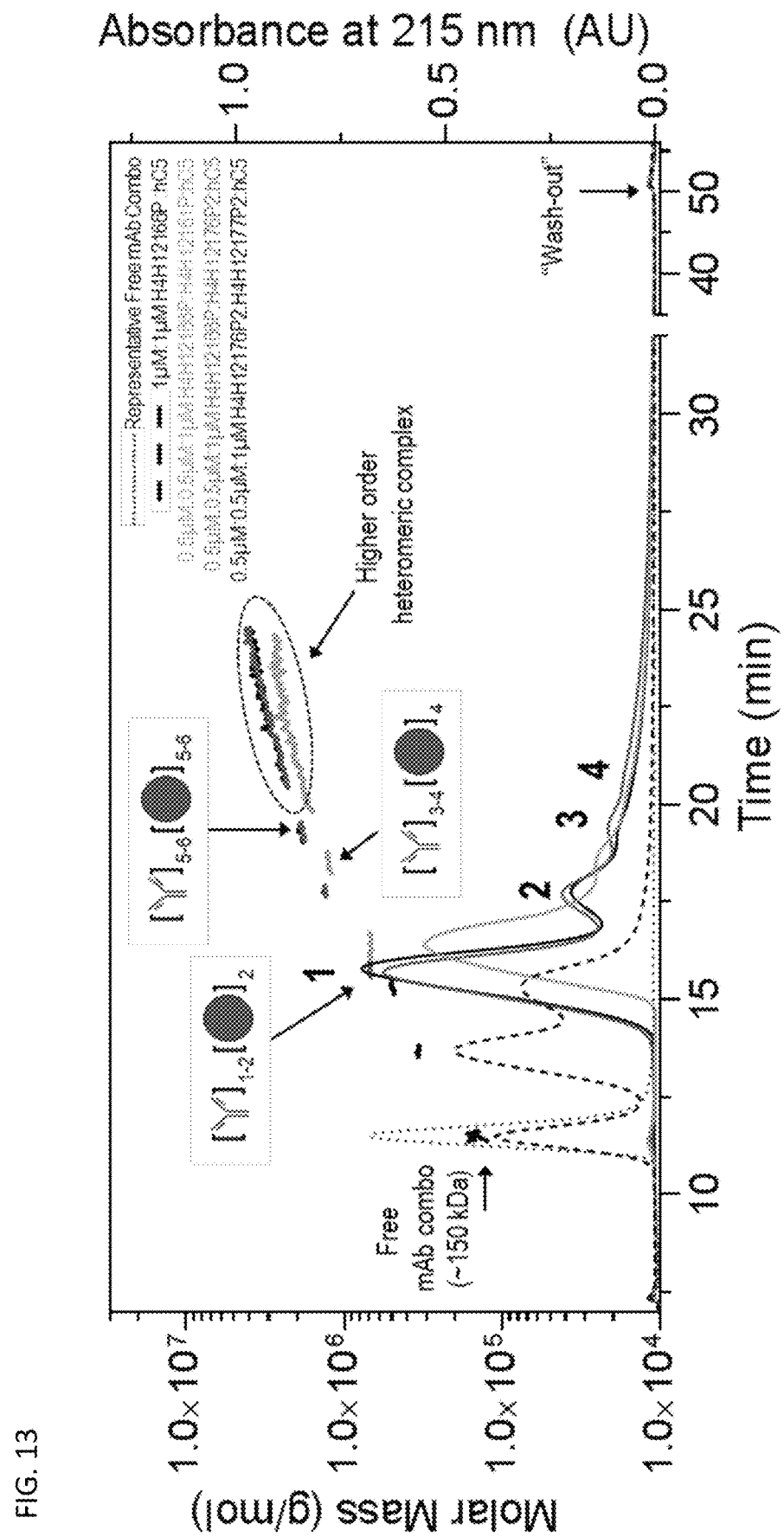
FIG. 13. A4F-MALLS analysis of H4H12166P: H4H12161P:hC5; H4H12166P: H4H12176P2:hC5; and H4H12176P2: H4H12177P2:hC5 complexes (mAb1:mAb2:C5::0.5 µm:0.5 µm:1 µm ratio).
Figure 14:
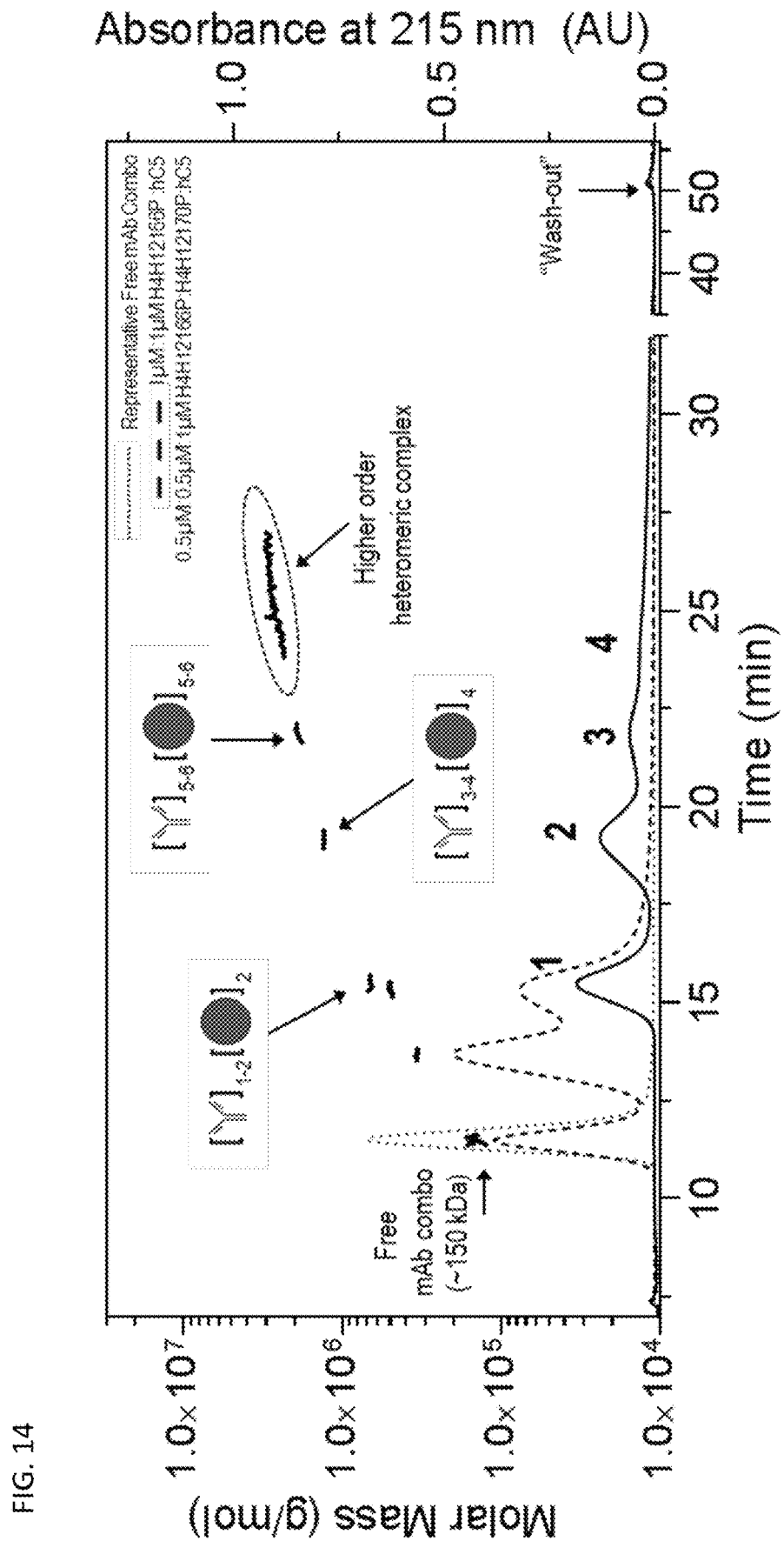
FIG. 14. A4F-MALLS analysis of H4H12166P:C5 complexes with secondary antibody, H4H12170P (mAb1:mAb2:C5::0.5 µm:0.5 µm:1 µm ratio).
Figure 15:
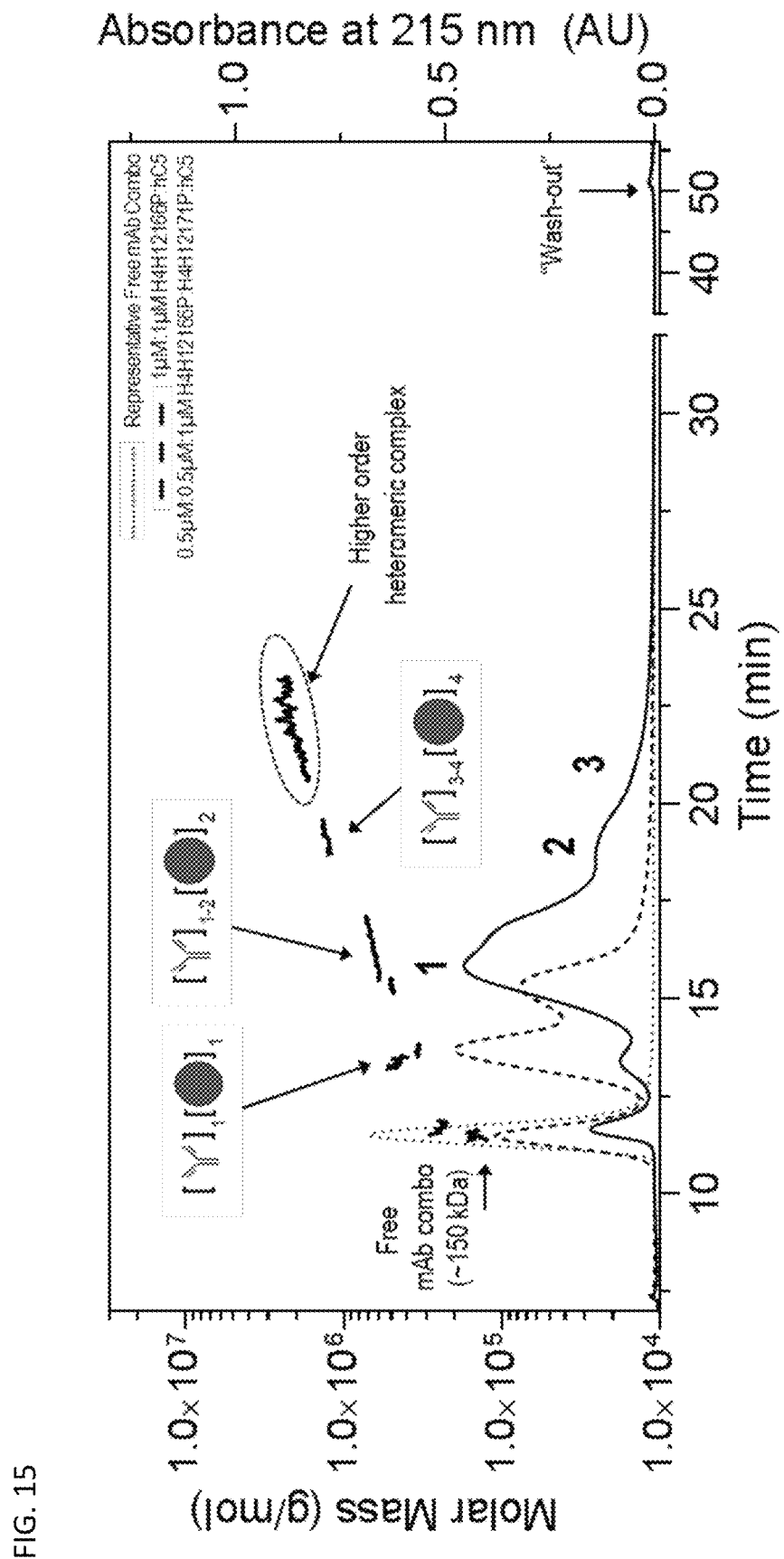
FIG. 15. A4F-MALLS analysis of H4H12166P:C5 complexes with secondary antibody, H4H12171P (mAb1:mAb2:C5::0.5 µm:0.5 µm:1 µm ratio).
Figure 16:
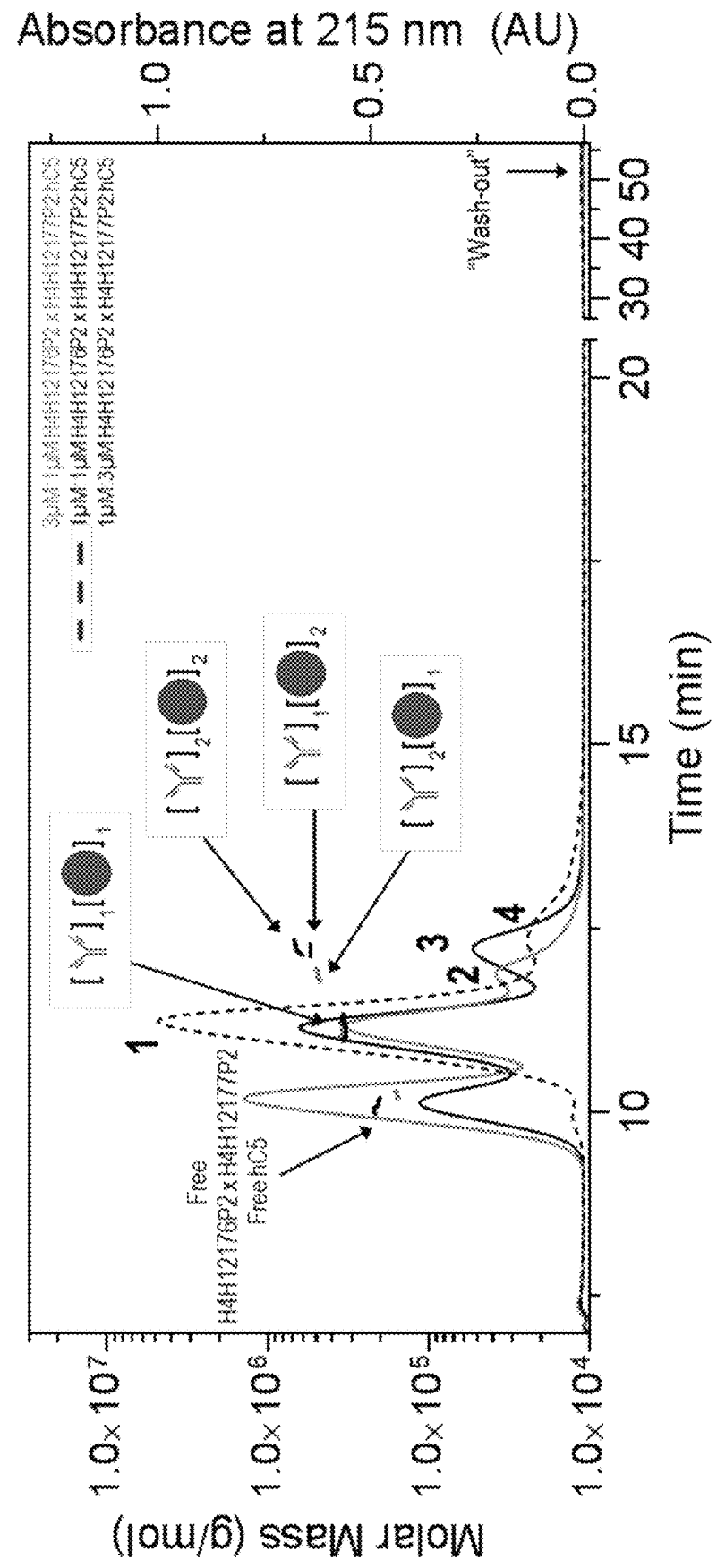
FIG. 16. A4F-MALLS analysis of H4H12176P2xH4H12177P2:C5 complexes at various ratios (mAb:C5::3:1, 1:1 or 1:3).

Initial screening of anti-hC5 mAb combinations highlight differences in size distribution of complexes formed with hC5. In the absence of secondary mAbs, H4H12166P formed canonical 1:1 and 1:2 complexes with hC5 when mixed in equimolar amounts (FIG. 11, Table 9). Overall, all mAb combinations examined exhibited the ability to form heteromeric complexes with hC5, with most combinations favoring a smaller, discrete species consistent with a 2:2 mAb:hC5 heteromeric complex under the conditions tested (Peak 1, FIGS. 12 and 13; Table 10). Although minor amounts of larger, discrete complexes could also be detected in these samples (Peak 2), formation of very large, heterogeneous, extended antibody-antigen lattices (≥~1500 kDa; Peaks 3-4)—a process termed "paper-dolling"—was limited. In contrast, combinations of H4H12166P with H4H12170P favored larger, more heterogeneous complexes with hC5 indicative of a higher degree of "paper-dolling" compared to other combinations tested (FIG. 14; Table 10). Finally, combinations of H4H12166P and H4H12171P displayed a reduced tendency to form heteromeric complexes with hC5 as evidenced by the presence of free mAb and 1:1 mAb:hC5 homomeric complex (*) detected in this sample (FIG. 15; Table 10). This may suggest that the binding of one mAb influences the affinity (and/or off-rate) of the other for hC5 in this combination. Alternatively, this may indicate a reduced stability of the heteromeric complexes in this sample during the fractionation process compared to the other combinations tested.

Analysis of complexes formed between H412176P2xH412177P2 (bispecific anti-hC5 mAb) and hC5 revealed a stable 1:1 H412176P2xH412177P2:hC5 complex was favored under all conditions. When mixed at various molar ratios, H412176P2xH412177P2 bispecific antibody predominantly forms a stable 1:1 complex with hC5 suggesting that both arms of the H412176P2xH412177P2 prefer to engage a single molecule of hC5-termed a monogamous, bivalent interaction (FIG. 16; Table 11). While minor amounts of additional discrete complexes consistent with 1:2, 2:1, and 2:2 mAb:hC5 could be detected under various conditions, no additional higher order complexes were observed indicating that H412176P2xH412177P2 does not promote "paper-dolling" with hC5.

TABLE 8

Theoretical Molar Mass of mAb:hC5 Complexes

| mAb:hC5 Complex | Theoretical Molar Mass (kDa) |
|---|---|
| 1:0 | 150 |
| 0:1 | 195 |
| 1:1 | 345 |
| 2:1 | 495 |
| 1:2 | 540 |
| 2:2 | 690 |
| 3:2 | 840 |
| 2:3 | 885 |
| 3:4 | 1230 |
| 4:4 | 1380 |
| 5:5 | 1725 |
| 6:5 | 1875 |
| 5:6 | 1920 |
| 6:6 | 2070 |

TABLE 9

Summary Table of Approximate Molar Mass and Retention Time of hC5 Complexes with H4H12166P Alone

| Sample | Molar Ratio (μM:μM) | Peak 1 [mAb]$_1$:[hC5]$_1$ Complex | | Peak 2 [mAb]$_1$:[hC5]$_2$ Complex | |
|---|---|---|---|---|---|
| | | $R_t$, min | $M_w$, kDa | $R_t$, min | $M_w$, kDa |
| H4H12166P:hC5 | 1:1 | 13.7 | 341.1 | 15.3 | 498.7 |

$R_t$: Retention Time;
$M_w$: weight average molar mass;
min: minutes;
kDa: kiloDaltons;

TABLE 10

Summary Table of Approximate Molar Mass and Retention Time of hC5 Complexes with Anti-hC5 mAb Combinations

| Sample | Molar Ratio (μM:μM:μM) | Peak 1 [mAb]$_{1-2}$:[hC5]$_2$ Complex | | Peak 2 [mAb]$_{3-4}$:[hC5]$_4$ Complex | | Peak 3 [mAb]$_{5-6}$:[hC5]$_{5-6}$ Complex | | Peak 4 Higher Order Heteromeric Complexes ([mAb]$_{\geq 7}$:[hC5]$_{\geq 7}$) | |
|---|---|---|---|---|---|---|---|---|---|
| | | $R_t$, min | $M_w$, kDa | $R_t$, min | $M_w$, kDa | $R_t$, min | $M_w$, kDa | $R_t$, min | $M_w$, kDa |
| H4H12166P:H4H12175P:hC5 | 0.5:0.5:1 | 16.0 | 684.4 | 18.5 | 1342.4 | 20.1 | 1876.0 | 21.5 | ~2250-3560 |
| H4H12166P:H4H12177P2:hC5 | 0.5:0.5:1 | 16.1 | 687.7 | 18.5 | 1327.4 | 20.1 | 1865.6 | 21.5 | ~2380-4250 |
| H4H12166P:H4H12161P:hC5 | 0.5:0.5:1 | 16.4 | 684.7 | 18.4 | 1261.8 | NA | NA | 20.2 | ~1700-2700 |
| H4H12166P:H4H12176P2:hC5 | 0.5:0.5:1 | 15.7 | 685.9 | 17.7 | 1319.8 | 19.4 | 1849.8 | 20.6 | ~2300-3800 |
| H4H12176P2:H4H12177P2:hC5 | 0.5:0.5:1 | 15.8 | 687.7 | 17.8 | 1333.8 | 19.3 | 1871.6 | 20.6 | ~2300-3600 |
| H4H12166P:H4H12170P:hC5 | 0.5:0.5:1 | 15.5 | 664.8 | 19.2 | 1304.3 | 21.9 | 1901.1 | 23.6 | ~2300-4100 |
| H4H12166P:H4H12171P:hC5 | 0.5:0.5:1 | 15.9 | 649.6 | 19.1 | 1288.2 | ND | ND | 20.6 | ~1700-2300 |

$R_t$: Retention Time;
$M_w$: weight average molar mass;
min: minutes;
kDa: kiloDaltons;
ND: not detected

TABLE 11

Summary Table of Approximate Molar Mass and Retention Time of hC5 Complexes with H412176P2 × H412177P2 (Anti-hC5 Bispecific mAb)

| Sample | Molar Ratio (μM:μM) | Peak 1 [mAb]$_1$:[hC5]$_1$ Complex | | Peak 2 [mAb]$_2$:[hC5]$_1$ Complex | | Peak 3 [mAb]$_1$:[hC5]$_2$ Complex | | Peak 4 [mAb]$_2$:[hC5]$_2$ Complex | |
|---|---|---|---|---|---|---|---|---|---|
| | | $R_t$, min | $M_w$, kDa | $R_t$, min | $M_w$, kDa | $R_t$, min | $M_w$, kDa | $R_t$, min | $M_w$, kDa |
| H412176P2 × H412177P2:hC5 | 3:1 | 11.2 | 359.3 | 11.9 | 506.5 | N/A | N/A | N/A | N/A |
| H412176P2 × H412177P2:hC5 | 1:1 | 11.2 | 347.2 | ND | ND | N/A | N/A | 12.3 | 681.3 |
| H412176P2 × H412177P2:hC5 | 1:3 | 11.1 | 350.9 | N/A | N/A | 12.2 | 559.5 | ND | ND |

$R_t$: Retention Time;
$M_w$: weight average molar mass;
min: minutes;
kDa: kiloDaltons;
ND: not detected

---

What is claimed is:

1. A method for treating a C5-associated disease or disorder in a subject in need thereof, the method comprising administering to the subject a first antibody or antigen-binding fragment thereof that specifically binds C5, and a second antibody or antigen-binding fragment thereof that specifically binds C5; wherein the first and second antibodies or antigen-binding fragments (a) bind to distinct, non-overlapping epitopes on C5; and (b) do not compete with one another for binding to C5;

wherein the first antibody or antigen-binding fragment thereof comprises a heavy chain variable region (HCVR) comprising three heavy chain complementarity determining regions (CDRs) (CDR-H1, CDR-H2, and CDR-H3) of a HCVR that comprises the amino acid sequence set forth in SEQ ID NO: 19, and a light chain variable region (LCVR) comprising three light chain CDRs (CDR-L1, CDR-L2, and CDR-L3) of a LCVR that comprises the amino acid sequence set forth in SEQ ID NO: 27.

2. The method of claim 1, wherein:
the first antibody or antigen-binding fragment blocks about 80% or less of alternative pathway-mediated hemolysis of rabbit red blood cells in vitro in the presence of normal human serum;
the second antibody or antigen-binding fragment blocks about 80% or less of alternative pathway-mediated hemolysis of rabbit red blood cells in vitro in the presence of normal human serum;

and, at a 1:1 molar ratio of the antibodies or fragments, the combination completely inhibits alternative pathway-mediated hemolysis of rabbit red blood cells in vitro in the presence of normal human serum.

3. The method of claim 1, wherein the C5-associated disease or disorder is selected from the group consisting of: Acute respiratory distress syndrome; adult respiratory distress syndrome; age-related macular degeneration; allergy; Alport's syndrome; Alzheimer's disease; asthma; atherosclerosis; atypical hemolytic uremic syndrome; an autoimmune disease; complement activation caused by balloon angioplasty; bronchoconstriction; bullous pemphigoid; a burn; C3 glomerulopathy; capillary leak syndrome; chemical injury; chronic obstructive pulmonary disease; Crohn's disease; diabetes; diabetic macular edema; diabetic nephropathy; diabetic retinopathy; dyspnea; emphysema; epilepsy; fibrogenic dust disease; frostbite; geographic atrophy; glomerulopathy; Goodpasture's Syndrome; Guillain-Barre Syndrome; complement activation caused by hemodialysis; a hemodialysis complication; hemolytic anemia; hemoptysis; hereditary angioedema; hyperacute allograft rejection; hypersensitivity pneumonitis; an immune complex disorder; immune complex-associated inflammation; inflammation of an autoimmune disease; an inflammatory disorder; inherited CD59 deficiency; injury due to inert dusts and/or minerals; interleukin-2 induced toxicity during IL-2 therapy; lupus nephritis; membranoproliferative glomerulonephritis; membranoproliferative nephritis; mesenteric artery reperfusion after aortic reconstruction; mesenteric artery reperfusion after infectious disease; mesenteric artery reperfusion after sepsis; multiple sclerosis; myasthenia gravis; myocardial infarction; neuromyelitis optica; obesity; ocular angiogenesis; organic dust disease; parasitic disease; Parkinson's disease; paroxysmal nocturnal hemoglobinuria; pneumonia; a post-ischemic reperfusion condition; post-pump syndrome in cardiopulmonary bypass or renal bypass; progressive kidney failure; proteinuric kidney disease; psoriasis; pulmonary embolism, pulmonary infarct; pulmonary fibrosis; pulmonary vasculitis; renal ischemia; renal ischemia-reperfusion injury; renal transplant; rheumatoid arthritis; schizophrenia; smoke injury; stroke; systemic lupus erythematosus; systemic lupus erythematosus nephritis; thermal injury; traumatic brain injury; uveitis; vasculitis; and xenograft rejection.

4. The method of claim 1, wherein the subject is administered one or more further therapeutic agents and/or one or more therapeutic procedures.

5. The method of claim 4 wherein the one or more further therapeutic agents is an antibody or antigen-binding fragment that specifically binds to C5.

6. The method claim of 4, wherein the one or more further therapeutic agents is selected from an antibody that binds to C5, an anti-coagulant, a thrombin inhibitor, an anti-inflammatory drug, an antihypertensive, an immunosuppressive agent, a fibrinolytic agent, a lipid-lowering agent, an inhibitor of hydroxymethylglutaryl CoA reductase, an anti-CD20 agent, an anti-TNFa agent, an anti-seizure agent, a C3 inhibitor and an anti-thrombotic agent;

and/or wherein the subject is administered a therapeutic procedure which is dialysis, a blood or plasma transfusion or exchange and/or a bone marrow/stem cell transplant (BMT/SCT).

7. The method claim 4, wherein the one or more further therapeutic agents is selected from the group consisting of: eculizumab, coversin, iron, antithymocyte globulin, a growth factor, warfarin, aspirin, heparin, phenindione, fondaparinux, idraparinux, argatroban, lepirudin, bivalirudin, or dabigatran, corticosteroids, a non-steroidal anti-inflammatory drug, vincristine, cyclosporine A, methotrexate, ancrod, ε-aminocaproic acid, antiplasmin-a1, prostacyclin, defibrotide, rituximab, magnesium sulfate, avacopan, ravulizumab and avacincaptad pegol.

8. The method of claim 1, wherein the first antibody or antigen-binding fragment thereof and the second antibody or antigen-binding fragment thereof are administered to the subject subcutaneously, intravenously, intradermally, intraperitoneally, orally, intramuscularly or intracranially.

9. The method of claim 1, wherein the subject is human.

10. The method of claim 1, wherein the C5-associated disease or disorder is paroxysmal nocturnal hemoglobinuria.

11. The method of claim 1, wherein the C5-associated disease or disorder is myasthenia gravis.

12. The method of claim 1, wherein the C5-associated disease or disorder is atypical hemolytic uremic syndrome.

13. The method of claim 1, wherein the C5-associated disease or disorder is neuromyelitis optica.

14. The method of claim 1, wherein the first antibody or antigen-binding fragment thereof that specifically binds C5 comprises CDR-H1 comprising the amino acid sequence set forth in SEQ ID NO: 21; CDR-H2 comprising the amino acid sequence set forth in SEQ ID NO: 23; CDR-H3 comprising the amino acid sequence set forth in SEQ ID NO: 25; CDR-L1 comprising the amino acid sequence set forth in SEQ ID NO: 29; CDR-L2 comprising the amino acid sequence set forth in SEQ ID NO: 31; and CDR-L3 comprising the amino acid sequence set forth in SEQ ID NO: 33.

15. The method of claim 1, wherein the first antibody or antigen-binding fragment thereof that specifically binds C5 comprises a HCVR comprising the amino acid sequence set forth in SEQ ID NO: 19; and a LCVR comprising the amino acid sequence set forth in SEQ ID NO: 27.

* * * * *

SEQUENCE LISTING

<160> NUMBER OF SEQ ID NOS: 109

<210> SEQ ID NO 1
<211> LENGTH: 1676
<212> TYPE: PRT
<213> ORGANISM: Homo sapiens

<400> SEQUENCE: 1

```
Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
            20                  25                  30

Val Gly Ala Ser Glu Asn Ile Val Ile Gln Val Tyr Gly Tyr Thr Glu
        35                  40                  45

Ala Phe Asp Ala Thr Ile Ser Ile Lys Ser Tyr Pro Asp Lys Lys Phe
    50                  55                  60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
                85                  90                  95

Asn Pro Val Ser Tyr Val Tyr Leu Glu Val Val Ser Lys His Phe Ser
            100                 105                 110

Lys Ser Lys Arg Met Pro Ile Thr Tyr Asp Asn Gly Phe Leu Phe Ile
        115                 120                 125

His Thr Asp Lys Pro Val Tyr Thr Pro Asp Gln Ser Val Lys Val Arg
    130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Lys Ala Lys Tyr Lys Glu Asp
        195                 200                 205

Phe Ser Thr Thr Gly Thr Ala Tyr Phe Glu Val Lys Glu Tyr Val Leu
    210                 215                 220

Pro His Phe Ser Val Ser Ile Glu Pro Glu Tyr Asn Phe Ile Gly Tyr
225                 230                 235                 240
```

```
Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
            260                 265                 270

Glu Asp Leu Lys Asp Asp Gln Lys Glu Met Met Gln Thr Ala Met Gln
                275                 280                 285

Asn Thr Met Leu Ile Asn Gly Ile Ala Gln Val Thr Phe Asp Ser Glu
            290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

Ser Glu Glu Ala Glu Ile Pro Gly Ile Lys Tyr Val Leu Ser Pro Tyr
                340                 345                 350

Lys Leu Asn Leu Val Ala Thr Pro Leu Phe Leu Lys Pro Gly Ile Pro
                355                 360                 365

Tyr Pro Ile Lys Val Gln Val Lys Asp Ser Leu Asp Gln Leu Val Gly
            370                 375                 380

Gly Val Pro Val Thr Leu Asn Ala Gln Thr Ile Asp Val Asn Gln Glu
385                 390                 395                 400

Thr Ser Asp Leu Asp Pro Ser Lys Ser Val Thr Arg Val Asp Asp Gly
                405                 410                 415

Val Ala Ser Phe Val Leu Asn Leu Pro Ser Gly Val Thr Val Leu Glu
                420                 425                 430

Phe Asn Val Lys Thr Asp Ala Pro Asp Leu Pro Glu Glu Asn Gln Ala
                435                 440                 445

Arg Glu Gly Tyr Arg Ala Ile Ala Tyr Ser Ser Leu Ser Gln Ser Tyr
450                 455                 460

Leu Tyr Ile Asp Trp Thr Asp Asn His Lys Ala Leu Leu Val Gly Glu
465                 470                 475                 480

His Leu Asn Ile Ile Val Thr Pro Lys Ser Pro Tyr Ile Asp Lys Ile
                485                 490                 495

Thr His Tyr Asn Tyr Leu Ile Leu Ser Lys Gly Lys Ile Ile His Phe
                500                 505                 510

Gly Thr Arg Glu Lys Phe Ser Asp Ala Ser Tyr Gln Ser Ile Asn Ile
                515                 520                 525

Pro Val Thr Gln Asn Met Val Pro Ser Ser Arg Leu Leu Val Tyr Tyr
                530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
                565                 570                 575

Pro Asp Ala Asp Ala Tyr Ser Pro Gly Gln Thr Val Ser Leu Asn Met
                580                 585                 590

Ala Thr Gly Met Asp Ser Trp Val Ala Leu Ala Ala Val Asp Ser Ala
                595                 600                 605

Val Tyr Gly Val Gln Arg Gly Ala Lys Lys Pro Leu Glu Arg Val Phe
                610                 615                 620

Gln Phe Leu Glu Lys Ser Asp Leu Gly Cys Gly Ala Gly Gly Gly Leu
625                 630                 635                 640

Asn Asn Ala Asn Val Phe His Leu Ala Gly Leu Thr Phe Leu Thr Asn
                645                 650                 655

Ala Asn Ala Asp Asp Ser Gln Glu Asn Asp Glu Pro Cys Lys Glu Ile
```

-continued

```
                660             665             670
Leu Arg Pro Arg Arg Thr Leu Gln Lys Lys Ile Glu Glu Ile Ala Ala
            675             680             685
Lys Tyr Lys His Ser Val Val Lys Cys Cys Tyr Asp Gly Ala Cys
690             695             700
Val Asn Asn Asp Glu Thr Cys Glu Gln Arg Ala Ala Arg Ile Ser Leu
705             710             715             720
Gly Pro Arg Cys Ile Lys Ala Phe Thr Glu Cys Cys Val Val Ala Ser
                725             730             735
Gln Leu Arg Ala Asn Ile Ser His Lys Asp Met Gln Leu Gly Arg Leu
            740             745             750
His Met Lys Thr Leu Leu Pro Val Ser Lys Pro Glu Ile Arg Ser Tyr
            755             760             765
Phe Pro Glu Ser Trp Leu Trp Glu Val His Leu Val Pro Arg Arg Lys
            770             775             780
Gln Leu Gln Phe Ala Leu Pro Asp Ser Leu Thr Thr Trp Glu Ile Gln
785             790             795             800
Gly Val Gly Ile Ser Asn Thr Gly Ile Cys Val Ala Asp Thr Val Lys
                805             810             815
Ala Lys Val Phe Lys Asp Val Phe Leu Glu Met Asn Ile Pro Tyr Ser
                820             825             830
Val Val Arg Gly Glu Gln Ile Gln Leu Lys Gly Thr Val Tyr Asn Tyr
            835             840             845
Arg Thr Ser Gly Met Gln Phe Cys Val Lys Met Ser Ala Val Glu Gly
            850             855             860
Ile Cys Thr Ser Glu Ser Pro Val Ile Asp His Gln Gly Thr Lys Ser
865             870             875             880
Ser Lys Cys Val Arg Gln Lys Val Glu Gly Ser Ser His Leu Val
                885             890             895
Thr Phe Thr Val Leu Pro Leu Glu Ile Gly Leu His Asn Ile Asn Phe
            900             905             910
Ser Leu Glu Thr Trp Phe Gly Lys Glu Ile Leu Val Lys Thr Leu Arg
            915             920             925
Val Val Pro Glu Gly Val Lys Arg Glu Ser Tyr Ser Gly Val Thr Leu
            930             935             940
Asp Pro Arg Gly Ile Tyr Gly Thr Ile Ser Arg Arg Lys Glu Phe Pro
945             950             955             960
Tyr Arg Ile Pro Leu Asp Leu Val Pro Lys Thr Glu Ile Lys Arg Ile
                965             970             975
Leu Ser Val Lys Gly Leu Leu Val Gly Glu Ile Leu Ser Ala Val Leu
            980             985             990
Ser Gln Glu Gly Ile Asn Ile Leu Thr His Leu Pro Lys Gly Ser Ala
            995             1000            1005
Glu Ala Glu Leu Met Ser Val Val Pro Val Phe Tyr Val Phe His
            1010            1015            1020
Tyr Leu Glu Thr Gly Asn His Trp Asn Ile Phe His Ser Asp Pro
            1025            1030            1035
Leu Ile Glu Lys Gln Lys Leu Lys Lys Lys Leu Lys Glu Gly Met
            1040            1045            1050
Leu Ser Ile Met Ser Tyr Arg Asn Ala Asp Tyr Ser Tyr Ser Val
            1055            1060            1065
Trp Lys Gly Gly Ser Ala Ser Thr Trp Leu Thr Ala Phe Ala Leu
            1070            1075            1080
```

```
Arg Val Leu Gly Gln Val Asn Lys Tyr Val Glu Gln Asn Gln Asn
1085                1090                1095

Ser Ile Cys Asn Ser Leu Leu Trp Leu Val Glu Asn Tyr Gln Leu
1100                1105                1110

Asp Asn Gly Ser Phe Lys Glu Asn Ser Gln Tyr Gln Pro Ile Lys
1115                1120                1125

Leu Gln Gly Thr Leu Pro Val Glu Ala Arg Glu Asn Ser Leu Tyr
1130                1135                1140

Leu Thr Ala Phe Thr Val Ile Gly Ile Arg Lys Ala Phe Asp Ile
1145                1150                1155

Cys Pro Leu Val Lys Ile Asp Thr Ala Leu Ile Lys Ala Asp Asn
1160                1165                1170

Phe Leu Leu Glu Asn Thr Leu Pro Ala Gln Ser Thr Phe Thr Leu
1175                1180                1185

Ala Ile Ser Ala Tyr Ala Leu Ser Leu Gly Asp Lys Thr His Pro
1190                1195                1200

Gln Phe Arg Ser Ile Val Ser Ala Leu Lys Arg Glu Ala Leu Val
1205                1210                1215

Lys Gly Asn Pro Pro Ile Tyr Arg Phe Trp Lys Asp Asn Leu Gln
1220                1225                1230

His Lys Asp Ser Ser Val Pro Asn Thr Gly Thr Ala Arg Met Val
1235                1240                1245

Glu Thr Thr Ala Tyr Ala Leu Leu Thr Ser Leu Asn Leu Lys Asp
1250                1255                1260

Ile Asn Tyr Val Asn Pro Val Ile Lys Trp Leu Ser Glu Glu Gln
1265                1270                1275

Arg Tyr Gly Gly Gly Phe Tyr Ser Thr Gln Asp Thr Ile Asn Ala
1280                1285                1290

Ile Glu Gly Leu Thr Glu Tyr Ser Leu Leu Val Lys Gln Leu Arg
1295                1300                1305

Leu Ser Met Asp Ile Asp Val Ser Tyr Lys His Lys Gly Ala Leu
1310                1315                1320

His Asn Tyr Lys Met Thr Asp Lys Asn Phe Leu Gly Arg Pro Val
1325                1330                1335

Glu Val Leu Leu Asn Asp Asp Leu Ile Val Ser Thr Gly Phe Gly
1340                1345                1350

Ser Gly Leu Ala Thr Val His Val Thr Thr Val Val His Lys Thr
1355                1360                1365

Ser Thr Ser Glu Glu Val Cys Ser Phe Tyr Leu Lys Ile Asp Thr
1370                1375                1380

Gln Asp Ile Glu Ala Ser His Tyr Arg Gly Tyr Gly Asn Ser Asp
1385                1390                1395

Tyr Lys Arg Ile Val Ala Cys Ala Ser Tyr Lys Pro Ser Arg Glu
1400                1405                1410

Glu Ser Ser Ser Gly Ser Ser His Ala Val Met Asp Ile Ser Leu
1415                1420                1425

Pro Thr Gly Ile Ser Ala Asn Glu Glu Asp Leu Lys Ala Leu Val
1430                1435                1440

Glu Gly Val Asp Gln Leu Phe Thr Asp Tyr Gln Ile Lys Asp Gly
1445                1450                1455

His Val Ile Leu Gln Leu Asn Ser Ile Pro Ser Ser Asp Phe Leu
1460                1465                1470
```

```
Cys Val Arg Phe Arg Ile Phe Glu Leu Phe Glu Val Gly Phe Leu
    1475                1480                1485

Ser Pro Ala Thr Phe Thr Val Tyr Glu Tyr His Arg Pro Asp Lys
    1490                1495                1500

Gln Cys Thr Met Phe Tyr Ser Thr Ser Asn Ile Lys Ile Gln Lys
    1505                1510                1515

Val Cys Glu Gly Ala Ala Cys Lys Cys Val Glu Ala Asp Cys Gly
    1520                1525                1530

Gln Met Gln Glu Glu Leu Asp Leu Thr Ile Ser Ala Glu Thr Arg
    1535                1540                1545

Lys Gln Thr Ala Cys Lys Pro Glu Ile Ala Tyr Ala Tyr Lys Val
    1550                1555                1560

Ser Ile Thr Ser Ile Thr Val Glu Asn Val Phe Val Lys Tyr Lys
    1565                1570                1575

Ala Thr Leu Leu Asp Ile Tyr Lys Thr Gly Glu Ala Val Ala Glu
    1580                1585                1590

Lys Asp Ser Glu Ile Thr Phe Ile Lys Lys Val Thr Cys Thr Asn
    1595                1600                1605

Ala Glu Leu Val Lys Gly Arg Gln Tyr Leu Ile Met Gly Lys Glu
    1610                1615                1620

Ala Leu Gln Ile Lys Tyr Asn Phe Ser Phe Arg Tyr Ile Tyr Pro
    1625                1630                1635

Leu Asp Ser Leu Thr Trp Ile Glu Tyr Trp Pro Arg Asp Thr Thr
    1640                1645                1650

Cys Ser Ser Cys Gln Ala Phe Leu Ala Asn Leu Asp Glu Phe Ala
    1655                1660                1665

Glu Asp Ile Phe Leu Asn Gly Cys
    1670                1675

<210> SEQ ID NO 2
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 2 gag gtg cag ctg gtg gag tct ggg gga gac ttg gtc cag cct gga ggg    48
Glu Val Gln Leu Val Glu Ser Gly Gly Asp Leu Val Gln Pro Gly Gly
1               5                   10                  15 tcc ctg aga ctc tcc tgt gca gcc tct gga ttc acc ttc agt gac cac    96
Ser Leu Arg Leu Ser Cys Ala Ala Ser Gly Phe Thr Phe Ser Asp His
            20                  25                  30 tat atg gac tgg gtc cgc cag gct cca ggg aag ggg ctg gac tgg att   144
Tyr Met Asp Trp Val Arg Gln Ala Pro Gly Lys Gly Leu Asp Trp Ile
        35                  40                  45 ggc cgt att aga aac aaa gct aac gct tat aac aca gaa tac gcc gcg   192
Gly Arg Ile Arg Asn Lys Ala Asn Ala Tyr Asn Thr Glu Tyr Ala Ala
    50                  55                  60 tct gtg aga ggc aga ttc acc atc tca aga gat gat tca cag aat tta   240
Ser Val Arg Gly Arg Phe Thr Ile Ser Arg Asp Asp Ser Gln Asn Leu
65                  70                  75                  80 ctg tat ctg caa atg aac agc ctg aaa acc gat gac acg gcc gta tat   288
Leu Tyr Leu Gln Met Asn Ser Leu Lys Thr Asp Asp Thr Ala Val Tyr
                85                  90                  95 tat tgt gtt aga gtc tgg aac tac gcc tac ttc gct atg gac gtc tgg   336
Tyr Cys Val Arg Val Trp Asn Tyr Ala Tyr Phe Ala Met Asp Val Trp
```

```
                100             105             110
ggc caa ggg acc acg gtc acc gtc tcc tca                         366
Gly Gln Gly Thr Thr Val Thr Val Ser Ser
        115             120

<210> SEQ ID NO 3
<211> LENGTH: 122
<212> TYPE: PRT
<213> ORGANISM: Homo sapiens

<400> SEQUENCE: 3

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Asp Trp Ile
        35                  40                  45

Gly Arg Ile Arg Asn Lys Ala Asn Ala Tyr Asn Thr Glu Tyr Ala Ala
    50                  55                  60

Ser Val Arg Gly Arg Phe Thr Ile Ser Arg Asp Asp Ser Gln Asn Leu
65                  70                  75                  80

Leu Tyr Leu Gln Met Asn Ser Leu Lys Thr Asp Asp Thr Ala Val Tyr
                85                  90                  95

Tyr Cys Val Arg Val Trp Asn Tyr Ala Tyr Phe Ala Met Asp Val Trp
            100                 105                 110

Gly Gln Gly Thr Thr Val Thr Val Ser Ser
        115             120

<210> SEQ ID NO 4
<211> LENGTH: 24
<212> TYPE: DNA
<213> ORGANISM: Homo sapiens

<400> SEQUENCE: 4
ggattcacct tcagtgacca ctat                                      24

<210> SEQ ID NO 5
<211> LENGTH: 8
<212> TYPE: PRT
<213> ORGANISM: Homo sapiens

<400> SEQUENCE: 5

Gly Phe Thr Phe Ser Asp His Tyr
1               5

<210> SEQ ID NO 6
<211> LENGTH: 30
<212> TYPE: DNA
<213> ORGANISM: Homo sapiens

<400> SEQUENCE: 6
attagaaaca aagctaacgc ttataacaca                                30

<210> SEQ ID NO 7
<211> LENGTH: 10
<212> TYPE: PRT
<213> ORGANISM: Homo sapiens

<400> SEQUENCE: 7

Ile Arg Asn Lys Ala Asn Ala Tyr Asn Thr
1               5                   10
```

<210> SEQ ID NO 8
<211> LENGTH: 39
<212> TYPE: DNA
<213> ORGANISM: Homo sapiens

<400> SEQUENCE: 8
gttagagtct ggaactacgc ctacttcgct atggacgtc                                39

<210> SEQ ID NO 9
<211> LENGTH: 13
<212> TYPE: PRT
<213> ORGANISM: Homo sapiens

<400> SEQUENCE: 9

Val Arg Val Trp Asn Tyr Ala Tyr Phe Ala Met Asp Val
1               5                   10

<210> SEQ ID NO 10
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 10 gac atc cag atg acc cag tct cca tcc tcc cta tct gca tct gtg gga      48
Asp Ile Gln Met Thr Gln Ser Pro Ser Ser Leu Ser Ala Ser Val Gly
1               5                   10                  15 gac aga gtc acc atc act tgc cgg tca agt cag aac att gga atc ttt      96
Asp Arg Val Thr Ile Thr Cys Arg Ser Ser Gln Asn Ile Gly Ile Phe
            20                  25                  30 tta aac tgg tat caa caa aaa cca ggg gaa gcc cct aac ctc ctg atc     144
Leu Asn Trp Tyr Gln Gln Lys Pro Gly Glu Ala Pro Asn Leu Leu Ile
        35                  40                  45 tcc gct gca tcc agt tta cac agt ggg gtc cct tca agg ttc agt ggc     192
Ser Ala Ala Ser Ser Leu His Ser Gly Val Pro Ser Arg Phe Ser Gly
    50                  55                  60 agt ggg tct ggg aca gat ttc act ctc acc atc ggc agt ctg cag cct     240
Ser Gly Ser Gly Thr Asp Phe Thr Leu Thr Ile Gly Ser Leu Gln Pro
65                  70                  75                  80 gaa gat ttt gcg act tac tac tgt caa cag acg tac aat acc ata ttc     288
Glu Asp Phe Ala Thr Tyr Tyr Cys Gln Gln Thr Tyr Asn Thr Ile Phe
                85                  90                  95 act ttc ggc cct ggg acc aaa gtg gat atc aaa                         321
Thr Phe Gly Pro Gly Thr Lys Val Asp Ile Lys
            100                 105

<210> SEQ ID NO 11
<211> LENGTH: 107
<212> TYPE: PRT
<213> ORGANISM: Homo sapiens

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asn Ile Gly Ile Phe
            20                  25                  30

Leu Asn Trp Tyr Gln Gln Lys Pro Gly Glu Ala Pro Asn Leu Leu Ile
        35                  40                  45

Ser Ala Ala Ser Ser Leu His Ser Gly Val Pro Ser Arg Phe Ser Gly

```
                    50                  55                  60
Ser Gly Ser Gly Thr Asp Phe Thr Leu Thr Ile Gly Ser Leu Gln Pro
65                  70                  75                  80

Glu Asp Phe Ala Thr Tyr Tyr Cys Gln Gln Thr Tyr Asn Thr Ile Phe
                85                  90                  95

Thr Phe Gly Pro Gly Thr Lys Val Asp Ile Lys
            100                 105
```

<210> SEQ ID NO 12
<211> LENGTH: 18
<212> TYPE: DNA
<213> ORGANISM: Homo sapiens

<400> SEQUENCE: 12
cagaacattg gaatctttt                                              18

<210> SEQ ID NO 13
<211> LENGTH: 6
<212> TYPE: PRT
<213> ORGANISM: Homo sapiens

<400> SEQUENCE: 13

```
Gln Asn Ile Gly Ile Phe
1               5
```

<210> SEQ ID NO 14
<211> LENGTH: 9
<212> TYPE: DNA
<213> ORGANISM: Homo sapiens

<400> SEQUENCE: 14 gctgcatcc                                                          9

<210> SEQ ID NO 15
<211> LENGTH: 3
<212> TYPE: PRT
<213> ORGANISM: Homo sapiens

<400> SEQUENCE: 15

```
Ala Ala Ser
1
```

<210> SEQ ID NO 16
<211> LENGTH: 27
<212> TYPE: DNA
<213> ORGANISM: Homo sapiens

<400> SEQUENCE: 16
caacagacgt acaataccat attcact                                     27

<210> SEQ ID NO 17
<211> LENGTH: 9
<212> TYPE: PRT
<213> ORGANISM: Homo sapiens

<400> SEQUENCE: 17

```
Gln Gln Thr Tyr Asn Thr Ile Phe Thr
1               5
```

<210> SEQ ID NO 18
<211> LENGTH: 360
<212> TYPE: DNA
<213> ORGANISM: Homo sapiens

```
<220> FEATURE:
<221> NAME/KEY: CDS
<222> LOCATION: (1)..(360)

<400> SEQUENCE: 18 cag gtg cag ctg cag gag tcg ggc cca gga ctg gtg aag cct tcg gag       48
Gln Val Gln Leu Gln Glu Ser Gly Pro Gly Leu Val Lys Pro Ser Glu
1               5                   10                  15 acc ctg tcc ctc acc tgc act gtc tct ggt gac tcc gtc agt agt tcc       96
Thr Leu Ser Leu Thr Cys Thr Val Ser Gly Asp Ser Val Ser Ser Ser
            20                  25                  30 tac tgg acc tgg atc cgg cag ccc cca ggg aag gga ctg gag tgg att      144
Tyr Trp Thr Trp Ile Arg Gln Pro Pro Gly Lys Gly Leu Glu Trp Ile
        35                  40                  45 ggc tat atc tat tac agt ggg agt tcc aac tac aac ccc tcc ctc aag      192
Gly Tyr Ile Tyr Tyr Ser Gly Ser Ser Asn Tyr Asn Pro Ser Leu Lys
    50                  55                  60 agt cga gcc acc att tca gta gac acg tcc aag aac cag ttc tcc ctg      240
Ser Arg Ala Thr Ile Ser Val Asp Thr Ser Lys Asn Gln Phe Ser Leu
65                  70                  75                  80 aag ctg agt tct gtg acc gct gcg gac acg gcc gta tat tac tgt gcg      288
Lys Leu Ser Ser Val Thr Ala Ala Asp Thr Ala Val Tyr Tyr Cys Ala
                85                  90                  95 aga gaa ggg aac gtg gat aca act atg ata ttt gac tac tgg ggc cag      336
Arg Glu Gly Asn Val Asp Thr Thr Met Ile Phe Asp Tyr Trp Gly Gln
            100                 105                 110 gga acc ctg gtc acc gtc tcc tca                                      360
Gly Thr Leu Val Thr Val Ser Ser
        115                 120

<210> SEQ ID NO 19
<211> LENGTH: 120
<212> TYPE: PRT
<213> ORGANISM: Homo sapiens

<400> SEQUENCE: 19

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Ser Ser Ser
            20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Ser Ser Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asn Val Asp Thr Thr Met Ile Phe Asp Tyr Trp Gly Gln
            100                 105                 110

Gly Thr Leu Val Thr Val Ser Ser
        115                 120

<210> SEQ ID NO 20
<211> LENGTH: 24
<212> TYPE: DNA
<213> ORGANISM: Homo sapiens

<400> SEQUENCE: 20
ggtgactccg tcagtagttc ctac                                            24
```

-continued

```
<210> SEQ ID NO 21
<211> LENGTH: 8
<212> TYPE: PRT
<213> ORGANISM: Homo sapiens

<400> SEQUENCE: 21

Gly Asp Ser Val Ser Ser Ser Tyr
1               5

<210> SEQ ID NO 22
<211> LENGTH: 21
<212> TYPE: DNA
<213> ORGANISM: Homo sapiens

<400> SEQUENCE: 22
atctattaca gtgggagttc c                                             21

<210> SEQ ID NO 23
<211> LENGTH: 7
<212> TYPE: PRT
<213> ORGANISM: Homo sapiens

<400> SEQUENCE: 23

Ile Tyr Tyr Ser Gly Ser Ser
1               5

<210> SEQ ID NO 24
<211> LENGTH: 42
<212> TYPE: DNA
<213> ORGANISM: Homo sapiens

<400> SEQUENCE: 24
gcgagagaag ggaacgtgga tacaactatg atatttgact ac                      42

<210> SEQ ID NO 25
<211> LENGTH: 14
<212> TYPE: PRT
<213> ORGANISM: Homo sapiens

<400> SEQUENCE: 25

Ala Arg Glu Gly Asn Val Asp Thr Thr Met Ile Phe Asp Tyr
1               5                   10

<210> SEQ ID NO 26
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 26 gcc atc cag atg acc cag tct cca tcc tcc ctg tct gca tct gta gga    48
Ala Ile Gln Met Thr Gln Ser Pro Ser Ser Leu Ser Ala Ser Val Gly
1               5                   10                  15 gac aga gtc acc atc act tgc cgg gca agt cag ggc att aga aat gat    96
Asp Arg Val Thr Ile Thr Cys Arg Ala Ser Gln Gly Ile Arg Asn Asp
            20                  25                  30 tta ggc tgg tat caa cag aaa cca ggg aaa gcc cct aaa ctc ctg atc   144
Leu Gly Trp Tyr Gln Gln Lys Pro Gly Lys Ala Pro Lys Leu Leu Ile
        35                  40                  45 tat gct gca tcc agt tta caa agt ggg gtc cca tcg agg ttc gcc ggc   192
Tyr Ala Ala Ser Ser Leu Gln Ser Gly Val Pro Ser Arg Phe Ala Gly
```

```
                50                  55                  60
cgt gga tct ggc aca gat ttc act ctc acc atc agc agc ctg cag cct      240
Arg Gly Ser Gly Thr Asp Phe Thr Leu Thr Ile Ser Ser Leu Gln Pro
 65                  70                  75                  80 gaa gat ttt gca act tat tac tgt cta caa gat ttc aat tac ccg tgg      288
Glu Asp Phe Ala Thr Tyr Tyr Cys Leu Gln Asp Phe Asn Tyr Pro Trp
                 85                  90                  95 acg ttc ggc caa ggg acc aag gtg gaa atc aaa                          321
Thr Phe Gly Gln Gly Thr Lys Val Glu Ile Lys
                100                 105
```

<210> SEQ ID NO 27
<211> LENGTH: 107
<212> TYPE: PRT
<213> ORGANISM: Homo sapiens

<400> SEQUENCE: 27

```
Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ala Gly
 50                  55                  60

Arg Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Phe Asn Tyr Pro Trp
                 85                  90                  95

Thr Phe Gly Gln Gly Thr Lys Val Glu Ile Lys
                100                 105
```

<210> SEQ ID NO 28
<211> LENGTH: 18
<212> TYPE: DNA
<213> ORGANISM: Homo sapiens

<400> SEQUENCE: 28
cagggcatta gaaatgat                                                   18

<210> SEQ ID NO 29
<211> LENGTH: 6
<212> TYPE: PRT
<213> ORGANISM: Homo sapiens

<400> SEQUENCE: 29

```
Gln Gly Ile Arg Asn Asp
 1               5
```

<210> SEQ ID NO 30
<211> LENGTH: 9
<212> TYPE: DNA
<213> ORGANISM: Homo sapiens

<400> SEQUENCE: 30 gctgcatcc                                                              9

<210> SEQ ID NO 31
<211> LENGTH: 3
<212> TYPE: PRT
<213> ORGANISM: Homo sapiens

```
<400> SEQUENCE: 31

Ala Ala Ser
1

<210> SEQ ID NO 32
<211> LENGTH: 27
<212> TYPE: DNA
<213> ORGANISM: Homo sapiens

<400> SEQUENCE: 32
ctacaagatt tcaattaccc gtggacg                                          27

<210> SEQ ID NO 33
<211> LENGTH: 9
<212> TYPE: PRT
<213> ORGANISM: Homo sapiens

<400> SEQUENCE: 33

Leu Gln Asp Phe Asn Tyr Pro Trp Thr
1               5

<210> SEQ ID NO 34
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 34 cag gtg cag ctg gtg gag tct ggg gga ggc gtg gtc cag cct ggg agg      48
Gln Val Gln Leu Val Glu Ser Gly Gly Gly Val Val Gln Pro Gly Arg
1               5                   10                  15 tcc ctg aga ctc tcc tgt gca gcg tct gga ttc acc ttc agt ggt tat      96
Ser Leu Arg Leu Ser Cys Ala Ala Ser Gly Phe Thr Phe Ser Gly Tyr
            20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
        35                  40                  45 gca ctt ata tgg ctt gat gga agt aat gac tac tat gca gac tcc gtg     192
Ala Leu Ile Trp Leu Asp Gly Ser Asn Asp Tyr Tyr Ala Asp Ser Val
    50                  55                  60 aag ggc cga ttc acc atc tcc aga gac aat tcc aag aac acg tta tat     240
Lys Gly Arg Phe Thr Ile Ser Arg Asp Asn Ser Lys Asn Thr Leu Tyr
65                  70                  75                  80 ctg caa atg aac aga ctg aga gcc gag gac acg gct gtg tat tac tgt     288
Leu Gln Met Asn Arg Leu Arg Ala Glu Asp Thr Ala Val Tyr Tyr Cys
                85                  90                  95 gcg aga gat ggc ccg gtt gct gct ata ccc gac tac tgg ggc cag gga     336
Ala Arg Asp Gly Pro Val Ala Ala Ile Pro Asp Tyr Trp Gly Gln Gly
            100                 105                 110 acc ctg gtc acc gtc tcc tca                                         357
Thr Leu Val Thr Val Ser Ser
        115

<210> SEQ ID NO 35
<211> LENGTH: 119
<212> TYPE: PRT
<213> ORGANISM: Homo sapiens

<400> SEQUENCE: 35

Gln Val Gln Leu Val Glu Ser Gly Gly Gly Val Val Gln Pro Gly Arg
```

```
                1               5                  10                 15
Ser Leu Arg Leu Ser Cys Ala Ala Ser Gly Phe Thr Phe Ser Gly Tyr
            20                  25                 30

Gly Met His Trp Val Arg Gln Ala Pro Gly Lys Gly Leu Glu Trp Val
            35                  40                 45

Ala Leu Ile Trp Leu Asp Gly Ser Asn Asp Tyr Tyr Ala Asp Ser Val
            50                  55                 60

Lys Gly Arg Phe Thr Ile Ser Arg Asp Asn Ser Lys Asn Thr Leu Tyr
65                  70                  75                 80

Leu Gln Met Asn Arg Leu Arg Ala Glu Asp Thr Ala Val Tyr Tyr Cys
                85                  90                 95

Ala Arg Asp Gly Pro Val Ala Ala Ile Pro Asp Tyr Trp Gly Gln Gly
                100                 105                110

Thr Leu Val Thr Val Ser Ser
            115
```

<210> SEQ ID NO 36
<211> LENGTH: 24
<212> TYPE: DNA
<213> ORGANISM: Homo sapiens

<400> SEQUENCE: 36
ggattcacct tcagtggtta tggc                                          24

<210> SEQ ID NO 37
<211> LENGTH: 8
<212> TYPE: PRT
<213> ORGANISM: Homo sapiens

<400> SEQUENCE: 37

```
Gly Phe Thr Phe Ser Gly Tyr Gly
1               5
```

<210> SEQ ID NO 38
<211> LENGTH: 24
<212> TYPE: DNA
<213> ORGANISM: Homo sapiens

<400> SEQUENCE: 38
atatggcttg atggaagtaa tgac                                          24

<210> SEQ ID NO 39
<211> LENGTH: 8
<212> TYPE: PRT
<213> ORGANISM: Homo sapiens

<400> SEQUENCE: 39

```
Ile Trp Leu Asp Gly Ser Asn Asp
1               5
```

<210> SEQ ID NO 40
<211> LENGTH: 36
<212> TYPE: DNA
<213> ORGANISM: Homo sapiens

<400> SEQUENCE: 40
gcgagagatg gcccggttgc tgctataccc gactac                             36

<210> SEQ ID NO 41
<211> LENGTH: 12
<212> TYPE: PRT

-continued

<213> ORGANISM: Homo sapiens

<400> SEQUENCE: 41

Ala Arg Asp Gly Pro Val Ala Ala Ile Pro Asp Tyr
1               5                   10

<210> SEQ ID NO 42
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 42

```
gac atc cag atg acc cag tct cct tcc acc ctg tct gca tct gta gga      48
Asp Ile Gln Met Thr Gln Ser Pro Ser Thr Leu Ser Ala Ser Val Gly
1               5                   10                  15 gac aga gtc acc atc act tgc cgg gcc agt cag agt att agt agg tgg      96
Asp Arg Val Thr Ile Thr Cys Arg Ala Ser Gln Ser Ile Ser Arg Trp
                20                  25                  30 ttg gcc tgg tat cag ctg aaa cca ggg aaa gcc cct aag ctc ctg atc     144
Leu Ala Trp Tyr Gln Leu Lys Pro Gly Lys Ala Pro Lys Leu Leu Ile
        35                  40                  45 tat aag gcg tct agt tta gaa agt ggg gtc cca tca agg ttc agc ggc     192
Tyr Lys Ala Ser Ser Leu Glu Ser Gly Val Pro Ser Arg Phe Ser Gly
50                  55                  60 agt gga tct ggg aca gac ttc act ctc acc atc agc agc ctg caa cct     240
Ser Gly Ser Gly Thr Asp Phe Thr Leu Thr Ile Ser Ser Leu Gln Pro
65                  70                  75                  80 gat gat ttt gca act tat tac tgc caa cag tat aat act tat tcg tac     288
Asp Asp Phe Ala Thr Tyr Tyr Cys Gln Gln Tyr Asn Thr Tyr Ser Tyr
                85                  90                  95 act ttt ggc cag ggg acc aag ctg gag atc aaa                         321
Thr Phe Gly Gln Gly Thr Lys Leu Glu Ile Lys
            100                 105
```

<210> SEQ ID NO 43
<211> LENGTH: 107
<212> TYPE: PRT
<213> ORGANISM: Homo sapiens

<400> SEQUENCE: 43

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Arg Trp
                20                  25                  30

Leu Ala Trp Tyr Gln Leu Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Asn Thr Tyr Ser Tyr
                85                  90                  95

Thr Phe Gly Gln Gly Thr Lys Leu Glu Ile Lys
            100                 105

<210> SEQ ID NO 44
<211> LENGTH: 18
<212> TYPE: DNA

<213> ORGANISM: Homo sapiens

<400> SEQUENCE: 44
cagagtatta gtaggtgg                                                   18

<210> SEQ ID NO 45
<211> LENGTH: 6
<212> TYPE: PRT
<213> ORGANISM: Homo sapiens

<400> SEQUENCE: 45

Gln Ser Ile Ser Arg Trp
1               5

<210> SEQ ID NO 46
<211> LENGTH: 9
<212> TYPE: DNA
<213> ORGANISM: Homo sapiens

<400> SEQUENCE: 46 aaggcgtct                                                              9

<210> SEQ ID NO 47
<211> LENGTH: 3
<212> TYPE: PRT
<213> ORGANISM: Homo sapiens

<400> SEQUENCE: 47

Lys Ala Ser
1

<210> SEQ ID NO 48
<211> LENGTH: 27
<212> TYPE: DNA
<213> ORGANISM: Homo sapiens

<400> SEQUENCE: 48
caacagtata atacttattc gtacact                                         27

<210> SEQ ID NO 49
<211> LENGTH: 9
<212> TYPE: PRT
<213> ORGANISM: Homo sapiens

<400> SEQUENCE: 49

Gln Gln Tyr Asn Thr Tyr Ser Tyr Thr
1               5

<210> SEQ ID NO 50
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 50 gag gtg cag ctg gtg gag tct ggg gga ggt gtg gta cgg cct ggg ggg      48
Glu Val Gln Leu Val Glu Ser Gly Gly Gly Val Val Arg Pro Gly Gly
1               5                   10                  15 tcc ctg aga ctc tcc tgt gca gcc tct gga ttc acc ttt gat gaa tat      96
Ser Leu Arg Leu Ser Cys Ala Ala Ser Gly Phe Thr Phe Asp Glu Tyr
            20                  25                  30 ggc atg act tgg gtc cgc caa gtt cca ggg aag ggg ctg gag tgg gtc     144

-continued

```
                Gly Met Thr Trp Val Arg Gln Val Pro Gly Lys Gly Leu Glu Trp Val
                             35                  40                  45 tct ggt att act tgg aat ggt ggt ttc aca gat tat aca gac tct gtg            192
Ser Gly Ile Thr Trp Asn Gly Gly Phe Thr Asp Tyr Thr Asp Ser Val
 50                  55                  60 aag ggc cga ttc acc agc tcc aga gac aac gcc aag aac tcc ctg tat            240
Lys Gly Arg Phe Thr Ser Ser Arg Asp Asn Ala Lys Asn Ser Leu Tyr
 65                  70                  75                  80 ctg caa atg aac agt ctg aga gcc gag gac acg gcc ttg tat tac tgt            288
Leu Gln Met Asn Ser Leu Arg Ala Glu Asp Thr Ala Leu Tyr Tyr Cys
                     85                  90                  95 gcg aga gat gga tat agc agc tcg tgg ggg gct tat gat ata tgg ggc            336
Ala Arg Asp Gly Tyr Ser Ser Ser Trp Gly Ala Tyr Asp Ile Trp Gly
                    100                 105                 110 caa ggg aca atg gtc acc gtc tct tca                                        363
Gln Gly Thr Met Val Thr Val Ser Ser
            115                 120
```

<210> SEQ ID NO 51
<211> LENGTH: 121
<212> TYPE: PRT
<213> ORGANISM: Homo sapiens

<400> SEQUENCE: 51

```
Glu Val Gln Leu Val Glu Ser Gly Gly Val Val Arg Pro Gly Gly
 1               5                  10                  15

Ser Leu Arg Leu Ser Cys Ala Ala Ser Gly Phe Thr Phe Asp Glu Tyr
                 20                  25                  30

Gly Met Thr Trp Val Arg Gln Val Pro Gly Lys Gly Leu Glu Trp Val
             35                  40                  45

Ser Gly Ile Thr Trp Asn Gly Gly Phe Thr Asp Tyr Thr Asp Ser Val
 50                  55                  60

Lys Gly Arg Phe Thr Ser Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Asp Gly Tyr Ser Ser Ser Trp Gly Ala Tyr Asp Ile Trp Gly
                100                 105                 110

Gln Gly Thr Met Val Thr Val Ser Ser
            115                 120
```

<210> SEQ ID NO 52
<211> LENGTH: 24
<212> TYPE: DNA
<213> ORGANISM: Homo sapiens

<400> SEQUENCE: 52
ggattcacct ttgatgaata tggc                                                  24

<210> SEQ ID NO 53
<211> LENGTH: 8
<212> TYPE: PRT
<213> ORGANISM: Homo sapiens

<400> SEQUENCE: 53

```
Gly Phe Thr Phe Asp Glu Tyr Gly
 1               5
```

<210> SEQ ID NO 54
<211> LENGTH: 24

<212> TYPE: DNA
<213> ORGANISM: Homo sapiens

<400> SEQUENCE: 54
attacttgga atggtggttt caca                                              24

<210> SEQ ID NO 55
<211> LENGTH: 8
<212> TYPE: PRT
<213> ORGANISM: Homo sapiens

<400> SEQUENCE: 55

Ile Thr Trp Asn Gly Gly Phe Thr
1               5

<210> SEQ ID NO 56
<211> LENGTH: 42
<212> TYPE: DNA
<213> ORGANISM: Homo sapiens

<400> SEQUENCE: 56
gcgagagatg gatatagcag ctcgtggggg gcttatgata ta                          42

<210> SEQ ID NO 57
<211> LENGTH: 14
<212> TYPE: PRT
<213> ORGANISM: Homo sapiens

<400> SEQUENCE: 57

Ala Arg Asp Gly Tyr Ser Ser Ser Trp Gly Ala Tyr Asp Ile
1               5                   10

<210> SEQ ID NO 58
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 58 gac atc cag atg acc cag tct cca tca tcc ctg tct gca tct gtg gga      48
Asp Ile Gln Met Thr Gln Ser Pro Ser Ser Leu Ser Ala Ser Val Gly
1               5                   10                  15 gac aga gtc acc atc act tgc cgg gca agt cag agc att agc acc tat      96
Asp Arg Val Thr Ile Thr Cys Arg Ala Ser Gln Ser Ile Ser Thr Tyr
            20                  25                  30 tta aat tgg tat cag cag aaa cca ggg aaa gcc cct aag ctc ctg atc     144
Leu Asn Trp Tyr Gln Gln Lys Pro Gly Lys Ala Pro Lys Leu Leu Ile
        35                  40                  45 tat gct gca tcc agt ttg caa agt ggg gtc cca tta agg ttc agt ggc     192
Tyr Ala Ala Ser Ser Leu Gln Ser Gly Val Pro Leu Arg Phe Ser Gly
    50                  55                  60 agt gga tct ggg act gat ttc act ctc acc atc agc agt ctg caa cct     240
Ser Gly Ser Gly Thr Asp Phe Thr Leu Thr Ile Ser Ser Leu Gln Pro
65                  70                  75                  80 gaa gat ttt gca agt tat ttc tgt caa cag agt tac agt acc ccg tac     288
Glu Asp Phe Ala Ser Tyr Phe Cys Gln Gln Ser Tyr Ser Thr Pro Tyr
                85                  90                  95 act ttt ggc cag ggg acc aag ctg gag atc aaa                         321
Thr Phe Gly Gln Gly Thr Lys Leu Glu Ile Lys
            100                 105

```
<210> SEQ ID NO 59
<211> LENGTH: 107
<212> TYPE: PRT
<213> ORGANISM: Homo sapiens

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Leu Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Phe Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 60
<211> LENGTH: 18
<212> TYPE: DNA
<213> ORGANISM: Homo sapiens

<400> SEQUENCE: 60
cagagcatta gcacctat                                                 18

<210> SEQ ID NO 61
<211> LENGTH: 6
<212> TYPE: PRT
<213> ORGANISM: Homo sapiens

<400> SEQUENCE: 61

Gln Ser Ile Ser Thr Tyr
1               5

<210> SEQ ID NO 62
<211> LENGTH: 9
<212> TYPE: DNA
<213> ORGANISM: Homo sapiens

<400> SEQUENCE: 62 gctgcatcc                                                            9

<210> SEQ ID NO 63
<211> LENGTH: 3
<212> TYPE: PRT
<213> ORGANISM: Homo sapiens

<400> SEQUENCE: 63

Ala Ala Ser
1

<210> SEQ ID NO 64
<211> LENGTH: 27
<212> TYPE: DNA
<213> ORGANISM: Homo sapiens

<400> SEQUENCE: 64
caacagagtt acagtacccc gtacact                                       27
```

-continued

<210> SEQ ID NO 65
<211> LENGTH: 9
<212> TYPE: PRT
<213> ORGANISM: Homo sapiens

<400> SEQUENCE: 65

Gln Gln Ser Tyr Ser Thr Pro Tyr Thr
1               5

<210> SEQ ID NO 66
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 66 gaa gtg cag ctg gtg gag tct ggg gga ggc gtg gta cag cct ggg ggg      48
Glu Val Gln Leu Val Glu Ser Gly Gly Gly Val Val Gln Pro Gly Gly
1               5                   10                  15 tcc ctg aga ctc tcc tgt gca gcc tct gga ttc acc ttt aat gat tat      96
Ser Leu Arg Leu Ser Cys Ala Ala Ser Gly Phe Thr Phe Asn Asp Tyr
            20                  25                  30 gcc atg cac tgg gtc cgt caa gct cca ggg aag ggt ctg gag tgg gtc     144
Ala Met His Trp Val Arg Gln Ala Pro Gly Lys Gly Leu Glu Trp Val
        35                  40                  45 tct ctt att agt gga gat ggt ggt aac aca tac tat gca gac tct gtg     192
Ser Leu Ile Ser Gly Asp Gly Gly Asn Thr Tyr Tyr Ala Asp Ser Val
    50                  55                  60 aag ggc cga ctc acc atc tcc aga gac aac agc aaa aac tcc ctg tat     240
Lys Gly Arg Leu Thr Ile Ser Arg Asp Asn Ser Lys Asn Ser Leu Tyr
65                  70                  75                  80 ctg caa atg aac agt ctg aga aca gag gac acc gcc tta tat tac tgt     288
Leu Gln Met Asn Ser Leu Arg Thr Glu Asp Thr Ala Leu Tyr Tyr Cys
                85                  90                  95 gca aaa gat aag ggc tgg aac ttc ggt tac ttc gat ctc tgg ggc cgt     336
Ala Lys Asp Lys Gly Trp Asn Phe Gly Tyr Phe Asp Leu Trp Gly Arg
            100                 105                 110 ggc acc ctg gtc act gtc tcc tca                                     360
Gly Thr Leu Val Thr Val Ser Ser
        115                 120

<210> SEQ ID NO 67
<211> LENGTH: 120
<212> TYPE: PRT
<213> ORGANISM: Homo sapiens

<400> SEQUENCE: 67

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Leu Ile Ser Gly Asp Gly Gly Asn Thr Tyr Tyr Ala Asp Ser Val
    50                  55                  60

Lys Gly Arg Leu Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys

```
                    85                  90                  95
Ala Lys Asp Lys Gly Trp Asn Phe Gly Tyr Phe Asp Leu Trp Gly Arg
            100                 105                 110

Gly Thr Leu Val Thr Val Ser Ser
        115                 120
```

<210> SEQ ID NO 68
<211> LENGTH: 24
<212> TYPE: DNA
<213> ORGANISM: Homo sapiens

<400> SEQUENCE: 68
ggattcacct ttaatgatta tgcc                                      24

<210> SEQ ID NO 69
<211> LENGTH: 8
<212> TYPE: PRT
<213> ORGANISM: Homo sapiens

<400> SEQUENCE: 69

```
Gly Phe Thr Phe Asn Asp Tyr Ala
1               5
```

<210> SEQ ID NO 70
<211> LENGTH: 24
<212> TYPE: DNA
<213> ORGANISM: Homo sapiens

<400> SEQUENCE: 70
attagtggag atggtggtaa caca                                      24

<210> SEQ ID NO 71
<211> LENGTH: 8
<212> TYPE: PRT
<213> ORGANISM: Homo sapiens

<400> SEQUENCE: 71

```
Ile Ser Gly Asp Gly Gly Asn Thr
1               5
```

<210> SEQ ID NO 72
<211> LENGTH: 39
<212> TYPE: DNA
<213> ORGANISM: Homo sapiens

<400> SEQUENCE: 72
gcaaaagata agggctggaa cttcggttac ttcgatctc                       39

<210> SEQ ID NO 73
<211> LENGTH: 13
<212> TYPE: PRT
<213> ORGANISM: Homo sapiens

<400> SEQUENCE: 73

```
Ala Lys Asp Lys Gly Trp Asn Phe Gly Tyr Phe Asp Leu
1               5                   10
```

<210> SEQ ID NO 74
<211> LENGTH: 327
<212> TYPE: DNA
<213> ORGANISM: Homo sapiens
<220> FEATURE:
<221> NAME/KEY: CDS
<222> LOCATION: (1)..(327)

```
<400> SEQUENCE: 74 gac atc cag atg acc cag tct cca tcc tcc ctg tct aca tct gtg gga       48
Asp Ile Gln Met Thr Gln Ser Pro Ser Ser Leu Ser Thr Ser Val Gly
1               5                   10                  15 gac aga gtc acc atc act tgc cgg gca agt cag aac att gac acc tat       96
Asp Arg Val Thr Ile Thr Cys Arg Ala Ser Gln Asn Ile Asp Thr Tyr
            20                  25                  30 tta aat tgg tat cag cag aaa cca ggg aaa gcc cct aaa ctc ctg atc      144
Leu Asn Trp Tyr Gln Gln Lys Pro Gly Lys Ala Pro Lys Leu Leu Ile
        35                  40                  45 tat gat gca tcc agt tta caa agt ggg gtc cca tca cgg ttc agt ggc      192
Tyr Asp Ala Ser Ser Leu Gln Ser Gly Val Pro Ser Arg Phe Ser Gly
    50                  55                  60 agc gga tct ggg aca gat ttc act ctc acc atc acc agt ctg caa cct      240
Ser Gly Ser Gly Thr Asp Phe Thr Leu Thr Ile Thr Ser Leu Gln Pro
65                  70                  75                  80 gaa gat ttt gcc act tac tac tgt caa cag aat gac aat att ctt cac      288
Glu Asp Phe Ala Thr Tyr Tyr Cys Gln Gln Asn Asp Asn Ile Leu His
                85                  90                  95 cct ctc act ttc ggc gga ggg acc aag gtg gag atc aaa                  327
Pro Leu Thr Phe Gly Gly Gly Thr Lys Val Glu Ile Lys
            100                 105

<210> SEQ ID NO 75
<211> LENGTH: 109
<212> TYPE: PRT
<213> ORGANISM: Homo sapiens

<400> SEQUENCE: 75

Asp Ile Gln Met Thr Gln Ser Pro Ser Ser Leu Ser Thr Ser Val Gly
1               5                   10                  15

Asp Arg Val Thr Ile Thr Cys Arg Ala Ser Gln Asn Ile Asp Thr Tyr
            20                  25                  30

Leu Asn Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Asn Asp Asn Ile Leu His
                85                  90                  95

Pro Leu Thr Phe Gly Gly Gly Thr Lys Val Glu Ile Lys
            100                 105

<210> SEQ ID NO 76
<211> LENGTH: 18
<212> TYPE: DNA
<213> ORGANISM: Homo sapiens

<400> SEQUENCE: 76
cagaacattg acacctat                                                   18

<210> SEQ ID NO 77
<211> LENGTH: 6
<212> TYPE: PRT
<213> ORGANISM: Homo sapiens

<400> SEQUENCE: 77

Gln Asn Ile Asp Thr Tyr
```

<210> SEQ ID NO 78
<211> LENGTH: 9
<212> TYPE: DNA
<213> ORGANISM: Homo sapiens

<400> SEQUENCE: 78 gatgcatcc                                                                 9

<210> SEQ ID NO 79
<211> LENGTH: 3
<212> TYPE: PRT
<213> ORGANISM: Homo sapiens

<400> SEQUENCE: 79

Asp Ala Ser
1

<210> SEQ ID NO 80
<211> LENGTH: 33
<212> TYPE: DNA
<213> ORGANISM: Homo sapiens

<400> SEQUENCE: 80
caacagaatg acaatattct tcaccctctc act                                     33

<210> SEQ ID NO 81
<211> LENGTH: 11
<212> TYPE: PRT
<213> ORGANISM: Homo sapiens

<400> SEQUENCE: 81

Gln Gln Asn Asp Asn Ile Leu His Pro Leu Thr
1               5                   10

<210> SEQ ID NO 82
<211> LENGTH: 447
<212> TYPE: PRT
<213> ORGANISM: Homo sapiens

<400> SEQUENCE: 82

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Ser Ser
            20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Ser Ser Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asn Val Asp Thr Thr Met Ile Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Lys Thr Tyr Thr Cys Asn Val Asp His Lys
    195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Leu His Glu Ala Leu
            420                 425                 430

His Ser His Tyr Thr Gln Lys Ser Leu Ser Leu Ser Leu Gly Lys
        435                 440                 445

<210> SEQ ID NO 83
<211> LENGTH: 214
<212> TYPE: PRT
<213> ORGANISM: Homo sapiens

<400> SEQUENCE: 83

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ala Gly
    50                  55                  60

Arg Gly Ser Gly Thr Asp Phe Thr Leu Thr Ile Ser Ser Leu Gln Pro
65                  70                  75                  80
```

```
Glu Asp Phe Ala Thr Tyr Tyr Cys Leu Gln Asp Phe Asn Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 84
<211> LENGTH: 224
<212> TYPE: PRT
<213> ORGANISM: Homo sapiens

<400> SEQUENCE: 84

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Leu Ile Trp Leu Asp Gly Ser Asn Asp Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Asp Gly Pro Val Ala Ala Ile Pro Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220
```

<210> SEQ ID NO 85
<211> LENGTH: 214
<212> TYPE: PRT
<213> ORGANISM: Homo sapiens

<400> SEQUENCE: 85

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Leu Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Asn Thr Tyr Ser Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 86
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 86 gag gtg cag ctg gtg gag tct ggg gga ggc ttg gtc caa ccg ggg ggg     48
Glu Val Gln Leu Val Glu Ser Gly Gly Gly Leu Val Gln Pro Gly Gly
1               5                   10                  15 tcc ctg aga ctc tcc tgt gca gcc tct gga ttc cac tct aat aga tat     96
Ser Leu Arg Leu Ser Cys Ala Ala Ser Gly Phe His Ser Asn Arg Tyr
            20                  25                  30 tgg atg gac tgg gtc cgc cag gct cca ggg aag ggg ctg gag tgg gtg    144
Trp Met Asp Trp Val Arg Gln Ala Pro Gly Lys Gly Leu Glu Trp Val
        35                  40                  45 gcc aac ata aag caa gat gga agt gag gaa aac tat gtg gac tct gtg    192
Ala Asn Ile Lys Gln Asp Gly Ser Glu Glu Asn Tyr Val Asp Ser Val
    50                  55                  60 aag ggc cga ttc acc atc tcc aga gac aac gcc aag aac tca ctt tat    240
Lys Gly Arg Phe Thr Ile Ser Arg Asp Asn Ala Lys Asn Ser Leu Tyr
65                  70                  75                  80

```
ctg caa atg aac agc ctg aga gcc gag gac acg gct gtg tat tac tgt    288
Leu Gln Met Asn Ser Leu Arg Ala Glu Asp Thr Ala Val Tyr Tyr Cys
            85                  90                  95 gcg aga gat cga agc acc tcg tgg gtc cct tac tgg ttc ttc gat ctc    336
Ala Arg Asp Arg Ser Thr Ser Trp Val Pro Tyr Trp Phe Phe Asp Leu
            100                 105                 110 tgg ggc cgt ggc acc ctg gtc act gtc tcc tca                        369
Trp Gly Arg Gly Thr Leu Val Thr Val Ser Ser
            115                 120
```

<210> SEQ ID NO 87
<211> LENGTH: 123
<212> TYPE: PRT
<213> ORGANISM: Homo sapiens

<400> SEQUENCE: 87

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe His Ser Asn Arg Tyr
            20                  25                  30

Trp Met Asp Trp Val Arg Gln Ala Pro Gly Lys Gly Leu Glu Trp Val
        35                  40                  45

Ala Asn Ile Lys Gln Asp Gly Ser Glu Glu Asn Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Ser Thr Ser Trp Val Pro Tyr Trp Phe Phe Asp Leu
            100                 105                 110

Trp Gly Arg Gly Thr Leu Val Thr Val Ser Ser
            115                 120
```

<210> SEQ ID NO 88
<211> LENGTH: 24
<212> TYPE: DNA
<213> ORGANISM: Homo sapiens

<400> SEQUENCE: 88
ggattccact ctaatagata ttgg                                          24

<210> SEQ ID NO 89
<211> LENGTH: 8
<212> TYPE: PRT
<213> ORGANISM: Homo sapiens

<400> SEQUENCE: 89

```
Gly Phe His Ser Asn Arg Tyr Trp
1               5
```

<210> SEQ ID NO 90
<211> LENGTH: 24
<212> TYPE: DNA
<213> ORGANISM: Homo sapiens

<400> SEQUENCE: 90
ataaagcaag atggaagtga ggaa                                          24

<210> SEQ ID NO 91
<211> LENGTH: 8

```
<212> TYPE: PRT
<213> ORGANISM: Homo sapiens

<400> SEQUENCE: 91

Ile Lys Gln Asp Gly Ser Glu Glu
1               5

<210> SEQ ID NO 92
<211> LENGTH: 48
<212> TYPE: DNA
<213> ORGANISM: Homo sapiens

<400> SEQUENCE: 92
gcgagagatc gaagcacctc gtgggtccct tactggttct tcgatctc            48

<210> SEQ ID NO 93
<211> LENGTH: 16
<212> TYPE: PRT
<213> ORGANISM: Homo sapiens

<400> SEQUENCE: 93

Ala Arg Asp Arg Ser Thr Ser Trp Val Pro Tyr Trp Phe Phe Asp Leu
1               5                   10                  15

<210> SEQ ID NO 94
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 94 gac atc cag atg acc cag tct cca tcc tcc ctg tct gca tct gta gga      48
Asp Ile Gln Met Thr Gln Ser Pro Ser Ser Leu Ser Ala Ser Val Gly
1               5                   10                  15 gac aga gtc acc atc act tgc cgg gca agt cag agc att agc agc tat      96
Asp Arg Val Thr Ile Thr Cys Arg Ala Ser Gln Ser Ile Ser Ser Tyr
            20                  25                  30 tta aat tgg tat cag cag aaa cca ggg aaa gcc cct aag ctc ctg atc     144
Leu Asn Trp Tyr Gln Gln Lys Pro Gly Lys Ala Pro Lys Leu Leu Ile
        35                  40                  45 tat gct gca tcc agt ttg caa agt ggg gtc ccg tca agg ttc agt ggc     192
Tyr Ala Ala Ser Ser Leu Gln Ser Gly Val Pro Ser Arg Phe Ser Gly
    50                  55                  60 agt gga tct ggg aca gat ttc act ctc acc atc agc agt ctg caa cct     240
Ser Gly Ser Gly Thr Asp Phe Thr Leu Thr Ile Ser Ser Leu Gln Pro
65                  70                  75                  80 gaa gat ttt gca act tac tac tgt caa cag agt tac agt acc cct ccg     288
Glu Asp Phe Ala Thr Tyr Tyr Cys Gln Gln Ser Tyr Ser Thr Pro Pro
                85                  90                  95 atc acc ttc ggc caa ggg aca cga ctg gag att aaa                     324
Ile Thr Phe Gly Gln Gly Thr Arg Leu Glu Ile Lys
            100                 105

<210> SEQ ID NO 95
<211> LENGTH: 108
<212> TYPE: PRT
<213> ORGANISM: Homo sapiens

<400> SEQUENCE: 95

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Ile Thr Phe Gly Gln Gly Thr Arg Leu Glu Ile Lys
            100                 105
```

<210> SEQ ID NO 96
<211> LENGTH: 18
<212> TYPE: DNA
<213> ORGANISM: Homo sapiens

<400> SEQUENCE: 96
cagagcatta gcagctat                                                18

<210> SEQ ID NO 97
<211> LENGTH: 6
<212> TYPE: PRT
<213> ORGANISM: Homo sapiens

<400> SEQUENCE: 97

```
Gln Ser Ile Ser Ser Tyr
1               5
```

<210> SEQ ID NO 98
<211> LENGTH: 9
<212> TYPE: DNA
<213> ORGANISM: Homo sapiens

<400> SEQUENCE: 98 gctgcatcc                                                           9

<210> SEQ ID NO 99
<211> LENGTH: 3
<212> TYPE: PRT
<213> ORGANISM: Homo sapiens

<400> SEQUENCE: 99

```
Ala Ala Ser
1
```

<210> SEQ ID NO 100
<211> LENGTH: 30
<212> TYPE: DNA
<213> ORGANISM: Homo sapiens

<400> SEQUENCE: 100
caacagagtt acagtacccc tccgatcacc                                   30

<210> SEQ ID NO 101
<211> LENGTH: 10
<212> TYPE: PRT
<213> ORGANISM: Homo sapiens

<400> SEQUENCE: 101

```
Gln Gln Ser Tyr Ser Thr Pro Pro Ile Thr
```

<210> SEQ ID NO 102
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 102

```
gaa gtg cag ctg gtg gag tct ggg gga ggc gtg gta cag cgg ggg gag      48
Glu Val Gln Leu Val Glu Ser Gly Gly Gly Val Val Gln Arg Gly Glu
1               5                   10                  15 tcc ctg aga ctc tcc tgt tca gcc tct gac ttc atc ttt aaa gat tat      96
Ser Leu Arg Leu Ser Cys Ser Ala Ser Asp Phe Ile Phe Lys Asp Tyr
            20                  25                  30 gcc atg tac tgg gtc cgt caa att cca ggg aag ggt cta gag tgg atc     144
Ala Met Tyr Trp Val Arg Gln Ile Pro Gly Lys Gly Leu Glu Trp Ile
        35                  40                  45 tct ctt att agt ggt gat ggt gac act aca tgg tat gga gac tct gtg     192
Ser Leu Ile Ser Gly Asp Gly Asp Thr Thr Trp Tyr Gly Asp Ser Val
    50                  55                  60 aag ggc cga ttc acc atc tcc aga gac aac aac gaa aac tcc ctc ttt     240
Lys Gly Arg Phe Thr Ile Ser Arg Asp Asn Asn Glu Asn Ser Leu Phe
65                  70                  75                  80 ctg caa atg aac gat ctg aga act gag gac acc gcc atg tac tac tgt     288
Leu Gln Met Asn Asp Leu Arg Thr Glu Asp Thr Ala Met Tyr Tyr Cys
                85                  90                  95 gca aga gat atg ggg tgg aac ttc ttt cag ttg caa tac tgg ggc cag     336
Ala Arg Asp Met Gly Trp Asn Phe Phe Gln Leu Gln Tyr Trp Gly Gln
            100                 105                 110 gga acc ctg gtc acc gtc tcc tca                                      360
Gly Thr Leu Val Thr Val Ser Ser
        115                 120
```

<210> SEQ ID NO 103
<211> LENGTH: 120
<212> TYPE: PRT
<213> ORGANISM: Homo sapiens

<400> SEQUENCE: 103

```
Glu Val Gln Leu Val Glu Ser Gly Gly Gly Val Val Gln Arg Gly Glu
1               5                   10                  15

Ser Leu Arg Leu Ser Cys Ser Ala Ser Asp Phe Ile Phe Lys Asp Tyr
            20                  25                  30

Ala Met Tyr Trp Val Arg Gln Ile Pro Gly Lys Gly Leu Glu Trp Ile
        35                  40                  45

Ser Leu Ile Ser Gly Asp Gly Asp Thr Thr Trp Tyr Gly Asp Ser Val
    50                  55                  60

Lys Gly Arg Phe Thr Ile Ser Arg Asp Asn Asn Glu Asn Ser Leu Phe
65                  70                  75                  80

Leu Gln Met Asn Asp Leu Arg Thr Glu Asp Thr Ala Met Tyr Tyr Cys
                85                  90                  95

Ala Arg Asp Met Gly Trp Asn Phe Phe Gln Leu Gln Tyr Trp Gly Gln
            100                 105                 110

Gly Thr Leu Val Thr Val Ser Ser
        115                 120
```

<210> SEQ ID NO 104

```
<211> LENGTH: 24
<212> TYPE: DNA
<213> ORGANISM: Homo sapiens

<400> SEQUENCE: 104
gacttcatct ttaaagatta tgcc                                              24

<210> SEQ ID NO 105
<211> LENGTH: 8
<212> TYPE: PRT
<213> ORGANISM: Homo sapiens

<400> SEQUENCE: 105

Asp Phe Ile Phe Lys Asp Tyr Ala
1               5

<210> SEQ ID NO 106
<211> LENGTH: 24
<212> TYPE: DNA
<213> ORGANISM: Homo sapiens

<400> SEQUENCE: 106
attagtggtg atggtgacac taca                                              24

<210> SEQ ID NO 107
<211> LENGTH: 8
<212> TYPE: PRT
<213> ORGANISM: Homo sapiens

<400> SEQUENCE: 107

Ile Ser Gly Asp Gly Asp Thr Thr
1               5

<210> SEQ ID NO 108
<211> LENGTH: 39
<212> TYPE: DNA
<213> ORGANISM: Homo sapiens

<400> SEQUENCE: 108
gcaagagata tggggtggaa cttctttcag ttgcaatac                              39

<210> SEQ ID NO 109
<211> LENGTH: 13
<212> TYPE: PRT
<213> ORGANISM: Homo sapiens

<400> SEQUENCE: 109

Ala Arg Asp Met Gly Trp Asn Phe Phe Gln Leu Gln Tyr
1               5                   10
```